United States Patent
Wagner et al.

[11] Patent Number: 5,563,172
[45] Date of Patent: Oct. 8, 1996

[54] MACROCYCLIC AMIDE AND UREA IMMUNOMODULATORS

[75] Inventors: Rolf Wagner; Jay R. Luly; Yat S. Or, all of Libertyville, Ill.

[73] Assignee: Abbott Laboratories, Abbott Park, Ill.

[21] Appl. No.: 213,394

[22] Filed: Mar. 14, 1994

Related U.S. Application Data

[63] Continuation-in-part of Ser. No. 149,419, Nov. 9, 1993, abandoned, which is a continuation-in-part of Ser. No. 32,958, filed as PCT/US92/07600, Sep. 8, 1992, published as WO93/04680, Mar. 18, 1993, abandoned, which is a continuation-in-part of Ser. No. 755,208, Sep. 5, 1991, abandoned.

[51] Int. Cl.⁶ .................. C07D 491/16; A61K 31/395
[52] U.S. Cl. .................. 514/456; 514/183; 514/291; 514/411
[58] Field of Search .................. 540/456; 514/291, 514/411

[56] References Cited

U.S. PATENT DOCUMENTS

| | | | |
|---|---|---|---|
| 5,162,334 | 11/1992 | Goulet et al. | 540/456 |
| 5,189,042 | 2/1993 | Goulet et al. | 540/456 |
| 5,250,678 | 10/1993 | Goulet et al. | 540/456 |
| 5,252,732 | 10/1993 | Sinclair et al. | 540/456 |

FOREIGN PATENT DOCUMENTS

| | | | |
|---|---|---|---|
| 515071 | 12/1992 | European Pat. Off. | 540/456 |
| 532088 | 3/1993 | European Pat. Off. | 540/456 |
| 536896 | 4/1993 | European Pat. Off. | 540/456 |
| WO92/20688 | 11/1992 | WIPO | 540/456 |
| WO93/04680 | 3/1993 | WIPO | 540/456 |

*Primary Examiner*—Robert T. Bond
*Attorney, Agent, or Firm*—Andreas M. Danckers; Steven R. Crowley

[57] ABSTRACT

Immunomodulatory macrocyclic compounds having the formula:

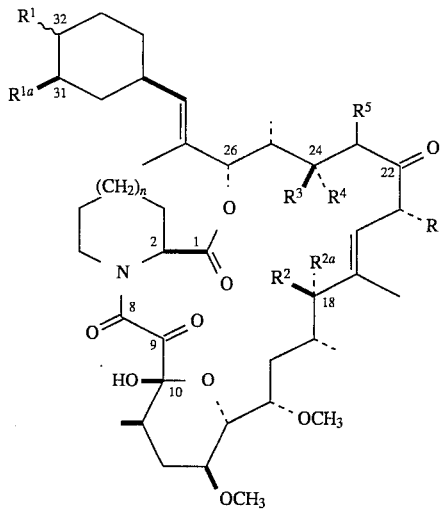

and pharmaceutically-acceptable salts, esters, amides and prodrugs thereof, as well as pharmaceutical compositions containing the same, which possess immunosuppressive, antimicrobial, antifungal, antiviral, antiinflammatory and antiproliferative activity, as well as the ability to reverse chemotherapeutic drug resistance.

10 Claims, No Drawings

MACROCYCLIC AMIDE AND UREA IMMUNOMODULATORS

This application is a continuation-in-part of U.S. patent application Ser. No. 08/149,419, filed Nov. 9, 1993, now abandoned, which is a continuation-in-part of U.S. patent application Ser. No. 08/032,958, filed Mar. 17, 1993, now abandoned, which is a continuation-in-pan of International Patent Application No. PCT/US92/07600, filed Sep. 8, 1992, published as WO93/04680 Mar. 18, 1993, which is a continuation-in-part of U.S. patent application Ser. No. 07/755,208, filed Sep. 5, 1991 and now abandoned.

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, to means for their preparation, to pharmaceutical compositions containing such compounds and to methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Undesired side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus *Streptomyces*. Immunosuppressant FK-506, isolated from a strain of *S. tsukubaensis*, is a 23-membered macrocyclic lactone represented by formula 1a, below. Other related natural products, such as FR-900520 (lb) and FR-900523 (1c), which differ from FK-506 in their alkyl substituent at C-21, have been isolated from *S. hygroscopicus yakushimnaensis*. Yet another analog, FR-900525, produced by *S. tsukubaensis*, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, its toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

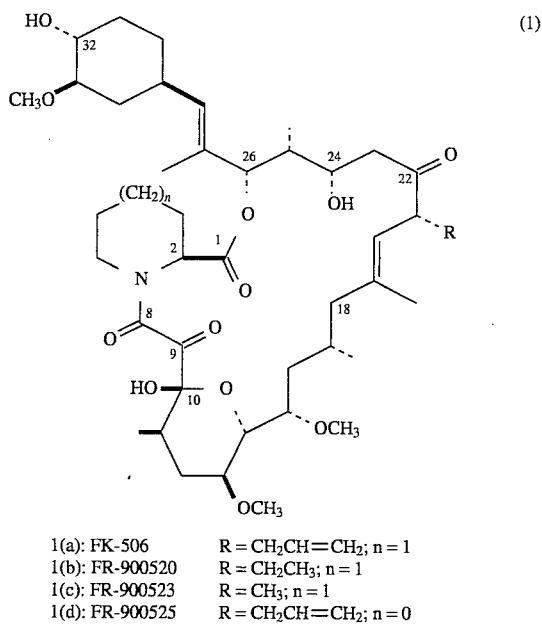

| | |
|---|---|
| 1(a): FK-506 | R = CH$_2$CH=CH$_2$; n = 1 |
| 1(b): FR-900520 | R = CH$_2$CH$_3$; n = 1 |
| 1(c): FR-900523 | R = CH$_3$; n = 1 |
| 1(d): FR-900525 | R = CH$_2$CH=CH$_2$; n = 0 |

Fermentation products of FK-type compounds include C-21-epi derivatives of FK-506 a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13, 31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether and aryl ether formation at C-32 and/or C-24, oxidation of C-32 alcohol to the ketone, and epoxide formation at C-9.

Although some of these modified compounds exhibit immunosuppressive activity, the need remains for macrocyclic irmmunosuppressants which do not have the serious side effects frequently associated with immunosuppressant therapy. Accordingly, one object of the invention is to provide novel semisynthetic macrolides which possess the desired immunomodulatory activity but which minimize undesired side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient,

3 one of the above compounds. Yet another object of the invention is to provide a method of treating a variety of disease states, including post-transplant tissue rejection and autoimmune disfunction.

SUMMARY OF THE INVENTION

The present invention is directed to compounds having the formula:

(I)

and pharmaceutically-acceptable salts, esters, amides and prodrugs thereof, wherein n, R, $R^1$, $R^{1a}$, $R^2$, $R^{2a}$, $R^3$, $R^4$ and $R^5$ are specifically defined, which possess immunosuppressive, antimicrobial, antifungal, antiviral, antiinflammatory and antiproliferative activity, as well as the ability to reverse chemotherapeutic drug resistance; to pharmaceutical compositions comprising a compound of the invention in combination with a pharmaceutically-acceptable carrier; to processes for the preparation of these compounds; to synthetic intermediates useful in the preparations of these and other immunomodulator derivatives of ascomycin; to methods of formulating pharmaceutical compositions comprising these compounds; and to a method of immunomodulatory treatment of a human or veterinary subject in need of such treatment by the administration of a therapeutically-effective amount of a novel compound according to the present invention.

4

DETAILED DESCRIPTION OF THE INVENTION

The instant invention is directed to novel compounds described by the general formula (I):

(I)

and pharmaceutically-acceptable salts, esters, amides and prodrugs thereof, wherein:

n is zero or one;

R is hydrogen, methyl, ethyl, allyl, propyl, 2-hydroxyethyl, cyclopropylmethyl, 2-oxopropyl or 2-ethanal;

$R^1$ and $R^{1a}$ are selected such that one of $R^1$ and $R^{1a}$ is hydrogen, —($C_1$–$C_6$- alkyl)oxy or hydroxy, and the other is chosen from the group consisting of:

(I) —O($CH_2$)$_j$C(O)$R^{12}$, where j is one-to-five, and $R^{12}$ is:

(A) hydroxy;

(B) —O$R^{13}$, wherein $R^{13}$ is:

(i) —($C_1$–$C_{10}$-alkyl);

(ii) —( cyclo-$C_3$–$C_8$-alkyl);

(iii) —(cyclo-$C_3$–$C_8$-alkyl-$C_1$–$C_3$-alkyl);

(iv) aryl-($C_1$–$C_6$-alkyl)-, where aryl is as defined below, wherein the zero, one, two or three substituents on the aryl group, each designated $R^{301}$, are independently selected from the group consisting of:

(a) —($C_1$-to-$C_7$-alkyl);

(b) —($C_2$-to-$C_6$-alkenyl);

(c) halogen;

(d) —($CH_2$)$_m$N$R^8R^9$, where m is zero-to-six, and N$R^8R^9$ is either a nitrogen atom attached to $R^8$ and $R^9$, wherein $R^8$ and $R^9$ are independently selected from the group consisting of:

(1) hydrogen;

(2) —$R^{400}$, where $R^{400}$ is selected from the group consisting of:

a. mod-aryl, as defined below, wherein the one, two, or three substituents, each designated $R^{302}$, are independently selected from the group consisting of:
  1. $-(C_1\text{-to-}C_7\text{-alkyl})$;
  2. $-(C_2\text{to-}C_6\text{-alkenyl})$;
  3. halogen;
  4. $-(CH_2)_m NR^{18}R^{19}$, where m is as defined above and $NR^{18}R^{19}$ is either a nitrogen atom attached to $R^{18}$ and $R^{19}$, wherein $R^{18}$ and $R^{19}$ are independently selected from the group consisting of hydrogen, $-(C_1\text{-}C_6\text{-alkyl})$, unsubstituted aryl-, and unsubstituted aryl-$(C_1\text{-}C_6\text{-alkyl})$; or $NR^{18}R^{19}$ may be a 3-to-7-membered heterocyclic ring comprising ring carbon atoms, the nitrogen atom shown, and zero, one or two additional heteroatoms independently selected from the group consisting of $-O-$, $-NH-$, $-N(C_1\text{-to-}C_6\text{-alkyl})$ and $-S(O)_s-$, wherein s is zero, one or two;
  5. $-CN$;
  6. $-CHO$;
  7. mono-, di-, tri-, or perhalogenated $-C_1\text{-}C_6\text{-alkyl}$, as defined below;
  8. $-S(O)_s R^{18}$, where s and $R^{18}$ are as defined above;
  9. $-C(O)NR^{18}R^{19}$, where $NR^{18}R^{19}$ is as defined above;
  10. $-(CH_2)_m OR^{18}$, where m and $R^{18}$ are as defined above;
  11. $-CH(OR^{16})(OR^{17})$, where $R^{16}$ and $R^{17}$ are independently chosen from $-(C_1\text{-to-}C_3 \text{ alkyl})$ or, taken together, $R^{16}$ and $R^{17}$ form an ethylene or propylene bridge;
  12. $-(CH_2)_m OC(O)R^{18}$, where m and $R^{18}$ are as defined above;
  13. $-(CH_2)_m C(O)OR^{18}$, where m and $R^{18}$ are as defined above;
  14. $-OR\ 10$, where $R^{10}$ is: (i) $-PO(OH)O^-M^+$, wherein $M^+$ is a proton or a positively charged inorganic or organic counterion, as defined below, (ii) $-SO_3^- M^+$, wherein $M^+$ is as defined above, (iii) $-C(O)(CH_2)_m C(O)O^-M^+$, wherein m and $M^+$ are as defined above:
  15. $-NO_2$;
  16. $-N_3$;
  17. $-(C_2\text{-to-}C_6\text{-alkynyl})$;
  18. $-C\equiv C-Si(CH_3)_3$; and
  19. guanidino substituted by hydrogen; $-(C_1\text{-}C_6\text{-alkyl})$; unsubstimted aryl; $(C_1\text{-}C_8\text{-alkyl})\text{-}C(O)$; unsubstituted aryl-$S(O)_2$; $(C_1\text{-}C_6\text{-alkyl})-OC(O)-$; unsubstituted aryl-$(C_1\text{-}C_6\text{-alkyl})-OC(O)$; unsubstituted aryl-$OC(O)$; or $(C_1\text{-}C_6\text{-alkyl})-SO_2-$; or taken together, any two adjacent $R^{302}$ substituents in a di- or trisubstituted mod-aryl group form a 5-, 6- or 7-membered carbocyclic ring or a 5-, 6- or 7-membered heterocyclic ring wherein the ring atoms consist of carbon atoms and one or two heteroatoms independently selected from the group consisting of $-O-$, $-S(O)_s-$, where s is as defined above, and $-NR^1-$, where $R^{18}$ is as defined above;

b. $-Q$-mod-aryl, where mod-aryl is as defined below and substituent(s) $R^{302}$ is/are as defined above, and the divalent radical $-Q-$ is selected from the group consisting of:
  1. $-(C_1\text{-to-}C_6\text{-alkyl})-$;
  2. $-(C_2\text{-to-}C_6\text{-alkenyl})-$;
  3. $-(C_2\text{-to-}C_6\text{-alkynyl})-$;
  4. $-(CH_2)_m O-$, wherein m is as defined above;
  5. $-O(CH_2)_m-$, wherein m is as defined above;
  6. $-N(R^{18})C(O)-$, wherein $R^{18}$ is as defined above;
  7. $-C(O)N(R^{18})-$, wherein $R^{18}$ is as defined above;
  8. $-S(O)_s-$, wherein s is as defined above;
  9. $-N(R^{18})-$, wherein $R^{18}$ is as defined above;
  10. $-N(R^{18})S(O)_t-$, wherein t is one or two, and $R^{18}$ is as defined above;
  11. $-S(O)_t N(R^{18})-$, wherein t and $R^{18}$ are as defined above;
  12. $-C(O)-$;
  13. $-NN-$;
  14. $-CHN-$;
  15. $-NCH-$;
  16. $-ONCH-$; and
  17. $-CHNO-$;

c. $-$mod-Het, as defined below, wherein the one, two, or three substituents, each designated $R^{302}$, are independently selected, and are as defined above;
d. $-Q$-mod-Het, where Q is as defined above;
e. $-$biaryl, as defined below;
f. $-Q$-biaryl, where Q is as defined above;
g. $-$mod-aryl-Q-mod-aryl, where Q is as defined above;
h. $-$mod-aryl-Q-mod-Het, where Q is as defined above;
i. $-$mod-Het-Q-mod-aryl, where Q is as defined above;
j. $-$mod-Het-Q-mod-Het, where Q is as defined above;
k. $-$mod-Het-mod-aryl;
l. -mod-aryl-mod-Het; and
m. -mod-Het-mod-Het;
  (3) $-(C_1\text{-to-}C_6\text{-alkyl})$;
  (4) substituted-$C_1\text{-to-}C_6\text{-alkyl}$, as defined below;
  (5) $-(C_3\text{-to-}C_6\text{-alkenyl})$;
  (6) substituted-$C_3\text{-to-}C_6\text{-alkenyl}$, as defined below;
  (7) $-(C_3\text{-to-}C_6\text{-alkynyl})$;
  (8) substituted-$C_3\text{-to-}C_6\text{-alkynyl}$, as defined below;
  (9) $-(\text{cyclo-}C_3\text{-to-}C_{10}\text{-alkyl})$;
  (10) substituted-cyclo-$C_3\text{-to-}C_{10}\text{-alkyl}$, as defined below;
  (11) $-(\text{cyclo-}C_4\text{-to-}C_{10}\text{-alkenyl})$;
  (12) substituted-cyclo-$C_4\text{-to-}C_{10}\text{-alkenyl}$, as defined below;
  (13) $-(\text{bicyclo-}C_6\text{-to-}C_{10}\text{-alkyl})$;
  (14) substituted-bicyclo-$C_6\text{-to-}C_{10}\text{-alkyl}$, as defined below;
  (15) $-(\text{bicyclo-}C_6\text{-to-}C_{10}\text{-alkenyl})$;
  (16) substituted-bicyclo-$C_6\text{-to-}C_{10}\text{-alkenyl}$, as defined below;
  (17) $-(\text{bicyclo-}C_6\text{-to-}C_{10}\text{-alkenyl})\text{-}C_1\text{-to-}C_6\text{-alkyl}$; and
  (18) substituted-bicyclo-$C_6\text{-to-}C_{10}\text{-alkenyl-}C_1\text{-to-}C_6\text{-alkyl}$, as defined below; or $-NR^8R^9$ may be a 3- to 7-membered heterocyclic ring, where the ring consists of carbon atoms, the nitrogen atom shown, and zero, one or two additional heteroatoms independently selected from the group consisting of $-O-$, $-S(O)_s-$, wherein s is as defined above, and $-NR^8-$, wherein $R^8$ is as defined above;
  (e) $-CN$;
  (f) $-CHO$;
  (g) mono-, di-, tri-, or perhalogenated $-C_1\text{-}C_6\text{-alkyl}$;
  (h) $-S(O)_s R^8$, where s and $R^8$ are as defined above;
  (i) $-C(O)NRSR^9$, where $NRSR^9$ is as defined above;
  (j) $-(CH_2)m\ OR^8$, where m and $R^8$ are as defined above;

(k) —CH(OR$^{16}$)(OR$^{17}$), where R$^{16}$ and R$^{17}$ are as defined above;
(l) —(CH$_2$)$_m$OC(O)RS, where m and R$^8$ are as defined above;
(m) —(CH$_2$)$_m$C(O)ORS, where m and R$^8$ are as defined above;
(n) —OR10, where R$^{10}$ is as defined above;
(o) —NO$_2$;
(p) —N$_3$;
(q) —R$^{400}$, as defined above;
(r) —S(O)$_t$NRSR$_9$, where t and NR$^8$R$^9$ are as defined above;
(s) —NR$^8$S(O)$_t$R$^9$, where t, R$^8$ and R$^9$ are as defined above;
(t) —(C$_2$-to-C$_6$-alkynyl);
(u) —C≡C—Si(CH$_3$)$_3$; and
(v) guanidino substituted by hydrogen; —(C$_1$-C$_6$-alkyl); -mod-aryl; (C$_1$-C$_8$-alkyl)—C(O)—; mod-aryl-SO$_2$—; (C$_1$-C$_6$-alkyl)—OC(O)—; mod-aryl-(C$_1$-C$_6$-alkyl)-OC(O); mod-aryl—OC(O)—; or (C$_1$-C$_6$-alkyl)SO$_2$—; or taken together, any two adjacent R$^{301}$ substituents in a di- or trisubstituted aryl group form a 5-, 6- or 7-membered carbocyclic ring or a 5-, 6- or 7-membered heterocyclic ring wherein the ring atoms consist of carbon atoms and zero, one or two heteroatoms independently selected from the group consisting of —O—, —S(O)$_s$—, where s is as defined above, and —NR$^8$—, where R$^8$ is as defined above; with the proviso that each R$^{301}$ substituent or each ring formed by two adjacent R$^{301}$ groups may comprise no more than twenty non-hydrogen atoms;

(v) aryl-, as defined below and substituent(s) R$^{301}$ is/are as defined above;
(vi) Het-, as defined below;
(vii) heterocyclic-, as defined below;
(viii) mono-, di-, tri-, or per-halogenated-C$_1$-C$_6$-alkyl-;
(ix) —(cyclo-C$_5$-C$_{10}$-alkenyl);
(x) —(cyclo-C$_5$-C$_{10}$-alkenyl-C$_1$-C$_3$-alkyl);
(xi) —(bicyclo-C$_6$-C$_{12}$-alkenyl);
(xii) —(bicyclo-C$_6$-C$_{12}$-alkenyl-C$_1$-C$_3$-alkyl);

(C) —NR$^{14}$R$^{15}$, wherein NR$^{14}$R$^{15}$ is either a nitrogen atom attached to R$^{14}$ and R$^{15}$, wherein R$^{14}$ and R$^{15}$ are independently selected from the group consisting of:
(i) hydrogen;
(ii) —R$^{400}$, as defined above;
(iii) —(C$_1$-to-C$_{10}$-alkyl);
(iv) sub-C$_1$-to-C$_{10}$-alkyl, as defined below;
(v) —(cyclo-C$_3$-to-C$_{10}$-alkyl);
(vi) sub-cyclo-C$_3$-to-C$_{10}$-alkyl, as defined below;
(vii) —(cyclo-C$_3$-to-C$_{10}$-alkyl-C$_1$-to-C$_3$-alkyl);
(viii) sub-cyclo-C$_3$-to-C$_{10}$-alkyl-C$_1$-to-C$_3$-alkyl, as defined below;
(ix) —(C$_3$-to-C$_{10}$-alkenyl);
(x) sub-C$_3$-to-C$_{10}$-alkenyl, as defined below;
(xi) —(cyclo-C$_4$-to-C$_{10}$-alkenyl);
(xii) sub-cyclo-C$_4$-to-C$_{10}$-alkenyl, as defined below;
(xiii) —(cyclo-C$_6$-to-C$_{10}$-alkyl-C$_3$-C$_5$-alkenyl);
(xiv) sub-cyclo-C$_6$-to-C$_{10}$-alkyl-C$_3$-CS-alkenyl, as defined below;
(xv) —(C$_3$-to-C$_{10}$-alkynyl);
(xvi) sub-C$_3$-to-C$_{10}$-alkynyl, as defined below;
(xvii) —(cyclo-C$_6$-to-C$_{10}$-alkyl-C$_3$-C$_5$-alkynyl);
(xviii) sub-cyclo-C$_6$-to-C$_{10}$-alkyl-C$_3$-C$_8$-alkynyl, as defined below;
(xix) -(bicyc 1 o-C$_6$-to-C$_{10}$-alkyl);
(xx) sub-bicyclo-C$_6$-to-C$_{10}$-alkyl, as defined below;
(xxi) —(bicyclo-C$_6$-to-C$_{10}$-alkenyl);
(xxii) sub-bicyclo-C$_6$-to-C$_{10}$-alkenyl, as defined below;
(xxiii) —aryl;
(xxiv) —Het; and
(xxv) R$^6$, where R$^6$ is selected from the group consisting of:
(a) hydrogen;
(b) —(C$_1$-to-C$_{10}$-alkyl);
(c) mod-C$_1$-to-C$_{10}$-alkyl, as defined below;
(d) —(C$_3$-to-C$_{10}$-alkenyl);
(e) mod-C$_3$-to-C$_{10}$-alkenyl, as defined below;
(f) —(C$_3$-to-C10 alkynyl);
(g) mod-C$_3$-to-C$_{10}$-alkynyl, as defined below;
(h) —(cyclo-C$_3$-to-C$_{10}$-alkyl);
(i) mod-cyclo-C$_3$-to-C$_{10}$-alkyl, as defined below;
(j) —(cyclo-C$_4$-to-C$_{10}$-alkenyl);
(k) mod-cyclo-C$_4$-to-C$_{10}$-alkenyl, as defined below;
(l) —(bicyclo-C$_6$-to-C$_{10}$-alkyl);
(m) mod-bicyclo-C$_6$-to-C$_{10}$-alkyl, as defined below;
(n) —(bicyclo-C$_6$-to-C$_{10}$-alkenyl);
(o) mod-bicyclo-C$_6$-to-C$_{10}$-alkenyl, as defined below;
(p) —R$^8$, as defined above;
(q) —aryl; and
(r) —Het; or —NR$^{14}$R$^{15}$ may be a 3- to 7-membered heterocyclic ring, where the ring consists of carbon atoms, the nitrogen atom shown, and zero, one or two additional heteroatoms independently selected from —O—,—S(O)$_s$—, wherein s is as defined above, and —NR$^8$—, wherein R$^8$ is as defined above, which ring is unsubstituted or substituted with from one-to-five compatible radicals independently selected from the group consisting of:

(i) R$^6$, as defined above;
(ii) —(CH$_2$)$_m$OR$_6$, where m and R$^6$ are as defined above;
(iii) —(CH$_2$)$_m$NR$^6$R$^7$, where m is as defined above and NR$^6$R$^7$ is either a nitrogen atom attached to R$^6$ and R$^7$, wherein R$^6$ is as defined above and R$^7$ is independently selected from the group defining R$^6$, or —NR$^6$R$^7$ may be a 3- to 7-membered heterocyclic ring, where the ring consists of carbon atoms, the nitrogen atom shown, and zero, one, or two additional heteroatoms independently selected from the group consisting of —O—, —S(O)$_s$—, wherein s is as defined above, and —NR$^8$—, wherein R$^8$ is as defined above, which ring is unsubstituted or substituted with from one-to-six compatible radicals independently selected from the group consisting of:

(a) —R$^8$, as defined above;
(b) —(CH$_2$)$_m$OR$^8$, wherein m and R$^8$ are as defined above;
(c) —S(O)$_s$R$^8$, wherein s and R$^8$ are as defined above;
(d) —S(O)$_t$NR$^8$R$^9$, wherein t and NR$^8$R$^9$ are as defined above;
(e) —(CH$_2$)$_m$NR$^8$R$^9$, wherein m and NR$^8$R$^9$ are as defined above;
(f) —SO$_3$H;
(g) =NOR$^8$, wherein R$^8$ is as defined above;
(h) —R$^{400}$, as defined above;
(i) —aryl;
(j) —Het; and
(k) —R$^{399}$, wherein R$^{399}$ is selected from the group consisting of:
(1) hydroxyl;
(2) —C(O)OH;
(3) —C(O)OR$^8$, where R$^8$ is as defined above;
(4) —(cyclo-C$_3$-to-C$_7$-alkyl);
(5) oxo;

(6) thiooxo;
(7) epoxy;
(8) halogen;
(9) —CN;
(10) —$N_3$;
(11) —$NO_2$;
(12) —$OR^{10}$, where $R^{10}$ is as defined above;
(13) —$S(O)_tNR^8R^9$, where t and $NR^8R^9$ are as defined above;
(14) —$NR^8S(O)_tR^9$, where t, $R^8$ and $R^9$ are as defined above;
(15) —$CH(OR^{16})(OR^{17})$, where $R^{16}$ and $R^{17}$ are as defined above; and
(16) guanidino substituted by hydrogen, —($C_1$–$C^6$-alkyl); aryl; ($C_1$–$C_6$-alkyl)CO—; aryl-$SO_2$—; ($C_1$–$C_6$-alkyl)OC(O)—; aryl-($C_1$–$C_6$-alkyl)OC(O)—; aryl-OC(O)—; or ($C_1$–$C_6$-alkyl)—$SO_2$—;
(iv) —$C(O)OR^6$, where $R^6$ is as defined above;
(v) —$SO_3H$;
(vi) —$S(O)_2R^6$, where s and $R^6$ are as defined above;
(vii) —$S(O)_tNR^6R^7$, where t and $NR^6R^7$ are as defined above;
(viii) =$NOR^6$, where $R^6$ is as defined above;
(ix) —aryl;
(x) —Het;
(xi) —$R^{399}$, as defined above; and
(xii) —$R^{400}$, as defined above;
(D) —aryl;
(E) Het—;
(F) mono-, di-, tri-, or per-halogenated-$C_1$–$C_6$alkyl;
(G) N—($R^8$)$NR^{14}R^{15}$, where $R^8$ and $NR^{14}R^{15}$ are as defined above;
(H) —$Si(R^{11})_3$, where each $R^{11}$ is independently -($C_1$–$C_6$-alkyl), aryl-($C_1$–$C_6$-alkyl)—, or aryl;
(I) —$OSi(R^{11})_3$, where each $R^{11}$ is independently as defined above;
(J) —$Sn(R^{11})_3$, where each $R^{11}$ is independently as defined above;
(K) —$P(R^{11})_2$, where each $R^{11}$ is independently as defined above;
(L) —$R^{14}$, where $R^{14}$ is as defined above; or
(M) halogen;
(II) —$O(CH_2)_mS(O)_sR^{12}$, where m, s and $R^{12}$ are as defined above;
(III) —$O(CH_2)_jCN$, where j is as defined above;
(IV) —$O(CH_2)_jC(=NOR^{14})R^{12}$, where j, $R^{12}$ and $R^{14}$ are as defined above;
(V) —$O(CH_2)_jC(=N+(O—)R^{14})R^{12}$, where j, $R^{12}$ and $R^{14}$ are as defined above, with the proviso that $R^{14}$ may not be hydrogen;
(VI) —$O(CH_2)_jC(=NOR^{14})R^{15}$, where j, $R^{14}$ and $R^{15}$ are as defined above;
(VII) —$O(CH_2)_jC(=N+(O—)R^{14})R^{15}$, where j, R 14 and $R^{15}$ are as defined above, with the proviso that $R^{14}$ may not be hydrogen;
(VIII) —$OC(O)O(CH_2)_jC(O)NR^{14}R^{15}$, where j and $NR^{14}R^{15}$ are as defined above;
(IX) —$O(CH_2)_jNR^6C(O)OR^{14}$, where j, $R^6$ and $R^{14}$ are as defined above;
(X) —$O(CH_2)_jNR^6C(O)NR^{14}R^{15}$, where j, $R^6$ and $NR^{14}R^{15}$ are as defined above;
(XI) —$O(CH_2)_jNR^6C(O)NR^7NR^{14}R^{15}$, where j, $R^6$, $R^7$ and $NR^{14}R^{15}$ are as defined above;
(XII) —$O(CH_2)_jNR^6C(O)R^{14}$, where j, $R^6$ and $R^{14}$ are as defined above; and
(XIII) —$O(CH_2)_jNR^6C(O)OC(O)R^{14}$, where j, $R^6$ and $R^{14}$ are as defined above; $R^2$ and $R^{2a}$ are independently hydrogen, halogen, or —$OR^{14}$, wherein $R^{14}$ is as defined above, or one of $R^2$ and $R^{2a}$ may be hydroxy, when the other of $R^2$ or $R^{2a}$ is hydrogen, or $R^2$ and $R^{2a}$ taken together is oxo or thiooxo;

$R^3$ and $R^4$ are chosen, when $R^5$ is hydrogen, such that one of $R^3$ and $R^4$ is hydrogen and the other is selected from hydrogen, hydroxy, —$OCOR^8$, where $R^8$ is as defined above, or —$OSi(R^{11})_3$, where each $R^{11}$ is independently as defined above, or one of $R^3$ and $R^4$ is joined with non-hydrogen $R^5$ to form a C-23/C-24 bond, with the other being hydrogen, hydroxy, —$OCOR^8$, where $R^8$ is as defined above, or —$OSi(R^{11})_3$, where each $R^{11}$ is independently as defined above;

$R^5$ is hydrogen, or taken together with either $R^3$ or $R^4$, forms a C-23/C-24 bond.

It is understood that when a variable, such as m, s, t, $M^+$, Q, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{301}$, $R^{302}$, $R^{399}$, $R^{400}$, alkyl, alkenyl, alkynyl, aryl, Het, mod-aryl, rood-Her, or the like, occurs more than once in a formula, its value is chosen independently at each occurance. It is further understood that the present application is not claiming substituents or substitution patterns that are impractical or unreasonable to prepare.

Preferred compounds according to the present invention are represented by formula (II):

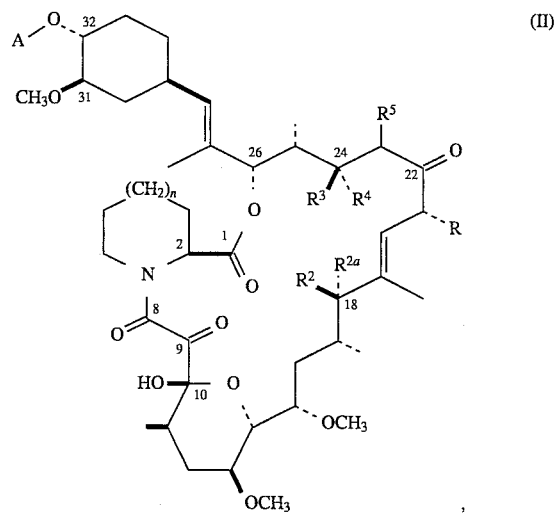

wherein n, R, $R^2$, $R^{2a}$, $R^3$, $R^4$ and $R^5$ are as defined above and A is selected from among:

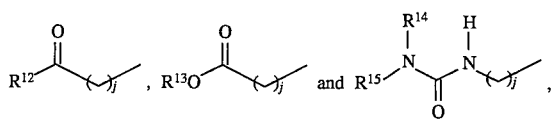

where j, $R^{12}$, $R^{13}$, $R^{14}$ and $R^{15}$ are as defined above.

More preferred compounds according to the present invention are represented by formula (III):

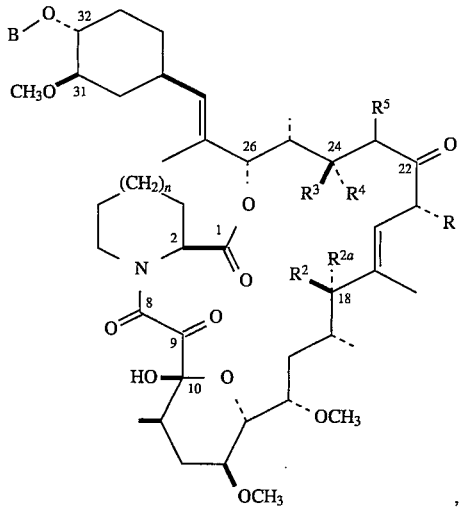

wherein n, R, $R^2$, $R^{2a}$, $R^3$, R4 and $R^5$ are as defined above and B is selected from:

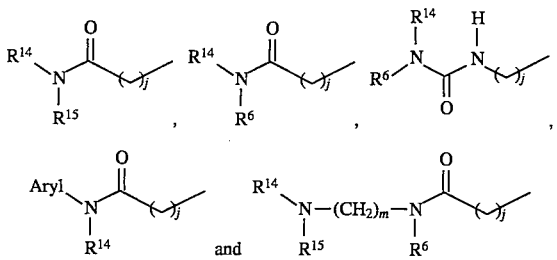

where j, m, $R^6$, $R^{14}$ and $R^{15}$ are as defined above, and aryl is as defined below.

Most preferred compounds according to the present invention are represented by formula (IV):

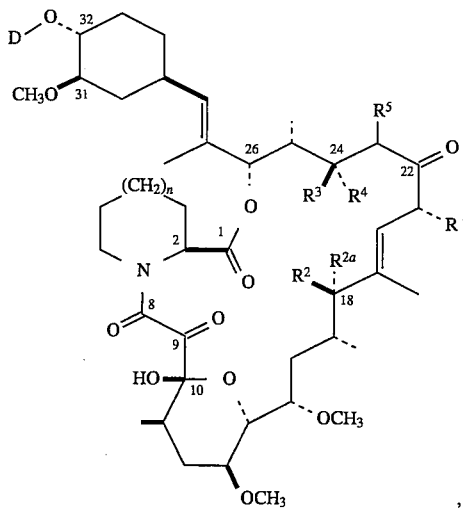

wherein n, R, $R^2$, $R^{2a}$, $R^3$, $R^4$ and $R^5$ are as defined above and D is selected from:

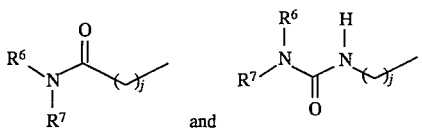

where j, $R^6$ and $R^7$ are as defined above.

Preferred compounds according to the invention are the compounds of:

Formula II, wherein R=ethyl; n=1; $R^2=R^{2a}=R^3=R^5=H$; $R^4$=—OH; and A=—OCH$_2$C(O)—OCH$_2$-[(1R)-(+)-alpha-pinen-10-yl)];

Formula II, wherein R=ethyl; n=1; $R^2=R^{2a}=R^3=R^5=H$; $R^4$=OSi(CH$_3$)$_3$; and A=—OCH$_2$C(O)—O—CH$_2$[(1R)-(+)-a-pinen-10-yl)];

Formula II, wherein R=ethyl; n=1; $R^2=R^{2a}=R^3=R^5=H$; $R^4$=OH; and A=—OCH$_2$C(O)—OC$_2$-(4-nitrophenyl);

Formula II, wherein R=ethyl; n=1; $R^2=R^{2a}=R^3=R^5=H$; $R^4$=OH; and A=—OCH$_2$C(O)OC$_2$H$_5$;

Formula II, wherein R=ethyl; n=1; $R^2=R^{2a}=R^3=R^5=H$; $R^4$=OH; and A=—OCH$_2$C(O)OCH$_2$C$_6$H$_5$;

Formula II, wherein R=ethyl; n=1; $R^2=R^{2a}=R^3=R^5=H$; $R^4$=OH; and A=—OCH$_2$C(O)OH Formula II, wherein R=ethyl; n=1; $R^2=R^{2a}=R^3=R^5=H$; $R^4$=OH; and A=—OCH$_2$C(O)OCH$_2$-(9-fluorenyl);

Formula II, wherein R=ethyl; n=1; $R^2=R^{2a}=R^3=H$; A=—OCH$_2$C(O)OCH$_2$Ph; and $R^4$ and $R^5$ taken together form a bond; and Formula II, wherein R=ethyl; n=1; $R^2=R^{2a}=R^3=R^4=R^5=H$; and A=—OCH$_2$C(O)OH;

Formula II: R=ethyl; n=1; $R^2=R^{2a}=R^3=R^5=H$; $R^4$=OH; A=—OCH$_2$C(O)OCH$_2$CCl$_3$;

More preferred compounds according to the invention are the compounds of: Formula III, wherein R=ethyl; n=1; $R^2=R^{2a}=R^3=R^5=H$; $R^4$=OH; and B=—OCH$_2$C(O)-NHR$^{15}$, where $R^{15}$=—CH(CH3)CONHCH(CH3)CONHCH(CH3)CO2H (all chiral centers in $R^{15}$ are R configuration);

Formula III, wherein R=ethyl; n=1; $R^2=R^{2a}=R^3=R^5=H$; $R^4$=OH; and B=—OCH$_2$C(O)—N(CH$_2$CH$_2$N(CH$_3$)(CH$_2$CH$_2$OH))-phenyl; Formula III, wherein R=ethyl; n=1; $R^2=R^{2a}=R^3=R^5=H$; $R^4$=OH; and B=—OCH$_2$C(O)-N(CH$_2$CH$_2$N(CH$_3$)$_2$)-phenyl;

Formula III, wherein R=ethyl; n=1; $R^2=R^{2a}=R^3=R^5=H$; $R^4$=OH; and B=—OCH$_2$C(O)-NHNHCO$_2$CH$_3$;

Formula III, wherein R=ethyl; n=1; $R^2=R^{2a}=R^3=R^5=H$; $R^4$=OH; and B=—OCH$_2$C(O)-N(CH$_2$CH$_2$OH)—NHCO$_2$CH$_3$;

Formula III, wherein R=ethyl; n=1; $R^2=R^{2a}=R^3=R^5=H$; $R^4$=OH; and B=—OCH$_2$C(O)—N(CH$_2$CH$_2$CH$_2$OCOCH$_2$CH$_2$CO$_2$H)(4-fluorophenyl);

Formula III, wherein R=ethyl; n=1; $R^2=R^{2a}=R^3=R^5=H$; $R^4$=OH; and B=—OCH$_2$C(O)HN-(CH$_2$)$_5$NH-dansyl;

Formula III, wherein R=ethyl; n=1; $R^2=R^{2a}=R^3=R^5=H$; $R^4$=OH; and B=—OCH$_2$C(O)N(phenyl)CH$_2$CH$_2$CH$_2$OH; and Formula III, wherein R=ethyl; n=1; $R^2=R^{2a}=R^3=R^5=H$; $R^4$=OH; and B=—OCH$_2$C(O)NH(6-carbomethoxymethylmercaptopurine hydrazidyl);

Most preferred compounds according to the invention are the compounds of:

Formula IV, wherein R=ethyl; n=1; $R^2=R^{2a}=R^3=R^5=H$; $R^4$=OH; and D=—OCH$_2$C(O)—NH-benzyl;

Formula IV, wherein R=ethyl; n=1; $R^2=R^{2a}=R^3=R^5=H$; $R^4$=OH; and D=—OCH$_2$C(O)—N(3)-benzyl;

Formula IV, wherein R=ethyl; n=1; $R^2=R^{2a}=R^3=R^5$=H; $R^4$=OH; and D=—OCH$_2$C(O)—NH$_2$;

Formula IV, wherein R=ethyl; n=1; $R^2=R^{2a}=R^3=R^5$=H; $R^4$=OH; and D=—OCH$_2$C(O)—NH—CH$_3$;

Formula IV, wherein R=ethyl; n=1; $R^2=R^{2a}=R^3=R^5$=H; $R^4$=OH; and D=—OCH$_2$C(O)N(CH$_3$)$_2$;

Formula IV, wherein R=ethyl; n=1; $R^2=R^{2a}=R^3=R^5$=H; $R^4$=OH; and D=—OCH$_2$C(O)—NH-ethyl;

Formula IV, wherein R=ethyl; n=1; $R^2=R^{2a}=R^3=R^5$=H; $R^4$=OH; and D=-OCH$_2$C(O)N(3)-ethyl;

Formula IV, wherein R=ethyl; n=1; $R^2=R^{2a}=R^3=R^5$=H; $R^4$=OH; and D=—OCH$_2$C(O)—NH—CH$_2$CH$_2$CH$_3$;

Formula IV, wherein R=ethyl; n=1; $R^2=R^{2a}=R^3=R^5$=H; $R^4$=OH; and D=—OCH$_2$C(O)N(3)—CH$_2$CH$_2$CH$_3$;

Formula IV, wherein R=ethyl; n=1; $R^2=R^{2a}=R^3=R^5$=H; $R^4$=OH; and D=—OCH$_2$C(O)—NH—CH(CH$_3$)$_2$;

Formula IV, wherein R=ethyl; n=1; $R^2=R^{2a}=R^3=R^5$=H; $R^4$=OH; and D=—OCH$_2$C(O)N(C$_3$)—CH(CH$_3$)$_2$;

Formula IV, wherein R=ethyl; n=1; $R^2=R^{2a}=R^3=R^5$=H; $R^4$=OH; and D=—OCH$_2$C(O)—NH-cyclopropyl;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$_3$;

Formula IV, wherein R=ethyl; n=1; $R^2=R^{2a}=R^3=R^5$=H; $R^4$=OH; and D=—OCH$_2$C(O)N(3)—CH$_2$CH$_2$CH$_2$CH$_3$;

Formula IV, wherein R=ethyl; n=1; $R^2=R^{2a}=R^3=R^5$=H; $R^4$=OH; and D=—OCH$_2$C(O)—NH—CH$_2$CH(CH$_3$)$_2$;

Formula IV, wherein R=ethyl; n=1; $R^2=R^{2a}=R^3=R^5$=H; $R^4$=OH; and D=—OCH$_2$C(O)N(3)—CH$_2$CH(CH$_3$);

Formula IV, wherein R=ethyl; n=1; $R^2=R^{2a}=R^3=R^5$=H; $R^4$=OH; and B=—OCH$_2$C(O)—NHNH—CO—(4-pyridyl);

Formula IV, wherein R=ethyl; n=1; $R^2=R^{2a}=R^3=R^5$=H; $R^4$=OH; and D=—OCH$_2$C(O)—NH—cyclobutyl;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$^3$;

Formula IV, wherein R=ethyl; n=1; $R^2=R^{2a}=R^3=R^5$=H; $R^4$=OH; and D=—OCH$_2$C(O)N(3)—CH$_2$CH$_2$CH$_2$CH$_3$;

Formula IV, wherein R=ethyl; n=1; $R^2=R^{2a}=R^3=R^5$=H; $R^4$=OH; and D=—OCH$_2$C(O)—NH—CH$_2$CH$_2$CH(CH$_3$)$_2$;

Formula IV, wherein R=ethyl; n=1; $R^2=R^{2a}=R^3=R^5$=H; $R^4$=OH; and D=—OCH$_2$C(O)N(3)—CH$_2$CH$_2$CH(CH$_3$)$_2$;

Formula IV, wherein R=ethyl; n=1; $R^2=R^{2a}=R^3=R^5$=H; $R^4$=OH; and D=—OCH$_2$C(O)—NH—cyclopentyl;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$_2$CH$_3$;

Formula IV, wherein R=ethyl; n=1; $R^2=R^{2a}=R^3=R^5$=H; $R^4$=OH; and D=—OCH$_2$C(O)N(3)—CH$_2$CH$_2$CH$_2$CH$_2$CH$_3$;

Formula IV, wherein R=ethyl; n=1; $R^2=R^{2a}=R^3=R^5$=H; $R^4$=OH; and D=—OCH$_2$C(O)—NH—cyclohexyl;

Formula IV, wherein R=ethyl; n=1; $R^2=R^{2a}=R^3=R^5$=H; $R^4$=OH; and D=-OCH$_2$C(O)—NR$^6$R$^7$, where R$^6$ and R$^7$, taken together=—CH$_2$CH$_2$OCH$_2$CH$_2$—, thus forming a six-membered ring incorporating the nitrogen to which they are attached;

Formula IV, wherein R=ethyl; n=1; $R^2=R^{2a}=R^3=R^5$=H; $R^4$=OH; and B=—OCH$_2$C(O)NH(4-morpholinyl);

Formula IV, wherein R=ethyl; n=1; $R^2=R^{2a}=R^3=R^5$=H; $R^4$=OH; and D=—OCH$_2$C(O)—NH—CH$_2$CH$_2$OH;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$OH;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$_2$OH;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$_2$CH$_2$OH;

Formula IV, wherein R=ethyl; n=1; $R^2=R^{2a}=R^3=R^5$=H; $R^4$=OH; and D=—OCH$_2$C(O)—NH—CH$_2$CH$_2$NH$_2$;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$NH$_2$;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH$_2$NH$_2$;

Formula IV, wherein R=ethyl; n=1; $R^2=R^{2a}=R^3=R^5$=H; $R^4$=OH; and D=—OCH$_2$C(O)—NH—CH$_2$CH$_2$CH$_2$CH 2CH$_2$NH$_2$;

Formula IV, wherein R=ethyl; n=1; $R^2=R^{2a}=R^3=R^5$=H; $R^4$=OH; and D=—OCH$_2$C(O)—NH-CH$_2$CO$_2$CH$_2$Ph;

Formula IV, wherein R=ethyl; n=1; $R^2=R^{2a}=R^3=R^5$=H; $R^4$=OH; and D=—OCH$_2$C(O)—NH—CH$_2$CO$_2$H;

Formula IV, wherein R=ethyl; n=1; $R^2=R^{2a}=R^3=R^5$=H; $R^4$=OH; and D=—OCH$_2$C(O)—NH—CH$_2$CH$_2$CO$_2$CH$_2$Ph;

Formula IV, wherein R=ethyl; n=1; $R^2=R^{2a}=R^3=R^5$=H; $R^4$=OH; and D=—OCH$_2$C(O)—NH—CH$_2$CH$_2$CO$_2$H;

Formula IV, wherein R=ethyl; n=1; $R^2=R^{2a}=R^3=R^5$=H; $R^4$=OH; and D=—OCH$_2$C(O)—NH—(R)—CH(CH$_3$)CO$_2$H, and has an R configuration;

Formula IV, wherein R=ethyl; n=1; $R^2=R^{2a}=R^3=R^5$=H; $R^4$=OH; and D=—OCH$_2$C(O)—NH—(S)—CH(CH$_3$)CO$_2$H;

Formula IV, wherein R=ethyl; n=1; $R^2=R^{2a}=R^3=R^5$=H; $R^4$=OH; and D=—OCH$_2$C(O)—NH—3-phenyl-phenyl;

Formula IV, wherein R=ethyl; n=1; $R^2=R^{2a}=R^3=R^5$=H; $R^4$=OH; and D=—OCH$_2$C(O)N(CH$_2$CH$_2$OH)(3-phenylphenyl);

Formula IV, wherein R=ethyl; n=1; $R^2=R^{2a}=R^3=R^5$=H; $R^4$=OH; and D=—OCH$_2$C(O)N(CH$_2$(3-pyridyl))$_2$;

Formula IV, wherein R=ethyl; n=1; $R^2=R^{2a}=R^3=R^5$=H; $R^4$=OH; and D=—OCH$_2$C(O)—N(cyclohexyl)$_2$;

Formula IV, wherein R=ethyl; n=1; $R^2=R^{2a}=R^3=R^5$=H; $R^4$=OH; and D=—OCH$_2$C(O)—NH(4-thiomorpholinyl);

Formula IV, wherein R=ethyl; n=1; $R^2=R^{2a}=R^3=R^5$=H; $R^4$=OH; and D=—OCH$_2$C(O)NH—4-CF$_3$-phenyl);

Formula IV, wherein R=ethyl; n=1; $R^2=R^{2a}=R^3=R^5$=H; $R^4$=OH; and D=—OCH$_2$C(O)—NH(4-F-phenyl);

Formula IV, wherein R=ethyl; n=1; $R^2=R^{2a}=R^3=R^5$=H; $R^4$=OH; and D=—OCH$_2$C(O)—NH(4-(4-morpholino)-phenyl);

Formula IV, wherein R=ethyl; n=1; $R^2=R^{2a}=R^3=R^5$=H; $R^4$=OH; and D=—OCH$_2$C(O)—NH4-HO-phenyl);

Formula IV, wherein R=ethyl; n=1; $R^2=R^{2a}=R^3=R^5$=H; $R^4$=OH; and D=—OCH$_2$C(O)—NH—3-pyridyl;

Formula IV, wherein R=ethyl; n=1; $R^2=R^{2a}=R^3=R^5$=H; $R^4$=OH; and D=—OCH$_2$C(O)—NH—4-pyridyl;

Formula IV, wherein R=ethyl; n=1; $R^2=R^{2a}=R^3=R^5$=H; $R^4$=OH; and D=—OCH$_2$C(O)—NH—2-pyridyl;

Formula IV, wherein R=ethyl; n=1; $R^2=R^{2a}=R^3=R^5$=H; $R^4$=OH; and D=—OCH$_2$C(O)—N(3)—CH$_2$CH$_2$OH;

Formula IV, wherein R=ethyl; n=1; $R^2=R^{2a}=R^3=R^5$=H; $R^4$=OH; and D=—OCH$_2$C(O)—(L-prolinocarboxamide);

Formula IV, wherein R=ethyl; n=1; $R^2=R^{2a}=R^3$=RS=H; $R^4$=OH; and D=—OCH$_2$C(O)—(D-prolinocarboxamide);

Formula IV, wherein R=ethyl; n=1; $R^2=R^{2a}=R^3=R^5$=H; $R^4$=OH; and D=—OCH$_2$C(O)—(L-prolinol);

(Formula IV, wherein R=ethyl; n=1; $R^2=R^{2a}=R^{2a}=R^3$; =$R^5$=H; $R^4$=OH; and D=—OCH$_2$C(O)—(D-prolinol);

Formula IV, wherein R=ethyl; n=1; $R^2=R^{2a}=R^3=R^5$=H; $R^4$=OH; and D=—OCH$_2$C(O)—NH(3-(phenylethynyl)phenyl);

Formula IV, wherein R=ethyl; n=1; $R^2=R^{2a}=R^3=R^5$=H; $R^4$=OH; and D=—OCH$_2$C(O)—N(CH$_2$CH$_2$OH)(4-fluorophenyl);

Formula IV, wherein R=ethyl; n=1; $R^2=R^{2a}=R^3=R^5$=H; $R^4$=OH; and D=—OCH$_2$C(O)NR$^6$R$^7$, where R$^6$ and R$^7$, taken together, form the diradical, —CH$_2$CH$_2$—C(OCH$_2$CH$_2$O)CH$_2$CH$_2$—; Formula IV, wherein R=ethyl; n=1; R$^2$=R$^{2a}$=R$^3$=R$^5$=H; R$^4$=OH; and D=—OCH$_2$C(O)—NH(3-fluorophenyl);

Formula IV, wherein R=ethyl; n=1; R$^2$=R$^{2a}$=R$^3$=R$^5$=H; R$^4$=OH; and D=—OCH$_2$C(O)—NH(3-hydroxy-phenyl);

Formula IV, wherein R=ethyl; n=1; R$^2$=R$^{2a}$=R$^3$=R$^5$=H; R$^4$=OH; and D=—OCH$_2$C(O)NR$^6$R$^7$, where R$^6$ and R$^7$, taken together, form the diradical, —CH$_2$CH$_2$—NCH$_3$CH$_2$CH$_2$—;

Formula IV, wherein R=ethyl; n=1; R$^2$=R$^{2a}$=R$^3$=R$^5$=H; R$^4$=OH; and D=—OCH$_2$C(O)—NH {6-(1,4-benzodioxanyl)};

Formula IV, wherein R=ethyl; n=1; R$^2$=R$^{2a}$=R$^3$=R$^5$=H; R$^4$=OH; and D=—OCH$_2$C(O)—NH(3,4-methylenedioxyphenyl);

Formula IV, wherein R=ethyl; n-1; R$^2$=R$^{2a}$=R$^3$=R$^5$=H; R$^4$=OH; and D=—OCH$_2$C(O)—NH—1-naphthalenyl;

Formula IV, wherein R=ethyl; n=I; R$^2$=R$^{2a}$=R$^3$=R$^5$=H; R$^4$=OH; D=—OCH$_2$C(O)R$^{12}$; and R$^{12}$=NR$^6$R$^7$; where R$^6$ and R$^7$ taken together=—CH$_2$CH$_2$CH$_2$CH$_2$—, thus forming a five membered ring incorporating the nitrogen to which they are attached;

Formula IV, wherein R=ethyl; n=1; R$^2$=R$^{2a}$=R$^3$=R$^5$=H; R$^4$=OH; D=—OCH$_2$C(O)R$^{12}$; and R$^{12}$=NR$^6$R$^7$; where R$^6$ and R$^7$ taken together =-CH$_2$CH$_2$CH$_2$CH$_2$CH$_2$—, thus forming a six membered ring incorporating the nitrogen to which they are attached;

Formula IV, wherein R=ethyl; n=I; R$^2$=R$^{2a}$=R$^3$=R$^5$=H; R$^4$=OH; and D=—OCH$_2$—C(O)NH—CH$_2$CH$_2$C$_6$H$_5$;

Formula IV, wherein R=ethyl; n=1; R$^2$=R$^{2a}$=R$^3$=R$^5$=H; R$^4$=OH; and D=—OCH$_2$C(O)—N(3)—CH$_2$CH$_2$C$_6$H$_5$;

Formula IV, wherein R=ethyl; n=1; R$^2$=R$^{2a}$=R$^3$=R$^5$=H; R$^4$=OH; and D=—OCH$_2$—C(O)—N$_6$H$_5$;

Formula IV, wherein R=ethyl; n=1; R$^2$=R$^{2a}$=R$^3$=R$^5$=H; R$^4$=OH; and D=—OCH$_2$—C(O)—NH(CH$_2$)$_2$N(CH$_2$CH$_2$)$_2$O; Formula IV, wherein R=ethyl; n=1; R$^2$=R$^{2a}$=R$^3$=R$^5$=H; R$^4$=OH; and D=—OCH$_2$—C(O)—NH(CH$_2$)$_3$N(CH$_2$CH$_2$)$_2$O;

Formula IV, wherein R- ethyl; n=1; R$^2$=R$^{2a}$=R$^3$=R$^5$=H; R$^4$=OH; and D=—OCH$_2$—C(O)—NH(CH$_2$)$_2$N(CH$_3$)$_2$;

Formula IV, wherein R=ethyl; n=1; R$^2$=R$^{2a}$=R$^3$=R$^5$=H; R$^4$=OH; and D=—OCH$_2$—C(O)—NH(CH$_2$)$_3$N(CH$_3$)$_2$;

Formula IV, wherein R=ethyl; n=1; R$^2$=R$^{2a}$=R$^3$=R$^5$=H; R$^4$=OH; and D=—OCH$_2$—C(O)—(S)—NHCH(CH$_2$C$_6$H$_5$)CO$_2$CH$_2$Ph;

Formula IV, wherein R=ethyl; n=1; R$^2$=R$^{2a}$=R$^3$=R$^5$=H; R$^4$=OH; and D=—OCH$_2$—C(O)—(S)—NHCH(CH$_2$C$_6$H$_5$)CO$_2$H;

Formula IV, wherein R=ethyl; n=1; R$^2$=R$^{2a}$=R$^3$=R$^5$=H; R$^4$=OH; and D=—OCH$_2$—C(O)—(R)—NHCH(CH$_2$C$_6$H$_5$)CO$_2$CH$_2$Ph;

Formula IV, wherein R=ethyl; n=1; R$^2$=R$^{2a}$=R$^3$=R$^5$=H; R$^4$=OH; and D=—OCH$_2$—C(O)—(R)—NHCH(CH$_2$C$_6$H$_5$)CO$_2$H;

Formula IV, wherein R=ethyl; n=1; R$^2$=R$^{2a}$=R$^3$=R$^5$=H; R$^4$=OH; and D=—OCH$_2$—C(O)—HN(CH$_2$)$_2$SH;

Formula IV, wherein R=ethyl; n=1; R$^2$=R$^{2a}$=R$^3$=R$^5$=H; R$_4$=OH; and D=—OCH$_2$—C(O)—HN(CH$_2$)$_3$SH;

Formula IV, wherein R=ethyl; n=1; R$^2$=R$^{2a}$=R$^3$=R$^5$=H; R$^4$=OH; and D=—OCH$_2$C(O)—NH—2-naphthyl;

Formula IV, wherein R=ethyl; n=1; R$^2$=R$^{2a}$=R$^3$=R$^4$=R$^5$=H; and D=—OCH$_2$C(O)—NR$^6$R$^7$, where R$^6$ and R$^7$, taken together, are the diradical, —CH$_2$CH$_2$OCH$_2$CH$_2$—;

Formula IV, wherein R=ethyl; n=1; R$^2$=R$^{2a}$=R$^3$=R$^5$=H; R$^4$=OH; and D=—OCH$_2$C(O)—NH{4—(H$_2$NSO$_2$)-phenyl};

Formula IV, wherein R=ethyl; n=1; R$^2$=R$^{2a}$=R$^3$=R$^5$=H; R$^4$=OH; and D=—OCH$_2$C(O)NR$^6$R$^7$, where R$^6$ and R$^7$, taken together, form the diradical, —CH$_2$CH$_2$CH$_2$OH)CH$_2$CH$_2$—;

Formula IV, wherein R=ethyl; n=1; R$^2$=R$^{2a}$=R$^3$=R$^5$=H; R$^4$=OH; and D=—OCH$_2$C(O)—N(3)phenyl;

Formula IV, wherein R=ethyl; n=1; R$^2$=R$^{2a}$=R$^3$=R$^5$=H; R$^4$=OH; and D=—OCH$_2$C(O)—N(CH$_2$CH$_2$OH)$_2$;

Formula IV, wherein R=ethyl; n=1; R$^2$=R$^{2a}$=R$^3$=R$^5$=H; R$^4$=OH; and D=—OCH$_2$C(O)N(CH$_3$)CH$_2$CH$_2$CH$_2$N(CH$_3$)$_2$;

Formula IV, wherein R=ethyl; n=1; R$^2$=R$^{2a}$=R$^3$=R$^5$=H; R$^4$=OH; and D=—OCH$_2$C(O)—NH—CH(CH$_2$OH)$_2$;

Formula IV, wherein R=ethyl; n=1; R$^2$=R$^{2a}$=R$^3$=R$^5$=H; R$^4$=OH; and D=—OCH$_2$C(O)—NH{3-(CF$_3$)-phenyl};

Formula IV, wherein R=ethyl; n=1; R$^2$=R$^{2a}$=R$^3$=R$^5$=H; R$^4$=OH; and D=—OCH$_2$C(O)—N(CH$_2$CN)$_2$;

Formula IV, wherein R=ethyl; n=1; R$^2$=R$^{2a}$=R$^3$=R$^5$=H; R$^4$=OH; and D=—OCH$_2$C(O)NR$^6$R$^7$, where R$^6$ and R$^7$, taken together, form the diradical, —CH$_2$CH$_2$—;

Formula IV, wherein R=ethyl; n=1; R$^2$=R$^{2a}$=R$^3$=R$^5$=H; R$^4$=OH; and D=OCH$_2$—NH(CO)NR$^6$R$^7$; where R$^6$ and R$^7$, taken together, are the diradical, —CH$_2$CH$_2$OCH$_2$CH$_2$—;

Formula IV, wherein R=ethyl; n=1; R$^2$=R$^{2a}$=R$^3$=R$^5$=H; R$^4$=OH; and D=OCH$_2$—NH(CO)NH-phenyl;

Formula IV, wherein R=ethyl; n=1; R$^2$=R$^{2a}$=R$^3$=R$^5$=H; R$^4$=OH; and D=OCH$_2$—NH(CO)NH—CH$_2$CH$_2$OH;

Formula IV, wherein R=ethyl; n=1; R$^2$=R$^{2a}$=R$^3$=R$^5$=H; R$^4$=OH; and D=OCH$_2$C(O)—NR$^6$R$^7$, where R$^6$ and R$^7$, taken together, form the diradical, —CH$_2$CH$_2$SO$_2$CH$_2$CH$_2$—;

Formula IV, wherein R=ethyl; n=1; R$^2$=R$^{2a}$=R$^3$=R$^5$=H; R$^4$=OH; and D=OCH$_2$C(O)—NH—CH$_2$-(4-F-phenyl);

Formula IV, wherein R=ethyl; n=1; R$^2$=R$^{2a}$=R$^3$=R$^5$=H; R$^4$=OH; and D=OCH$_2$C(O)—NH(4-Cl-phenyl);

Formula IV, wherein R=ethyl; n=1; R$^2$=R$^{2a}$=R$^3$=R$^5$=H; R$^4$=OH; and D=OCH$_2$C(O)—NH(4-(OCH$_3$)-phenyl);

Formula IV, wherein R=ethyl; n=1; R$^2$=R$^{2a}$=R$^3$=R$^5$=H; R$^4$=OH; and D=OCH$_2$C(O)—NH(4—CH$_3$-phenyl);

Formula IV, wherein R=ethyl; n=1; R$^2$=R$^{2a}$=R$^3$=R$^5$=H; R$^4$=OH; and D=OCH$_2$C(O)NH(3,4-Cl$_2$-phenyl);

Formula IV, wherein R=ethyl; n=1; R$^2$=R$^{2a}$=R$^3$=R$^5$=H; R$^4$=OH; and D=OCH$_2$C(O)—NH(3-I-phenyl);

Formula IV, wherein R=ethyl; n=1; R$^2$=R$^{2a}$=R$^3$=H; R$^4$ and R$^5$, taken together, form a bond; and D=—OCH$_2$C(O){4-(morpholinyl)};

Formula IV, wherein R=ethyl; n=1; R$^2$=R$^3$=R$^5$=H; R$^{2a}$=R$^4$=OH; and D=OCH$_2$C(O)NH(3-fluoro-phenyl); and Formula IV: R=ethyl; n=1; R$^2$=R$^{2a}$=R$^3$=R$^5$=H; R$^4$=OH; D=—OCH$_2$C(O)NR$^6$R$^7$; R$^6$=-(CH$_2$)$_2$N(CH$_2$CH$_2$)$_2$O; R$^7$=—CH$_2$CH$_2$OH.

As used throughout this Specification and Claims, the following terms have the meanings specified:

"Acyl", as used herein, refers to an aryl or alkyl group, as defined below, appended to the remainder of the molecule via a carbonyl group. Examples include, but are not limited to, acetyl, pivaloyl, benzoyl, and the like.

"Acylamino" refers to an acyl group, as defined above, except that it is appended to the remainder of the molecule via an amino group. Examples include, but are not limited to, acetylamino, pivaloylamino, benzoylamino, and the like.

"Acylguanidino" refers to an acyl group, as defined above, except that it is attached to the remainder of the molecule via a nitrogen of a guanidino radical in one of three ways: HN(acyl)C(NH)NH— or H$_2$NC(NH)N(acyl)- or (acyl)NC(NH$_2$)HN—.

"Alkenyl" refers to straight- or branched-chain groups of a specified number of carbon atoms containing at least one carbon-carbon double bond including, but not limited to ethenyl, 1-propenyl, 2-propenyl, 2-methyl-1-propenyl, 1-butenyl, 2-butenyl, and the like.

"Alkoxy", "alkylether" and "loweralkoxy" refer to an alkyl group, as defined below, attached to the remainder of the molecule through an oxygen atom. Examples include, but are not limited to, methoxy, ethoxy, isopropoxy, n-butoxy, sec-butoxy, isobutoxy, tert-butoxy and the like.

"Alkoxycarbonyl" refers to an alkoxy group, as defined above, except that it is attached to the remainder of the molecule via a carbonyl group. Examples include, but are not limited to, methyloxycarbonyl, ethyloxycarbonyl, tert-butyloxycarbonyl, cyclohexyloxycarbonyl, and the like.

"Alkoxycarbonylamino" refers to an alkoxycarbonyl group, as defined above, except that it is attached to the remainder of the molecule via an amino group. Examples include, but are not limited to, methyloxy-carbonylamino, tert-butyloxycarbonylamino, and the like.

"Alkoxycarbonylguanidino" refers to an alkoxycarbonyl group, as defined above, except that it is attached to .the remainder of the molecule via a nitrogen of a guanidino radical in one of three ways: HN(alkoxycarbonyl)C(NH$_2$)HN—, H$_2$NC(NH)N(alkoxycarbonyl)- or (alkoxycarbonyl)NC(NH$_2$)HN—.

"Alkyl" refers to a straight- or branched-chain group of a specified number of carbon atoms including, as appropriate, but not necessarily limited to, methyl, ethyl, n-propyl, isopropyl, n-butyl, sec-butyl, isobutyl, tert-butyl, and the like.

"Alkylamino" refers to a group having the structure —NH—(alkyl), where the alkyl portion is as defined above, including, for example, methylamino, ethylamino, isopropylamino, and the like.

"Alkylsulfonyl" refers to an alkyl group, as defined above, except that it is attached to the remainder of the molecule via a sulfur dioxide diradical. Examples include but are not limited to, methanesulfonyl, camphorsulfonyl and the like.

"Alkylthioether" and "thioalkoxy" refer to an alkyl group, as previously defined, except that it is attached to the remainder of the molecule via a sulfur atom. Examples include, but are not limited to, thiomethoxy, thioethoxy, thioisopropoxy, n-thiobutoxy, sec-thiobutoxy, isothiobutoxy, tert-thiobutoxy, and the like.

"Alkynyl" refers to straight- or branched-chain groups of a specified number of carbon atoms containing at least one carbon-carbon triple bond, including, but not limited to acetylenyl, propargyl, and the like.

"Amidoalkyl" refers to a group having the structure —NR$^{101}$C(O)R$^{102}$ appended to the remainder of the molecule via an alkyl group, as previously defined, wherein R$^{101}$ and R$^{102}$ are independently hydrogen, alkyl, aryl, arylalkyl, or halosubstituted alkyl, or R$^{101}$ and R$^{102}$, taken together, may optionally be —(CH$_2$)$_{aa}$—, where aa is an integer of from 2-to-6.

"Aminoalkyl" refers to a group having the structure —NR$^{103}$R$^{104}$ appended to the remainder of the molecule via an alkyl group, as previously defined, wherein R$^{103}$ and R$^{104}$ are independently hydrogen, alkyl, qualified-aryl or qualified-arylalkyl, or R$^{103}$ and R$^{104}$, taken together, may optionally be —(CH$_2$)$_{bb}$—, where bb is an integer of from 2-to-6.

"Aryl", as used herein, refers to mono-, di-, tri- or tetracyclic aromatic groups, charged or uncharged, the rings of which are comprised of from 3-to-7 carbon atoms. Examples of aryl include, but are not limited to, phenyl, 1- or 2-naphthyl, azulenyl, fluorenyl, (1, 2)-dihydronaphthyl, (1,2,3,4)-tetrahydronaphthyl, indenyl, indanyl and the like, which are unsubstituted or substituted with from one, two or three independently-selected substituents, R$^{301}$, as defined above.

"Arylalkoxy" and "arylalkylether" refer to an arylalkyl group, as defined below, attached to the parent molecular moiety through an oxygen atom. Examples include, but are not limited to, benzyloxy, 2-phenethyloxy, 1-naphthylmethyloxy, and the like.

"Arylalkoxycarbonyl" refers to an arylalkoxy group, as defined above, except that it is attached to the remainder of the molecule via a carbonyl group. Examples include, but are not limited to, benzyloxycarbonyl, 9-fluorenylmethyloxycarbonyl, and the like.

"Arylalkoxycarbonylamino" refers to an arylalkoxycarbonyl group, as defined above, except that it is attached to the remainder of the molecule via an amino group. Examples include, but are not limited to, benzyloxycarbonylamino, 9-fluorenylmethyloxycarbonylamino, and the like.

"Arylalkoxycarbonylguanidino" refers to an aryla! koxycarbonyl group, as defined above, except that it is attached to the remainder of the molecule via a nitrogen of a guanidino radical in one of three ways: HN(arylalkoxycarbonyl)C(NH)HN—, H$_2$NC(NH)N(arylalkoxycarbonyl)- or (arylalkoxycarbonyl)NC(NH$_2$)HN—.

"Arylalkyl" refers to an aryl group, as previously defined, except that it is attached to the remainder of the molecule via an alkyl group.

"Arylalkylamino" refers to a group having the structure —NH—(arylalkyl), where the arylalkyl portion is as previously defined, except that it is attached to the remainder of the molecule via an amino group. Examples include benzylamino, 1-phenylethylamino, and the like.

"Arylalkylthioether" and "thioarylalkoxy" refer to an arylalkyl group, as previously defined, except that it is attached to the remainder of the molecule via a sulfur atom.

"Arylamino" refers to an aryl group, as defined above, except that it is attached to the remainder of the molecule via an amino group. Examples include, but are not limited to, anilino, naphthylamino, and the like.

"Arylether" and "aryloxy" refer to an aryl group, as previously defined, attached to the parent molecular moiety through an oxygen atom. Examples include, but are not limited to, phenoxy, 1-naphthoxy, 2-naphthoxy, and the like.

"Aryloxycarbonyl" refers to an aryloxy group, as defined above, except that it is attached to the remainder of the molecule via a carbonyl group. Examples include, but are not limited to, phenyloxycarbonyl, and the like.

"Aryloxycarbonylamino" refers to an aryloxycarbonyl group, as defined above, except that it is attached to the remainder of the molecule via an amino group. Examples include, but are not limited to, phenyloxycarbonylamino, and the like.

"Aryloxycarbonylguanidino" refers to an aryloxycarbonyl group, as defined above, except that it is attached to the remainder of the molecule via a nitrogen of a guanidino moiety in one of three ways: HN(aryloxycarbonyl)C(NH)HN—, H$_2$NC(NH)N(aryloxycarbonyl)— or (aryloxycarbonyl)NC(NH$_2$)HN—.

"Arylsulfonyl" refers to an aryl group, as defined above, except that it is attached to the remainder of the molecule via a sulfur dioxide group. Examples include, but are not limited to p-toluenesulfonyl, benzenesulfonyl, and the like.

"Arylsulfonylguanidino" refers to an arylsulfonyl group, as defined above, except that it is attached to the remainder of the molecule via a guanidino group in one of three ways: HN(arylsulfonyl)C(NH)HN— or H₂NC(NH)N(arylsulfonyl)— or (arylsulfonyl)NC(NH₂)HN—.

"Arylthioether" and "thioaryloxy" refer to an aryl group, as defined above, except that it is attached to the remainder of the molecule via a sulfur atom.

"Biaryl" refers to a mod-aryl group, as defined below, which carries as a substituent another independently selected mod-aryl group, such that the two are connected by a single carbon-carbon bond.

"Carboxamido" refers to an amino group attached to the remainder of the molecule via a carbonyl group, and having the formula H₂NC(O)—.

"Carboxyalkyl" refers to a carboxyl group, —CO₂H, appended to the remainder of the molecule via an alkyl group, as previously defined.

"Counterion", as used herein, refers to a positively-charged atom or molecular species, with a net charge of +1, which includes, but is not limited to Li⁺, Na⁺, Ca(O-C(O)CH₃)⁺, MgCl⁺, K⁺, NH₄⁺, (n-butyl)₄N⁺, and the like.

"Cycloalkenyl" refers to cyclic groups of 5-lo-10 carbons possessing one or more carbon-carbon double bonds including, but not limited to, cyclopentenyl, cyclohexenyl, 1,3,3-trimethylcyclohexenyl, and the like, in which the point of attachment may occur at any available valency on the carbocylic ring.

"Cycloalkyl" refers to saturated cyclic groups of 3-to-8 carbons including, but not limited to, cyclopropyl, cyclobutyl, cyclopentyl, cyclohexyl, and the like.

"Cycloalkylalkenyl" refers to cycloalkyl, as defined above, except that it is attached to the remainder of the molecule via an alkenyl group, as defined above.

"Cycloalkylalkyl" refers to a cycloalkyl group, as defined above, except that it is attached to the remainder of the molecule via an alkyl group. Examples include, but are not limited to, cyclohexyhnethyl, cyclohexylethyl, and the like.

"Cycloalkylalkynyl" refers to cycloalkyl, as defined above, except that it is attached to the remainder of the molecule via an alkynyl group, as defined above.

"Guanidino" refers to a group of the structure —NR¹⁰⁵C(=NR¹⁰⁶)NHR¹⁰⁷ or —NC(NHR¹⁰⁶)NHR¹⁰⁷, wherein R¹⁰⁵, R¹⁰⁶, and R¹⁰⁷ are independently selected from hydrogen, (C₁-to-C₆-alkyl), mod-Het-, as defined below, mot-heterocyclic, as defined below, aminoalkyl, as defined above, and mod-aryl, as defined below, or alternatively, R¹⁰⁶, and R¹⁰⁷, taken together, may optionally be —(CH₂)_cc—, where cc is an integer of from 2-to-6.

"Halo" and "halogen" refer to an atom selected from fluorine, chlorine, bromine and iodine.

"Het-", as used herein, refers to any aromatic 5-, 6- or 7-membered monocyclic ring or a bi- or tri-cyclic group comprising fused five- or six-membered rings having ring carbon atoms and between one and three heteroatoms independently selected from oxygen, sulfur and nitrogen, wherein (i) each 5-membered ring has 2 double bonds and each 6- or 7-membered ring has 3 double bonds, (ii) the nitrogen and sulfur heteroatoms as well as the carbon atoms may optionally be oxidized, (iii) the nitrogen heteroatom may optionally be quaternized, (iv) any of these rings may be fused to a benzene ring, and (v) any carbon or heteroatom with suitable valence may bear a substituent, R³⁰¹, as defined above. Any two adjacent R³⁰¹ substituents in a di-, tri-, tetra- or penta-substituted Het group may form a 5-, 6- or 7-membered ring consisting of carbon atoms and zero, one or two heteroatoms independently selected from the group consisting of —O—, —S(O)ₛ—, where s is as defined above, and —NR⁸—, where R⁸ is as defined above. Het groups include, but are not limited to, pyrrolyl, pyrazolyl, cytosinyl, thiocytosinyl, imidazolyl, pyridyl, pyrazinyl, pyrimidinyl, pyridazinyl, xanthenyl, xanthonyl, xanthopterinyl, oxazolyl, thiouracilyl, isoxazolyl, indolyl, quinolinyl, uracilyl, urazolyl, uricyl, thiazolyl, isothiazolyl, isoquinolinyl, thyminyl, benzimidazolyl, benzothiazolyl, benzoxazolyl, furyl, thienyl, benzothienyl, and the like.

"Heterocyclic" as used herein, except where otherwise specified, refers to any non-aromatic 5-, 6- or 7-membered monocyclic ring or a bi- or tri-cyclic group comprising fused five- or six-membered rings, having ring carbon atoms and between one-and-three heteroatoms independently selected from oxygen, sulfur and nitrogen, wherein (i) each 5-membered ring has 0 or 1 double bond and each 6-membered ring has 0 to 2 double bonds, (ii) the nitrogen and sulfur heteroatoms as well as the carbon atoms may optionally be oxidized, (iii) the nitrogen heteroatom may optionally be quaternized, (iv) any of these rings may be fused to a benzene ring, and (v) any carbon or heteroatom with suitable valence may bear a substituent, R³⁰¹, as defined above. Any two adjacent R³⁰¹ substituents in a di-, tri-, tetra- or penta-substituted heterocyclic group may form a 5-, 6- or 7-membered ring consisting of ring carbon atoms and zero, one or two heteroatoms independently selected from the group consisting of —O—, —S(O)ₛ—, where s is as defined above, and —NR⁸—, where R⁸ is as defined above. Representative heterocycles include, but are not limited to, aziridinyl, thiomorpholine, thiomorpholine-oxide, thiomorpholine dioxide, and pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, and isothiazolidinyl, and the like.

"Heterocyclic alkyl" refers to a heterocyclic group, as defined above, except that it is attached to the remainder of the molecule via an alkyl group, as previously defined.

"Heterocyclic alkylether" refers to a heterocyclic alkyl moiety, as defined above, except that it is attached to the remainder of the molecule via an oxygen atom.

"Heterocyclic alkenyl" refers to a heterocyclic group, as defined above, except that it is attached to the remainder of the molecule via an alkenyl group, as previously defined.

"Heterocyclic alkylthioether" refers to a heterocyclic alkyl moiety, as defined above, except that it is attached to the remainder of the molecule via a sulfur atom.

"Heterocyclic alkynyl" refers to a heterocyclic group, as defined above, except that it is attached to the remainder of the molecule via an alkynyl group, as previously defined.

"Heterocyclic ether" refers to a heterocyclic moiety, as defined above, except that it is attached to the remainder of the molecule via an oxygen atom.

"Heterocyclic thioether" refers to a heterocyclic moiety, as defined above, except that it is attached to the remainder of the molecule via a sulfur atom.

"Hydroxyalkyl" refers to an —OH appended to an alkyl group, as defined above.

"Hydroxy-protecting group" refers to those groups which are known in the art to protect a hydroxyl group against undesirable reactions during synthetic procedures and to be selectively removable including, but not limited to, methylthiomethyl, tert-butyldimethylsilyl, tert-butyldiphenylsilyl, acyl substituted with an aryl group, where acyl and aryl are defined above, and the like.

"Leaving group" refers to an alkyl-, alkenyl-, or aryl-substituent, where alkyl, alkenyl, and aryl are as defined above, which in a reaction becomes cleaved to either produce a site of unsaturation or to introduce another substituent.

"Mod-aryl", as used herein, refers to an aryl group, as defined above, except that the aryl group is unsubstituted or substituted with from one-to-three independently selected substituents, $R^{302}$, rather than $R^{301}$, where $R^{302}$ is as defined above. Any two adjacent $R^{302}$ substituents in a di- or tri-substituted mod-aryl group may form a 5-, 6- or 7-membered carbocyclic ring or 5-, 6- or 7-membered heterocyclic-ring where the ring atoms are carbon atoms and one or two heteroatoms independently selected from the group consisting of—O—, —S(O)$_s$—, where s is as defined above, and —NR$^{18}$—, where R$^{18}$ is as defined above.

"Mod-$C_1$-to-$C_{10}$-alkyl", as used herein, refers to a-($C_1$-to-$C_{10}$-alkyl) group substituted with from one-to-six radicals selected from:
(1) —$R^8$, as defined above;
(2) —(CH$_2$)$_m$OR$^8$, where m and R$^8$ are as defined above;
(3) —S(O)$_s$R$^8$, where s and R$^8$ are as defined above;
(4) —S(O)$_t$NR$^8$R$_9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, as defined above;
(9) —$R^{400}$, as defined above;
(10) —aryl; and
(11) —Het.

"Mod-$C_3$-to-$C_{10}$-alkenyl", as used herein, refers to a —($C_3$-to-$C_{10}$-alkenyl) group substituted with from one-to-six radicals selected from:
(1) —$R^8$, where R$^8$ is as defined above;
(2) —(CH$_2$)$_m$OR$^8$, where m and R$^8$ are as defined above;
(3) —S(O)$_s$R$^8$, where s and R$^8$ are as defined above;
(4) —S(O)$_t$NR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, where R$^{399}$ is as defined above;
(9) —$R^{400}$, where R$^{400}$ is as defined above;
(10) -aryl; and
(11) -Het.

"Mod-$C_3$-to-$C_{10}$-alkynyl", as used herein, refers to a —($C_3$-to-$C_{10}$-alkynyl) group substituted with from one-to-six radicals selected from:
(1) —$R^8$, where R$^8$ is as defined above;
(2) —(CH$_2$)$_m$OR$^8$, where m and R$^8$ are as defined above;
(3) —S(O)$_s$R$^8$, where s and R$^8$ are as defined above;
(4) —S(O)tNR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, where R$^{399}$ is as defined above;
(9) —$R^{400}$, where R$^{400}$ is as defined above;
(10) -aryl; and
(11) -Het.

"Mod-cyclo-$C_3$-to-$C_{10}$-alkyl", as used herein, refers to a —(cyclo-$C_3$-to-$C_{10}$-alkyl) group substituted with from one-to-six radicals selected from:
(1) —$R^8$, where R$^8$ is as defined above;
(2) —(CH$_2$)$_m$OR$^8$, where m and R$^8$ are as defined above;
(3) —S(O)$_s$R$^8$, where s and R$^8$ are as defined above;
(4) —S(O)$_t$NR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, where R$^{399}$ is as defined above;
(9) —$R^{400}$, where R$^{400}$ is as defined above;
(10) —aryl; and
(11) —Het.

"Mod-cyclo-$C_4$-to-$C_{10}$-alkenyl", as used herein, refers to a —(cyclo-$C_4$-to-$C_{10}$alkenyl) group substituted with from one-to-six radicals selected from:
(1) —$R^8$, where R$^8$ is as defined above;
(2) —(CH$_2$)$_m$OR$^8$, where m and R$^8$ are as defined above;
(3) —S(O)$_s$R$^8$, where s and R$^8$ are as defined above;
(4) —S (O)$_t$NR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, where R$^{399}$ is as defined above;
(9) —$R^{400}$, where R$^{400}$ is as defined above;
(10) —aryl; and
(11) —Het.

"Mod-bicyclo-$C_6$-to-$C_{10}$-alkyl", as used herein, refers to a-(bicyclo-$C_6$-to-$C_{10}$-alkyl) group substituted with from one-to-six radicals selected from:
(1) -$R^8$, where R$^8$ is as defined above;
(2) —(CH$_2$)$_m$OR$^8$, where m and R$^8$ are as defined above;
(3) —S(O)$_s$R$^8$, where s and R$^8$ are as defined above;
(4) —S(O)$_t$NR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, where R$^{399}$ is as defined above;
(9) —$R^{400}$, where R$^{400}$ is as defined above;
(10) —aryl; and
(11) —Het.

"Mod-bicyclo-$C_6$-to-$C_{10}$-alkenyl", as used herein, refers to a -(bicyclo-$C_6$-to-C10alkenyl) group substituted with from one-to-six radicals selected from:
(1) —$R^8$, as defined above;
(2) —(CH$_2$)$_m$OR$^8$, where m and R$^8$ are as defined above;
(3) —S(O)$_s$R$^8$, where s and R$^8$ are as defined above;
(4) —S(O)$_t$NR$^8$R$^9$, where t and NR$^8$R$^9$ are as defined above;
(5) —(CH$_2$)$_m$NR$^8$R$^9$, where m and NR$^8$R$^9$ are as defined above;
(6) —SO$_3$H;
(7) =NOR$^8$, where R$^8$ is as defined above;
(8) —$R^{399}$, is as defined above;
(9) —$R^{400}$, is as defined above;
(10) —aryl; and
(11) —Het.

"Mod-Het-", as used herein, refers to a Het group, as defined above, except that the Het group may bear one or more substituents $R^{302}$, rather than $R^{301}$, where $R^{302}$ is as defined above or any two adjacent $R^{302}$ substituents in a di-, tri-, tetra- or penta-substituted mod-Het group may form a 5-, 6- or 7-membered ring consisting of ring carbon atoms and zero, one or two ring heteroatoms independently selected from the group consisting of —O—, —S(O)$_s$—, where s is as defined above, and —NR$^{18}$—, where R$^{18}$ is as defined above.

"Mod-heterocyclic" as used herein, refers to a heterocyclic group, as defined above, except that the heterocyclic group may bear one or more substituents $R^{302}$, rather than $R^{301}$, where $R^{302}$ is as defined above or any two adjacent $R^{302}$ substituents in a di-, tri-; tetra- or penta-substituted mod-heterocylic group may form a 5-, 6- or 7-membered ring consisting of carbon atoms and zero, one or two heteroatoms independently selected from the group consisting of —O—,—S(O)$_s$—, where s is as defined above, and —NR$^{18}$—, where R$^{18}$ is as defined above.

"Monoalkylamino" and "dialkylamino" refer respectively to one and two alkyl groups, as defined above, except that they are appended to the remainder of the molecule via an amino group. Examples include, but are not limited to, methylamino, isopropylamino, dimethylamino, N,N-methylisopropylamino, and the like.

"Monocycloalkylamino" and "dicycloalkylamino" refer respectively to one and two cycloalkyl groups, as defined above, except that they are appended to the remainder of the molecule via an amino group. Examples include, but are not limited to, cyclohexylamino, bis-(cyclohexyl)amino, and the like.

"Mono-halogenated alkyl", "di-halogenated alkyl" or "tri-halogenated alkyl" refer to alkyl groups, as defined above, of specified and compatible length, respectively substituted with one, two, or three halogen atoms, as defined above.

"N-alkylcarboxamido" refers to an alkylamino group, as defined above, except that it is appended to the remainder of the molecule via a carbonyl group and has the formula HN(alkyl)C(O)—.

"N-arylcarboxamido" refers to an arylamino group, as defined above, except that it is appended to the remainder of the molecule via a carbonyl group and having the formula HN(aryl)C(O)—.

"Naturally occuring amino acid" and "standard amino acid" refer to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"N,N-dialkylcarboxamido" refers to dialkylamino group, defined above, except that it is appended to the remainder of the molecule via a carbonyl group and has the formula N(alkyl)(alkyl')C(O)—.

"N,N-diarylcarboxamido" refers to two independently selected aryl groups, as defined above, except that they are appended to the remainder of the molecule via a =NC(O)— group, exemplified by the formula N(aryl)(aryl)C(O)—.

"N-terminal protecting group" refers to those groups known in the art to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), benzyloxycarbonyl (Cbz), benzoyl groups, and the like. Other such groups are described by Gross, E. and Meienhofer, J. in *The Peptides*, Volume 3; Academic Press, 1981.

"Oxo" refers to an oxygen atom forming a carbonyl group.

"Per-halogenated alkyl" refers to alkyl groups, as defined above, of specified length, substituted with halogen atoms, as defined above, at every available valency.

"Qualified-aryl" as used herein refers to substituted and unsubstituted carbocyclic aromatic groups including, but not limited to, phenyl, 1- or 2-naphthyl, fluorenyl, (1,2)-dihydronaphthyl, (1,2,3,4)-tetrahydronaphthyl, indenyl, indanyl and the like, optionally substituted with 1, 2 or 3 substituents independently selected from halo, nitro, cyano, —($C_1$-to-$C_{10}$-alkyl), alkoxy and halosubstituted alkyl.

"Qualified-arylalkyl" refers to a qualified-aryl group, as previously defined, attached to the remainder of the molecule via an alkyl group.

"Sub-$C_1$-to-$C_{10}$-alkyl", as used herein, refers to a -($C_1$-to-$C_{10}$-alkyl) substituted with from one-to-six radicals independently selected from the group consisting of:

(a) $R^6$, where $R^6$ is as defined above;
(b) —$(CH_2)_m OR^6$, where m and $R^6$ are as defined above;
(c) —$NR^6 R^7$, where $NR^6 R^7$ is as defined above;
(d) —$C(O)OR^6$, where $R^6$ is as defined above;
(e) —$SO_3 H$;
(f) —$S(O)_s R^6$, where s and $R^6$ are as defined above;
(g) —$S(O)_t NR^6 R^7$, where t and $NR^6 R^7$ are as defined above;
(h) =$NOR^6$, where $R^6$ is as defined above;
(i) —$R^{399}$, where $R^{399}$ is as defined above;
(j) —$R^{400}$, where $R^{400}$ is as defined above;
(k) —aryl, and
(l) —Het.

"Sub-cyclo-$C_3$-to-$C_{10}$-alkyl", as used herein, refers to a -(cyclo-$C_3$-to-$C_{10}$-alkyl) substituted with from one-to-six radicals independently selected from the group consisting of:

(a) $R^6$, where $R^6$ is as defined above;
(b) —$(CH_2)_m OR^6$, where m and $R^6$ are as defined above;
(c) —$NR^6 R^7$, where $NR^6 R^7$ is as defined above;
(d) —$C(O)OR^6$, where $R^6$ is as defined above;
(e) —$SO_3 H$;
(f) —$S(O)_s R^6$, where s and $R^6$ are as defined above;
(g) —$S(O)_t NR^6 R^7$, where t and $NR^6 R^7$ are as defined above;
(h) =$NOR^6$, where $R^6$ is as defined above;
(i) —$R^{399}$, where $R^{399}$ is as defined above;
(j) —$R^{400}$, where $R^{400}$ is as defined above;
(k) —aryl, and
(l) —Het.

"Sub-cyclo-$C_3$-to-$C_{10}$-alkyl-$C_1$-to-$C_3$-alkyl", as used herein, refers to a —(cyclo-$C_3$-to-$C_{10}$-alkyl-$C_1$-to-$C_3$-alkyl) substituted with from one-to-six radicals independently selected from the group consisting of:

(a) $R^6$, where $R^6$ is as defined above;
(b) —$(CH_2)_m OR^6$, where m and $R^6$ are as defined above;
(c) —$NR^6 R^7$, where $NR^6 R^7$ are as defined above;
(d) —$C(O)OR^6$, where $R^6$ is as defined above;
(e) —$SO_3 H$;
(f) —$S(O)_s R^6$, where s and $R^6$ are as defined above;
(g) —$S(O)_t NR^6 R^7$, where t and $NR^6 R^7$ are as defined above;
(h) =$NOR^6$, where $R^6$ is as defined above;
(i) —$R^{399}$, where $R^{399}$ is as defined above;
(j) —$R^{400}$, where $R^{400}$ is as defined above;
(k) —aryl, and
(l) —Het.

"Sub-$C_3$-to-$C_{10}$-alkenyl", as used herein, refers to a —($C_3$-to-$C_{10}$-alkenyl) substituted with from one-to-six radicals independently selected from the group consisting of:

(a) $R^6$, where $R^6$ is as defined above;
(b) —$(CH_2)_m OR^6$, where m and $R^6$ are as defined above;
(c) —$NR^6 R^7$, where $NR^6 R^7$ are as defined above;
(d) —$C(O)OR^6$, where $R^6$ is as defined above;
(e) —$SO_3 H$;
(f) —$S(O)_s R^6$, where s and $R^6$ are as defined above;
(g) —$S(O)_t NR^6 R^7$, where t and $NR^6 R^7$ are as defined above;
(h) =$NOR^6$, where $R^6$ is as defined above;
(i) —$R^{399}$, where $R^{399}$ is as defined above;
(j) —$R^{400}$, where $R^{400}$ is as defined above;
(k) —aryl, and
(l) —Het.

"Sub-cyclo-$C_4$-to-$C_{10}$-alkenyl", as used herein, refers to a —(cyclo-$C_4$-to-$C_{10}$-alkenyl) substituted with from one-to-six radicals independently selected from the group consisting of:

(a) $R^6$, where $R^6$ is as defined above;
(b) —$(CH_2)_m OR^6$, where m and $R^6$ are as defined above;
(c) —$NR^6 R^7$, where $NR^6 R^7$ are as defined above;
(d) —$C(O)OR^6$, where $R^6$ is as defined above;

(e) —SO$_3$H;
(f) —S(O)$_s$R$^6$, where s and R$^6$ are as defined above;
(g) —S(O)$_t$NR$^6$R$^7$, where t and NR$^6$R$^7$ are as defined above;
(h) =NOR$^6$, where R$^6$ is as defined above;
(i) —R$^{399}$, where R$^{399}$ is as defined above;
(j) —R$^{400}$, where R$^{400}$ is as defined above;
(k) —aryl, and
(l) —Het.

"Sub-cyclo-C$_6$-to-C$_{10}$-alkyl-C$_3$–C$_5$-alkenyl", as used herein, refers to a -(cyclo-C$_6$-to-C$_{10}$-alkyl-C$_3$–C$_5$-alkenyl) substituted with from one-to-six radicals independently selected from the group consisting of:
(a) R$^6$, where R$^6$ is as defined above;
(b) —(CH$_2$)$_m$OR$^6$, where m and R$^6$ are as defined above;
(c) —NR$^6$R$^7$, where NR$^6$R$^7$ are as defined above;
(d) —C(O)OR$^6$, where R$^6$ is as defined above;
(e) —SO$_3$H;
(f) —S(O)$_s$R$^6$, where s and R$^6$ are as defined above;
(g) —S(O)$_t$NR$^6$R$^7$, where t and NR$^6$R$^7$ are as defined above;
(h) =NOR$^6$, where R$^6$ is as defined above;
(i) —R$^{399}$, where R$^{399}$ is as defined above;
(j) —R$^{400}$, where R$^{400}$ is as defined above;
(k) —aryl, and
(l) —Het.

"Sub-C$_3$-to-C$_{10}$-alkynyl", as used herein, refers to a —(C$_3$-to-C$_{10}$-alkynyl) substituted with from one-to-six radicals independently selected from the group consisting of:
(a) R$^6$, as defined above;
(b) —(CH$_2$)$_m$OR$^6$, where m and R$^6$ are as defined above;
(c) —NR$^6$R$^7$, as defined above;
(d) —C(O)OR$^6$, where R$^6$ is as defined above;
(e) —SO$_3$H;
(f) —S(O)$_s$R$^6$, where s and R$^6$ are as defined above;
(g) —S(O)$_t$NR$^6$R$^7$, where t and NR$^6$R$^7$ are as defined above;
(h) =NOR$^6$, where R$^6$ is as defined above;
(i) —R$^{399}$, as defined above;
(j) —R$^{400}$, as defined above;
(k) —aryl, and
(l) -Het.

"Sub-cyclo-C$_6$-to-C$_{10}$-alkyl-C$_3$–C$_5$-alkynyl", as used herein, refers to a —(cyclo-C$_6$-to-C$_{10}$-alkyl-C$_3$–C$_5$-alkynyl) substituted with from one-to-six radicals independently selected from the group consisting of:
(a) R$^6$, as defined above;
(b) —(CH$_2$)$_m$OR$^6$, where m and R$^6$ are as defined above;
(c) —NR$^6$R$^7$, as defined above;
(d) —C(O)OR$^6$, where R$^6$ is as defined above;
(e) —SO$_3$H;
(f) —S(O)$_s$R$^6$, where s and R$^6$ are as defined above;
(g) —S(O)$_t$NR$^6$R$^7$, where t and NR$^6$R$^7$ are as defined above;
(h) =NOR$^6$, where R$^6$ is as defined above;
(i) —R$^{399}$, is as defined above;
(j) —R$^{400}$, is as defined above;
(k) —aryl, and
(l) —Het.

"Sub-bicyclo-C$_6$-to-C$_{10}$-alkyl", as used herein, refers to a -(bicyclo-C$_6$-to-C$_{10}$-alkyl) substituted with from one-to-six radicals independently selected from the group consisting of:
(a) R$^6$, as defined above;
(b) —(CH$_2$)$_m$OR$^6$, where m and R$^6$ are as defined above;
(c) —NR$^6$R$^7$, as defined above;
(d) —C(O)OR$^6$, where R$^6$ is as defined above;
(e) —SO$_3$H;
(f) —S(O)$_s$R6, where s and R$^6$ are as defined above;
(g) —S(O)$_t$NR$^6$R$^7$, where t and NR$^6$R$^7$ are as defined above;
(h) =NOR$^6$, where R$^6$ is as defined above;
(i) —R$^{399}$, where R$^{399}$ is as defined above;
(j) —R$^{400}$, where R$^{400}$ is as defined above;
(k) —aryl, and
(l) —Het.

"Sub-bicyclo-C$_6$-to-C$_{10}$-alkenyl", as used herein, refers to a -(bicyclo-C$_6$-to-C$_{10}$alkenyl) substituted with from one-to-six radicals independently selected from the group consisting of:
(a) R$^6$, as defined above;
(b) —(CH$_2$)$_m$OR$^6$, where m and R$^6$ are as defined above;
(c) —NR$^6$R$^7$, as defined above;
(d) —C(O)OR$^6$, where R$^6$ is as defined above;
(e) —SO$_3$H;
(f) —S(O)$_s$R$^6$, where s and R$^6$ are as defined above;
(g) —S(O)$_t$NR$^6$R$^7$, where t and NR$^6$R$^7$ are as defined above;
(h) =NOR$^6$, where R$^6$ is as defined above:
(i) —R$^{399}$, is as defined above;
(j) —R$^{400}$, is as defined above;
(k) —aryl, and
(l) —Het.

"Substituted-bicyclo-C$_6$-to-C$_{10}$-alkenyl ", as used herein, refers to a —(bicyclo-C$_6$-to-C$_{10}$-alkenyl) group substituted with from one-to-three radicals selected from: halogen; —OH; (C$_1$–C$_6$-alkyl)NH—; di(C$_1$–C$_6$-alkyl)N—; —CO$_2$H; —CONH$_2$; —SH; (C$_1$–C$_6$-alkyl)S—; (C$_1$–C$_6$-alkyl)O—; (C$_1$–C$_6$-alkyl)OC(O)—; mod-aryl-(C$_1$–C$_6$-alkyl)OC(O)—; (C$_1$–C$_6$-alkyl)OC(O)NH—;(C$_1$–C$_6$-alkyl)C(O)NH—; mod-aryl-(C$_1$–C$_6$-alkyl)OC(O)NH—; mod-aryl-OC(O)-guanidino; H$_2$N—; mod-aryl-(C$_1$–C$_6$-alkyl)OC(O)-guanidino; mod-aryl-OC(O)-guanidino; (C$_1$–C$_6$-alkyl)NHC(O)—; di(C$_1$–C$_6$-alkyl)NC(O)—; mod-aryl-NHCO—; di(mod-aryl—NCO—; —OSO$_2$R$^{11}$; oxo; epoxy; mod-aryl-O—; mod-aryl-S—; mod-aryl-(C$_1$–C$_6$-alkyl)O—; mod-aryl-(C$_1$–C$_6$-alkyl)-S—; mod-Het-O—; mod-Het-S—; mod-Het-(C$_1$–C$_6$-alkyl)O; mod-Het-(C$_1$–C$_6$-alkyl)S—; mod-aryl; mod-Het—; —SO$_3$ —S(O)$_t$NH$_2$; —S(O)$_t$NHR$^{11}$; —S(O)$_t$NR$^{11}$R$^{11}$, where both R$^{11}$'s are independently selected; and —S(O)$_s$R$^{11}$; wherein guanidino, mod-aryl, oxo, epoxy, mod-Het—, s, t and R$^{11}$ are as defined above.

"Substituted-bicyclo-C$_6$-to-C$_{10}$-alkyl", as used herein, refers to a —(bicyclo-C$_6$-to-C$_{10}$-alkyl) group substituted with from one-to-three radicals selected from: halogen; —OH; (C$_1$–C$_6$-alkyl)NH—; di(C$_1$–C$_6$-alkyl)N—; —CO$_2$H; —CONH$_2$; —SH; (C$_1$–C$_6$-alkyl)S—; (C$_1$–C$_6$-alkyl)O—; (C$_1$–C$_6$-alkyl)OC(O)—; mod-aryl-(C$_1$–C$_6$-alkyl)OC(O)—; (C$_1$–C$_6$-alkyl)OC(O)NH—; (C$_1$–C$_6$-alkyl)C(O)NH—; mod-ary-(C$_1$–C$_6$-alkyl)OC(O)NH—; mod-aryl-OC(O)NH—; (C$_1$–C$_6$-alkyl)CO-guanidine; mod-aryl-(SO$_2$)-guanidino; (C$_1$–C$_6$-alkyl)OC(O)-guanidino; H$_2$N—; mod-aryl-(C$_1$–C$_6$-alkyl)OC(O)-guanidino; mod-aryl-OC(O)-guanidino; (C$_1$–C$_6$-alkyl)NHC(O)—; di(C$_1$–C$_6$-alkyl)NC(O)—; mod-aryl-NHCO—; di(mod-aryl)NCO—; —OSO$_2$R$^{11}$; oxo; epoxy; mod-aryl-O—; mod-aryl-S—; mod-aryl-(C$_1$–C$_6$-alkyl)O—; mod-aryl-(C$_1$–C$_6$-alkyl)-S—; mod-Het-O—; mod-Het-S—; mod-H-(C$_1$–C$_6$-alkyl)O; mod-Het-(C$_1$–C$_6$-alkyl)S—; mod-aryl; mod-Het—; —SO$_3$H; —S(O)$_t$NH$_2$; —S(O)$_t$NHR$^{11}$; —S(O)$_t$NR$^{11}$R$^{11}$, where both R$^{11}$'s are independently selected; and —S(O)$_s$R$^{11}$; wherein guanidino, mod-aryl, oxo, epoxy, mod-Het-, s, t and R$^{11}$ are as defined above. "Substituted-C$_3$-to-C$_6$-alkenyl", as used herein, refers to a -(C$_3$-to-C$_6$-alkenyl) group substituted with from one-to-three radicals selected from: halogen; —OH; (C$_1$–C$_6$-alkyl)NH—; di(C$_1$–C$_6$-alkyl)N—; —CO$_2$H; —CONH$_2$; —SH; (C$_1$–C$_6$- alkyl)S—; (C₁–C₆-alkyl)O—; (C₁–C₆-alkyl)OC(O)-;mod-aryl-(C₁–C₆-alkyl)OC(O)—; (C₁–C₆-alkyl)OC(O)NH—; (C₁–C₆-alkyl)C(O)NH—; mod-aryl-(C₁–C₆-alkyl)O-C(O)NH—; (C₁–C₆-alkyl)CO-guanidino; mod-aryl-(SO₂)-guanidino; (C₁–C₆-alkyl)OC(O)-guanidino; H₂N—; mod-aryl-(C₁–C₆-alkyl)OC(O)-guanidino; mod-aryl-OC(O)-guanidino; (C₁–C₆-alkyl)NHC(O)—; di(C₁–C₆-alkyl)NC(O)—; mod-aryl-NHCO—; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; mod-Het-O—; mod-Het-S—; mod-Het-(C₁–C₆-alkyl)O; mod-Het-(C₁–C₆-alkyl)S—; mod-aryl; mod-Het—; —SO₃H; —S(O)ₜNH₂; —S(O)ₜNHR¹¹; —S(O)ₜNR¹¹R¹¹, where both R¹¹'s are independently selected; and —S(O)ₛR¹¹; wherein guanidino, mod-aryl, oxo, epoxy, mod-Het-, s, t and R¹¹ are as defined above.

"Substituted-C₁-to-C₆-alkyl", as used herein, refers to a -(C₁-to-C₆-alkyl) group substituted with from one-to-three radicals selected from: halogen; —OH; (C₁–C₆-alkyl)NH—; di(C₁–C₆-alkyl)N—; —CO₂H; —CONH₂; —SH; (C₁–C₆-alkyl)S—; (C₁–C₆-alkyl)O—; (C₁–C₆-alkyl)OC(O)—; mod-aryl-(C₁–C₆-alkyl)OC(O)—; (C₁–C₆-alkyl)OC(O)NH-; (C₁–C₆-alkyl)C(O)NH—; mod-aryl(C₁–C₆-alkyl)OC(O)NH—; mod-aryl-OC(O)NH—; (C₁–C₆-alkyl)CO-guanidino; mod-aryl-(SO₂)-guanidino; (C₁–C₆-alkyl)OC(O)-guanidino; H₂N—; mod-aryl-(C₁–C₆-alkyl)OC(O)-guanidino; mod-aryl-OC(O)-guanidino; (C₁–C₆-alkyl)NHC(O)—; di(C₁–C₆-alkyl)NC(O)—; mod-aryl-NHCO-; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; mod-Het-O—; mod-Het-S—; mod-Het(C₁–C₆-alkyl)O; mod-Het-(C₁–C₆-alkyl)S—; mod-aryl; mod-Het—; —SO₃H; —S(O)ₜNH₂; —S(O)ₜNHR¹¹; —S(O)ₜNR¹¹R¹¹, where both R¹¹'s are independently selected; and —S(O)ₛR¹¹; wherein guanidino, mod-aryl, oxo, epoxy, mod-Het-, s, t and R¹¹ are as defined above.

"Substituted-C₃-to-C₆-alkynyl", as used herein, refers to a -(C₃-to-C₆-alkynyl) group substituted with from one-to-three radicals selected from: halogen; —OH; (C₁–C₆-alkyl)NH—; di(C₁–C₆-alkyl)N—; —CO₂H; —CONH₂; —SH; (C₁–C₆-alkyl)S—; (C₁–C₆-alkyl)O—; (C₁–C₆-alkyl)OC(O)—; mod-aryl-(C₁–C₆-alkyl)OC(O)—; (C₁–C₆-alkyl)OC(O)NH—; (C₁–C₆-alkyl)C(O)NH—; mod-aryl-(C₁–C₆-alkyl)OC(O)NH—; mod-aryl-OC(O)NH—; (C₁–C₆-alkyl)CO-guanidino; mod-aryl-(SO₂)-guanidino; (C₁–C₆-alkyl)OC(O)-guanidino; H₂N—; mod-aryl-(C₁–C₆-alkyl)OC(O)-guanidino; mod-aryl-OC(O)-guanidino; (C₁–C₆-alkyl)NHC(O)—; di(C₁–C₆-alkyl)NC(O)—; mod-aryl-NHCO-; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; mod-Het-O—; mod-Het-S—; mod-Het(C₁–C₆-alkyl)O; mod-Het-(C₁–C₆-alkyl)S—; mod-aryl; mod-Het—; —SO₃H; —S(O)ₜNH₂; —S(O)ₜNHR¹¹; —S(O)ₜNR¹¹R¹¹, where both R¹¹'s are independently selected; and —S(O)ₛR¹¹; wherein guanidino, mod-aryl, oxo, epoxy, mod-Het-, s, t and R¹¹ are as defined above.

"Substituted-cyclo-C₄-to-C₁₀-alkenyl", as used herein, refers to a -(cyclo-C₄-to-C₁₀alkenyl) group substituted with from one-to-three radicals selected from: halogen; —OH; (C₁–C₆-alkyl)NH—; di(C₁–C₆-alkyl)N—; —CO₂H; —CONH₂; —SH; (C₁–C₆-alkyl)S—; (C₁–C₆-alkyl)O—; (C₁–C₆-alkyl)OC(O)-;mod-aryl-(C₁–C₆-alkyl)OC(O)—; (C₁–C₆-alkyl)OC(O)NH—; (C₁–C₆-alkyl)C(O)NH—; mod-aryl(C₁–C₆-alkyl)OC(O)NH—; mod-aryl-OC(O)NH—; (C₁–C₆-alkyl)CO-guanidino; mod-aryl-(SO₂)-guanidino; (C₁–C₆-alkyl)OC(O)-guanidino; H₂N—; mod-aryl(C₁–C₆-alkyl)OC(O)-guanidine mod-aryl-OC(O)-guanidino; (C₁–C₆-alkyl)NHC(O)—; di(C₁–C₆-alkyl)NC(O)—; mod-aryl-NHCO—; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; mod-Het-O—; mod-Het-S—; mod-Het(C₁–C₆-alkyl)O; mod-Het-(C₁–C₆-alkyl)S—; mod-aryl; mod-Het-; —SO₃H; —S(O)ₜNH₂; —S(O)ₜNHR¹¹; —S(O)ₜNR¹¹, where both R¹¹'s are independently selected; and —S(O)ₛR¹¹; wherein guanidino, mod-aryl, oxo, epoxy, mod-Het-, s, t and R¹¹ are as defined above.

"Substituted-cyclo-C₃-to-C₁₀-alkyl", as used herein, refers to a —(cyclo-C₃-to-C₁₀alkyl) group substituted with from one-to-three radicals selected from: halogen; —OH; (C₁–C₆-alkyl)NH—; di(C₁–C₆-alkyl)N-;-CO₂H; —CONH₂; —SH; (C₁–C₆-alkyl)S—; (C₁–C₆-alkyl)O—; (C₁–C₆-alkyl)OC(O)—; mod-aryl-(C₁–C₆-alkyl)OC(O)—; (C₁–C₆-alkyl)OC(O)NH—; (C₁–C₆-alkyl)C(O)NH-; mod-aryl(C₁–C₆-alkyl)OC(O)NH—; mod-aryl-OC(O)NH—; (C₁–C₆-alkyl)CO-guanidino; mod-aryl-(SO₂)-guanidino; (C₁–C₆-alkyl)OC(O)-guanidino; H₂N—; mod-aryl(C₁–C₆-alkyl)OC(O)-guanidine mod-aryl-OC(O)-guanidino; (C₁–C₆-alkyl)NHC(O)—; di(C₁–C₆-alkyl)NC(O)—; mod-aryl-NHCO—; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; mod-Het-O—; mod-Het-S—; mod-Het(C₁–C₆-alkyl)O; mod-Het-(C₁–C₆-alkyl)S—; mod-aryl; mod-Het—; —SO₃H; S(O)ₜNH₂; —S(O)ₜNHR¹¹; —S(O)ₜNR¹¹R¹¹, where both R¹¹'s are independently selected; and —S(O)ₛR¹¹; wherein guanidino, mod-aryl, oxo, epoxy, mod-Het-, s, t and R¹¹ are as defined above.

"Substituted-bicyclo-C₆-to-C₁₀-alkenyl-C₁-to-C₆-alkyl", as used herein, refers to a —(bicyclo-C₆-to-C₁₀-alkenyl)-C₁-to-C₆-alkyl group substituted with from one-to-three radicals selected from:
halogen; —OH; (C₁–C₆-alkyl)NH—; di(C₁–C₆-alkyl)N—; —CO₂H; —CONH₂; —SH; (C₁–C₆-alkyl)S—; (C₁–C₆-alkyl)O—; (C₁–C₆-alkyl)OC(O)-; mod-aryl-(C₁–C₆-alkyl)OC(O)—; (C₁–C₆-alkyl)OC(O)NH—; (C₁–C₆-alkyl)C(O)NH—; mod-aryl-(C₁–C₆-alkyl)O-C(O)NH—; mod-aryl-OC(O)NH—; (C₁–C₆-alkyl)CO-guanidino; mod-aryl-(SO₂)-guanidino; (C₁–C₆-alkyl)OC(O)-guanidino; H₂N—; mod-aryl-(C₁–C₆-alkyl)OC(O)-guanidino; mod-aryl-OC(O)-guanidino; (C₁–C₆-alkyl)NHC(O)—; di(C₁–C₆-alkyl)NC(O)—; mod-aryl-NHCO—; di(mod-aryl)NCO—; —OSO₂R¹¹; oxo; epoxy; mod-aryl-O—; mod-aryl-S—; mod-aryl-(C₁–C₆-alkyl)O—; mod-aryl-(C₁–C₆-alkyl)-S—; rood-Her-O—; mod-Het-S—; mod-Het-(C₁–C₆-alkyl)O; mod-Het-(C₁–C₆-alkyl)S—; mod-aryl; mod-Het-; —SO₃H; —S(O)ₜNH₂; —S(O)ₜNHR¹¹; —S(O)ₜNR¹¹R¹¹, where both R¹¹'s are independently selected; and —S(O)ₛR¹¹; wherein guanidino, mod-aryl, oxo, epoxy, mod-Het—, s, t and R¹¹ are as defined above.

"Thioalkoxyalkyl" refers to a thioalkoxy group, as defined above, except that it is attached to the remainder of the molecule via an alkyl group.

"Thiolalkyl" refers to an alkyl group, as defined above, substituted with an —SH group.

"Thiooxo" refers to a sulfur atom forming a thiocarbonyl group.

"Unsubstituted aryl" refers to mono-, di-, tri- or tetracyclic aromatic groups, charged or uncharged, the rings of which are comprised of from 3-to-7 carbon atoms. Examples of unsubstituted aryl include, but are not limited to, phenyl, 1- or 2-naphthyl, azulenyl, fluorenyl, (1, 2)-dihydronaphthyl, (1 ,2, 3, 4)-tetrahydronaphthyl, indenyl, indanyl and the like, which are solely substituted by hydrogen.

"Pharmaceutically-acceptable salts, esters, amides and prodrugs" refers to those carboxylate salts, amino acid addition salts, esters, amides and prodrugs of the compounds of the present invention which are, within the scope of sound medical judgement, suitable for use in contact with the tissues of humans and lower animals without undue toxicity, irritation, allergic response, or the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention, which may be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, tdmethylamine, triethylamine, ethylamine, and the like (see, for example S. M. Berge, et al., "Pharmaceutical Salts," *J. Pharm. Sci.*, 66:1–19 (1977)).

Examples of pharmaceutically-acceptable, non-toxic esters of the compounds of this invention include $C_1$-to-$C_6$-alkyl esters wherein the alkyl group is a straight or branched chain. Acceptable esters also include $C_5$-to-$C_7$-cycloalkyl esters as well as arylalkyl esters such as, but not limited to benzyl. $C_1$-to-$C_4$ alkyl esters are preferred. Esters of the compounds of the present invention may be prepared according to conventional methods. Conversely, non-toxic esters of alcoholic moieties on the compounds of the invention may be constructed by condensing these alcohols with $C_1$-to-$C_6$-alkyl carboxylic acids, $C_1$-to-$C_6$alkyl dicarboxylic acids or aryl-carboxylic acids. Examples of such esters include, but are not limited to acetyl, benzoyl or hemisuccinyl.

Examples of pharmaceutically-acceptable, non-toxic amides of the compounds of this invention include amides derived from ammonia, primary $C_1$-to-$C_6$-alkyl amines and secondary di-$C_1$-to-$C_6$-alkyl amines. In the case of secondary amines the amine may also be in the form of a 5-or- 6 membered heterocycle containing one nitrogen atom. Amides derived from ammonia, $C_1$-to-$C_3$-alkyl primary amides and di-$C_1$-to-$C_2$-alkyl secondary amides are preferred. Amides of the compounds of the invention may be prepared according to conventional methods.

"Prodrug" refers to compounds that are rapidly transformed in vivo to yield the parent compound of the above formula, for example, by hydrolysis in blood. A thorough discussion is provided in T. Higuchi and V. Stella, "Prodrugs as Novel Delivery Systems", Vol 14 of the A. C. S. Symposium Series, and in Bioreversible Carriers in Drug Design, ed. Edward B. Roche, American Pharmaceutical Association and Pergamon Press, 1987.

Prodrugs of compounds of the present invention may be prepared by suitable methods. For those compounds in which the prodrug moiety is an amino acid or peptide functionality, the condensation of the drug's amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z or Cbz), o-chlorobenzyloxycarbonyl ((2-$C_1$)Z)), p-nitrobenzyloxycarbonyl (Z(NO$_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt), dimethylphosphino-thioyl (Mpt), and the like.

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic), and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2, 6-dimethylbenzenesulfonyl (Mrs) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP), and the like.

Numerous asymmetric centers exist in the compounds of the present invention. Except where otherwise noted, the present invention contemplates the various stereoisomers and mixtures thereof.

When used in the above or other treatments, a therapeutically-effective amount of one of the compounds of the present invention, meaning a sufficient amount of the compound to treat a particular disorder, at a reasonable benefit/risk ratio, may be employed in pure form or, where such forms exist, in pharmaceutically acceptable salt, ester or prodrug fonn. Alternatively, the compound may be administered as pharmaceutical compositions containing the compound of interest in combination with one or more pharmaceutically-acceptable excipients. It will be understood, however, that the total daily usage of the compounds and compositions of the present invention will be decided by the attending physician within the scope of sound medical judgement.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 10 mg/kg of patients body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically-acceptable carrier or excipient, meaning a non-toxic solid, semi-solid or liquid filler, diluent, encapsulating material or formulation auxiliary of any type, which may be administered orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofuffuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more processes. The starting materdais for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR 900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, Novel immunosuppressants isolated from A streptomyces. I. Taxonomy of the producing strain. J. Antibiot., 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, Novel immunosuppressants isolatedpom A streptomyces. H. Fermentation, isolation and physicochemical and biological characteristics. J. Antibiot., 1988. XLI(11), 1592–1601; (iii) T. Arai, Y. Koyama, T. Suenaga and H. Honda, *Ascomycin, An Antifungal Antibiotic. J. Antibiot.,* 1962.15(231-2); and (iv) T. Arai in U.S. Pat. No. 3,244,592. One or more of the processes discussed below may be then employed to produce the desired compound of the invention.

Such processes comprise:

(a) producing a compound of formula I, which contains a CH-OLg group, by selective activation of a selected CH-OH group in a corresponding compound wherein -OLg is a leaving group which is easily displaced by nucleophilic attack;

(b) producing a compound of formula I, which contains a CH—$N_3$ group, by selective displacement of an —OLg group in a corresponding compound;

(c) producing a compound of formula I, which contains a CH—$NH_2$ group, by selective reduction of a CH—$N_3$ group in a corresponding compound;

(d) producing a compound of formula I, which contains a R'—NR"COR group, by selective acylation of a R'—NR"H group in a corresponding compound wherein R is selected from hydrogen, aryl, arylalkyl, alkyl, Het, heterocyclic, heterocyclic-alkyl, cycloalkyl, and cycloalkylalkyl such that R' and/or R" represent(s) a radical derived from formula I; or R' and R" are $R^{14}$ and $R^{15}$ respectively, as defined above, and R represent(s) a radical derived from formula I;

(e) producing a compound of formula I, which contains a CH—$NR^1R^2$ group, by selective alkylation of a CH-$NH_2$ group in a corresponding compound wherein $R^1$ and $R^2$ are independently selected from hydrogen, aryl, arylalkyl, alkyl, heterocyclic, heterocyclic alkyl, Het, Het-alkyl, cycloalkyl, and cycloalkylalkyl;

(f) producing a compound of formula I, which contains a CH—NHC(O)NH—$R^{14}$ group, by selective urea or thiourea formation from a CH—$NH_2$ group in a corresponding compound, wherein $R^{14}$ is as defined above; or producing a compound of formula I, which contains a CH—NHC(O)$NR^{14}R^{15}$ group, wherein $R^{14}$ an $R^{15}$ are as defined above, by selective formation of a CH—N=C=O group, and addition of an amine $HNR^{14}R^{15}$;

(g) producing a compound of formula I, which contains a CH—NH—$SO_2R$ group, by selective sulfonylation of a CH—$NH_2$ group in a corresponding compound wherein R is selected from aryl, arylalkyl, alkyl, cycloalkyl, cycloalkylalkyl, Het, Het-alkyl, heterocyclic alkyl and heterocyclic;

(h) producing a compound of formula 1, which contains a CH—NH—C(=O)OR group, by selective carbamate formation from a selected CH—NH$_2$ group in a corresponding compound wherein R is selected from aryl, cycloalkyl, cycloalkyl alkyl, alkyl, heterocyclic alkyl, Het, Het-alkyl, heterocyclic and arylalkyl;

(i) producing a compound of formula I, which contains a CH—NH—C(=NH)NH$_2$ group, by selective guanidinium formation from a CH—NH$_2$ group in a corresponding compound;

(j) producing a compound of formula I, which contains a CH—NH—SR group, by selective sulfenylation of a CH—NH$_2$ group in a corresponding compound wherein R is selected from aryl, arylalkyl, alkyl, cycloalkyl, cycloalkylalkyl, heterocyclic alkyl and Het, Het-alkyl, heterocyclic;

(k) producing a compound of formula I, which contains a CH—X group, by selective halogenation of a CH—OH group in a corresponding compound wherein X is selected from chlorine, bromine, fluorine and iodine;

(l) producing a compound of formula I, which contains a CH—P(O)(OR)$_2$ group, by selective phosphonic acid ester formation of a CH—X group in a corresponding compound wherein R is independently selected from alkyl, arylalkyl, and aryl;

(m) producing a compound of formula I, which contains a CH—O—P(O)(OR)$_2$ group, by selective phosphorylation of a CH—OH group in a corresponding compound wherein R is independently selected from hydrogen, alkyl, arylalkyl, and aryl;

(n) producing a compound of formula I, which contains a CH—S—R group, by selective thioether formation from a CH—OH group in a corresponding compound wherein R is selected from cycloalkyl, cycloalkyl alkyl, Het, Het-alkyl, heterocyclic, heterocylic alkyl, alkyl, arylalkyl, and aryl;

(o) producing a compound of formula I, which contains a CH—O—C(=S)—OR group, by selective aryl- or alkyloxythiocarbonylation of a CH—OH group in a corresponding compound wherein R is selected from cycloalkyl, cycloalkyl alkyl, Het, Het-alkyl, heterocyclic, heterocylic alkyl, alkyl, arylalkyl, and aryl;

(p) producing a compound of formula I, which contains one or more CH—O—R groups, by selective ether formation of one or more CH—OH groups in a corresponding compound wherein R is selected from cycloalkyl, cycloalkylalkyl, Het, Het-alkyl, heterocyclic, (heterocylic)alkyl, (heterocyclic)alkenyl, (heterocyclic)alkynyl, alkyl, arylalkyl, aryl, loweralkoxycarbonylalkyl, arylalkoxycarbonylalkyl, arylalkylcarbonylalkyl, trialkylsilylcarbonylalkyl, trialkylstannylcarbonylalkyl, amidocarbonylalkyl, alkylamidocarbonylalkyl, dialkylamidocarbonylalkyl, arylamidocarbonylalkyl and heterocyclicamidocarbonylalkyl;

(q) producing a compound of formula I, which contains a CH(substituted)phthalimide group, by selective cyclic imide formation using a CH—NH$_2$ group in a corresponding compound;

(t) producing a compound of formula I, which contains a CH$_2$ group, by selective deoxygenation of a CH—O—C(=S)—OR group in a corresponding compound;

(u) producing a compound of formula I, which contains a C(OH)=CH—C(=O) or a C(=O)—CH$_2$—C(=O) group, by selective oxidation of a CH(OH)—CH$_2$—C(=O) group in a corresponding compound;

(v) producing a compound of formula I, which contains a C(=O)—CR$_1$R$^2$—C(=O) group, by selective alkylation of a C(OH)=CH—C(=O) or a C(=O)—CH$_2$—C(=O) group in a corresponding compound, wherein R$_1$ and R$_2$ are independently selected from hydrogen, aryl, cycloalkyl, cycloalkyl alkyl, alkyl, heterocyclic alkyl, Het, heterocyclic and arylalkyl, but both cannot be hydrogen;

(w) producing a compound of formula I, which contains a C(=O)—CX$_1$X$_2$—C(=O) group, by selective halogenation of a C(OH)=CH—C(=O) or a C(=O)—CH$_2$—C(=O) group in a corresponding compound wherein X$_1$ and X$_2$ are independently selected from fluorine, chlorine, bromine and iodine;

(x) producing a compound of formula I, which contains a C(=O)—CH(OH)—C(=O) group, by selective oxidation of a C(OH)=CH—C(=O) or a C(=O)—CH$_2$—C(=O) group in a corresponding compound;

(aa) producing a compound of formula I, which contains a C(=CH—R)—CH$_2$—C(=O) group, by selective olefination of a C(OH)=CH—C(=O) or a C(=O)—CH$_2$—C(=O) group in a corresponding compound wherein R is selected from alkyl, aryl and arylalkyl;

(bb) producing a compound of formula I, which contains a C(OCOR)=CH—C(=O) group, by selective O-acylation of a C(OH)=CH—C(=O) or a C(=O)—CH$_2$—C(=O) group in a corresponding compound wherein R is selected from aryl, cycloalkyl, cycloalkyl alkyl, alkyl, heterocyclic alkyl, Het, Het-alkyl, heterocyclic and arylalkyl;

(cc) producing a compound of formula I, which contains a C(NH—R)=CH—C(=O) group, by selective amination of a C(OH)=CH—C(=O) or a C(=O)—CH$_2$—C(=O) group in a corresponding compound wherein R is selected from alkylamine, arylalkylamine, arylamine and amino acid derivatives;

(dd) producing a compound of formula I, which contains C(O)—C(=CH—R)—C(=O) group, by selective alkylidene formation of a C(OH)=CH—C(=O) or a C(=O)—CH$_2$—C(=O) group in a corresponding compound wherein R is selected from hydrogen, aryl, cycloalkyl, cycloalkyl alkyl, alkyl, heterocyclic alkyl, Het, Het-alkyl, heterocyclic and arylalkyl;

(ee) producing a compound of formula I, which contains a carbon-carbon double bond, by elimination of HL from a corresponding compound, where L is a leaving group;

(ff) producing a compound of formula I, which contains a quinoxaline, benzoquinoxaline, pyrazino[2,3-d]pyridazine, pyrido[3,4-b]pyrazine, or a pteridine by condensation of a 1,2-dicarbonyl or masked 1,2-dicarbonyl groups of a corresponding compound with an appropriate aromatic aliamine;

(gg) producing a compound of formula I, which contains one or more hydroxyl groups, by selective reduction of one or more C=O groups of a corresponding compound;

(hh) producing a compound of formula I, which contains one dihydrobenzo[1,5]thiazepine, by reaction of an alpha, beta-unsaturated ketone of a corresponding compound with an appropriate 2-aminothiophenol;

(ii) producing a compound of formula I, which contains one or more carbonyl groups, by selective oxidation of one or more hydroxyl groups of a corresponding compound;

(jj) producing a compound of formula I, by selective reaction of one of the carbonyl groups of a corresponding compound and dithiols;

(kk) producing a compound of formula I, which contains an oxime group, by selective reaction of one of the carbonyl groups of a corresponding compound with hydroxyl amine or O-alkylated hydroxyl amines;

(ll) producing a compound of formula I, which contains a pyrazole system, by condensation of a 1,3-dicarbonyl group of a corresponding compound and appropriate hydrazines;

(mm) producing a compound of formula I, which contains a substituted pyrimidine system, by condensation of the 1,3-dicarbonyl group of a corresponding compound with appropriate amidines, guanidines, isoureas, ureas and thioureas;

(nn) producing a compound of formula I, which contains a furan system, by reaction of the 1,3-dicarbonyl group of a corresponding compound with appropriate diazoacetic esters or diazomethyl ketones;

(oo) producing a compound of formula I, which contains an isoxazole system, by condensation of the 1,3-dicarbonyl group of a corresponding compound with hydroxyl amine;

(pp) producing a compound of formula I, which contains a pyridine system, by condensation of the 1,3-dicarbonyl group of a corresponding compound with appropriate malonic acid derivatives or cyanoacetic acid derivatives;

(qq) producing a compound of formula I, which contains a benzo[1,5]thiazepine, benzo[1,5]oxazepine or benzo[1,5]diazepine system, by condensation of the 1,3-dicarbonyl group of a corresponding compound with appropriate 2-aminothiophenols, 2-aminophenols, and 1,2-aromatic diamines;

(rr) producing a compound of formula I, which contains a keto-substituted furan system, by reaction of the 1,3-dicarbonyl group of a corresponding compound with appropriate aldehydes, and enol ethers;

(ss) producing a compound of formula I, which contains a substituted phenyl group, by C-arylation of a 1,3-dicarbonyl group of a corresponding compound with appropriate 1-halo-2-nitro-aromatics;

(uu) producing a compounds of formula I, which contains a 2-isoxazoline, by nitrile oxide 1,3-dipolar cycloaddition to an enone;

(zz) producing a compound of formula I, which contain either a beta-hydroxy ketone or an alpha, beta-enone, by reductive hydrolysis of a corresponding 2-isoxazoline and subsequent separation of the two compounds;

(eee) producing a compound of formula I, which contains a hydrazone, by selective hydrazone formation with a corresponding ketone;

(hhh) producing a compound of formula I, which contains an allylic alcohol, by selective reduction of a corresponding enone;

(iii) producing a compound of formula I, which contains an epoxide, by selective addition of the carbene arising from diazomethane across an activated carbonyl;

(jjj) producing a compound of formula I, which contains a carboxylic acid, by selective ester cleavage in a corresponding compound;

(kkk) producing a compound of formula I, which contains a substituted or unsubstituted carboxamide, by selective condensation of the corresponding amine with a corresponding carboxylic acid;

(lll) producing a compound of formula I, which contains a 24R-hydroxyl substituent, by selective inversion of the naturally occurring 24S configuration;

(mmm) producing a compound of formula I, which contains an alkyloxycarbonyl hydrazone, by selective condensation of an alkyl carbazate with a corresponding compound of formula I, having a ketone;

(ppp) producing a compound of formula I, which contains one thiazole, by condensation of an alpha substituted carbonyl or an alpha substituted masked carbonyl group of a corresponding compound with an appropriate thioamide, thiourea or with dithiocarbamic acid derivatives, where the alpha substituent L is a leaving group;

(qqq) producing a compound of formula I, which contains one imidazole, by condensation of an alpha substituted carbonyl or an alpha substituted masked carbonyl group of a corresponding compound with an appropriate amidine, isourea or guanidine, where the substituent L is a leaving group;

(rrr) producing a compound of formula I, which contains one oxazole, by condensation of an alpha substituted carbonyl or an alpha substituted masked carbonyl group of a corresponding compound with an appropriate amide, where the substituent L is a leaving group;

(sss) producing a compound of formula I, which contains a tertiary alcohol, by selective addition of a Grignard reagent or an organometallic reagent to a carbonyl moiety of a corresponding compound;

(ttt) producing a compound of formula I, which contains one pyrrole, by cyclization of an appropriate gamma-amino alpha hydroxy carbonyl or a masked gamma-amino alpha hydroxy carbonyl of a corresponding compound prepared by process (sss);

(uuu) producing a compound of formula I, which contains one pyrazine, by condensation of a 1,2-dicarbonyl or masked 1,2-dicarbonyl group of a corresponding compound with an appropriate 1,2-diamine in the presence of an oxidizing agent;

(vvv) producing a compound of formula I, which contains one pyridine, by condensation of a 1,5-dicarbonyl group prepared by process (sss) of a corresponding compound with ammonia;

(www) producing a compound of formula I, which contains one pyridazine, by condensation of a 1,4-dicarbonyl group prepared by process (sss) of a corresponding compound with hydrazine;

(xxx) producing a compound of formula I, which contains a 1,2-thiocarbonate, by reacting a 1,2-diol of a corresponding compound with thiocarbonyldiimidazole or an appropriately activated thiocarbonate;

(yyy) producing a compound of formula I, which contains a 1,2-carbonate, by reacting a 1,2-diol of a corresponding compound with carbonyldiimidazole, triphosgene, phosgene or an appropriately activated carbonate;

(zzz) producing a compound of formula I, which contains a 1,2-phosphonate group, by reacting a 1,2-diol of a corresponding compound with an appropriate alkoxyphosphonyl dichloride;

(aaaa) producing a compound of formula I, which contains an olefin, by reduction of a 1,2-thiocarbonate prepared by process (xxx) of a corresponding compound;

(bbbb) producing a compound of formula I, which contains a $CH_2$ group, by selective reduction of a 1,2-dicarbonyl or masked 1,2-dicarbonyl group of a corresponding compound;

(cccc) producing a compound of formula I, which contains an indole group, by selective reduction and condensation of a 2-(o-nitrophenyl)-1,3-diketone [prepared by process (ss)] of a corresponding compound;

(dddd) producing a compound of formula I, which contains a substituted triazole group, by cycloaddition of a CH—$N_3$ group in a corresponding compound with appropriate acetylene analogues;

(eeee) producing a compound of formula I, which contains a substituted pyrrole group, by reaction of a CH—$NH_2$ group in a corresponding compound with appropriate dicarbonyl compounds;

(ffff) producing a compound of formula I, which contains one ethanalyl group, first by selective oxidation of the double bond of an allyl group to a vicinal diol, followed by oxidative cleavage of the diol in a corresponding compound;

(gggg) producing a compound of formula I, which contains one carboxymethyl group, by selective oxidation of an ethanalyl group in a corresponding compound;

(hhhh) producing a compound of formula I, which contains one alkyl carboxymethyl group, by esterification of a carboxymethyl group in a corresponding compound;

(iiii) producing a compound of formula I, which contains one cyclopropylmethyl group, by selective cyclopropanation of the double bond of an allyl group in a corresponding compound;

(jjjj) producing a compound of formula I, which contains one pyrrole, by reaction of a 1,4-dicarbonyl group with amines in a corresponding compound;

(kkkk) producing a compound of formula I, which contains one furan, by cyclization of a 1,4-dicarbonyl group in a corresponding compound;

(llll) producing a compound of formula I, which contains one methyl ketone, by selective oxidation of the double bond of an allyl group in a corresponding compound;

(nnnn) producing a compound of formula I, which contains a hydrazide, by reduction of the corresponding hydrazone;

(oooo) producing a compound of formula I, which contains an amine, by reduction of the corresponding oxime;

(pppp) producing a compound of formula I, which contains an alpha,beta-saturated ketone, by reduction of the corresponding alpha,bern-unsaturated enone;

(qqqq) producing a compound of formula I, which contains an isoxazoline, by treatment of a beta-hydroxy oxime with a dehydrating reagent;

(rrrr) producing a compound of formula I, which contains an beta-hydroxy carbonyl, by treatment of a carbonyl with a base in the presence of another carbonyl moiety;

(ssss) producing a compound of formula I, which contains a cyclic imine, by treatment of an enone system with a glycine imine in the presence of base resulting in first Michael addition at the beta-carbon and subsequent imine formation upon aqueot/s workup;

(tttt) producing a compound of formula I, which contains a substituted pyrrole, by treatment of an enone with a glycine imine in the presence of an appropriate catalyst to induce a 1,3-dipolar cycloaddition;

(uuuu) producing a compound of formula I, which contains a beta-keto carbox-ylic acid, ester or amide, by decomposition with light or heat of an alpha diazoketone;

(vvvv) producing a compound of formula I which contains a ketone, a product of decarboxylation of a beta-keto carboxylic acid, by heating;

(yyyy) producing a compound of formula I which contains a—CHOC(O)OR$^{400}$, by selective mod-aryl-, mod-Het-, or alkyloxy-carbonylation of a —CHOH group in a corresponding compound;

(zzzz) producing a compound of formula I, which contains an allylie hydroxyl group, by selective oxidation of an allylie methylene group in a corresponding compound.

In process (a), suitable reagents for activation of an alcohol include acetic anhydride, trifluoromethanesulfonic anhydfide (triflic anhydfide), methanesulfonyl chloride (mesyl chloride), p-toluenesulfonyl chloride (tosyl chloride), trifluoroacetic anhydride, trifluoroacetyl chloride, methoxysulfonyl fluoride (magic methyl), o-nitrobenzenesulfonyl chloride, 1-methyl-2-fiuoropyridinium salt and the like.

The activation may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, luffdine, picoline, 4-N,N-dimethylaminopyridine, etc.), quinoline, and the like, preferably in the presence of organic bases such as triethylamine or pyfidine.

The activation may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either [R]- or [S]-configuration can be obtained selectively and separately.

In process (b), suitable azide reagents include well-established alkali metal azides such as sodium or lithium azides (NAN$_3$ or LiN$_3$) in the presence or absence of crown ethers, more reactive tetraalkylammonium azides (Danishefski, S. J.; DeNinno, M. P.; Chen, S. -H. *J. Am. Chem. Soc.* 1988, 110, 3929), tetramethylguanidinium azide, (Papa, A. J. *J. Org. Chem.* 1966, 31, 1426), a copper-assisted azide reaction (Yamamoto, Y.; Asao, N. *J. Org. Chem.* 1990, 55, 5303) and a hydrogen azide-amine system (Saito, S.; Yokoyama, H.; Ishikawa, T.; Niwa, N.; Moriwake, T. *Tetrahedron Lett.* 1991, 32,663; Saito, S.; Takahashi, N.; Ishikawa, T.; Moriwake, T. *Tetrahedron Lett.* 1991, 32,667). The azide displacement reaction may be carried out in a solvent which does not adversely affect the reaction (e.g. chloroform, dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature.

In process (c), the reduction may be carried out catalytically using hydrogen. Suitable catalysts include, but are not limited to platinum catalysts (e.g. platinum oxide, platinum black), palladium catalysts (e.g. palladium oxide, palladium on charcoal, palladium black, palladium hydroxide on charcoal, palladium on calcium carbonate poisoned with lead, palladium on barium carbonate with quinoline), nickel catalysts (e.g. nickel oxide, Raney nickel), rhodium catalysts (e.g. rhodium on alumina). Reduction may also be carried out using metal reducing reagents (see Review; Scriven, E. F. V.; Turnbull, K. *Chem Rev.* 1988, 88, 321; Patai, S., Ed., "The Chemistry of the Azido Group," Interscience Publishers, New York, 1971; Scriven, E. F. V., Ed., "*Azides and Nitrenes Reactivity and Utility*," Academic Press, Inc., New York, 1984) such as sodium borohydride under phase-transfer conditions, borohydride supported on an ion exchange resin, lithium aluminum hydride and the like, furthermore, 1,3-propanedithiol-triethylamine method (Bayley, H.; Staudring, D. N.; Knowles, J. R. *Tetrahedron Lett.* 1978, 3633), triphenylphosphine (Vaultier, M.; Knouzi, N.;

Carrie, R. *Tetrahedron Lett.* 1983, 24,763), and sodium tellurium hydride (Suzuki, H.; Takaoka, K. *Chem Lett.* 1984, 1733).

The reduction may be carried out in a solvent which does not adversely affect the reaction (e.g., alcohols, water, acetone, dichloromethane, tetrahydrofuran, pyridine or N,N-dimethylformamide or a mixture thereof). The reaction may be conducted above, at, or below ambient temperature.

In process (d), suitable N-acylations may be carried out using the methods of symmetric carboxylic acid anhydrides, carboxylic acid halides, mixed carbonic-carboxylic anhydrides, active esters (p-nitrophenylester, trichlorophenyl ester, pentafluorophenyl ester, N-hydroxysuccinimide, cyanoethyl, 2,2,2-trichloroethyl and the like), and carboxylic acid with suitable condensing reagents such as DCC (N,N-dicyclohexylcarbodiimide and its related condensing agents), DCC-HOBt (N,V-dicyclohexylcarbodiimide-1-hydroxybenzotriazole), Woodward reagent K method, N,N-carbonyldiimidazole and phosphonium containing reagents (e.g. benzotriazolyloxytris[dimethylamino]-phosphonium hexafluorophosphate, N,N-bis[2-oxo-3-ox-azolidinyl]phosphorodiamidic chloride, diethylphosphorobromidate, diphenylphosphoryl azide, bromo tris[dimethylamino]phosphonium hexafluorophosphate, and the like). Suitable reagents for amide formation include, but are not limited to formyl derivatives, acetyl halides (chloroacetyl, trichloroacetyl, o-nitrophenylacetyl, o-nitrophenoxyacetyl, acetoacetyl, [N'-dithiobenzyloxycarbonylamino]acetyl and the like), and substituted propionyl derivatives (3-phenylpropionyl, isobutyryl, picolinoyl, and the like). Other groups may be found in volume 3 of *The Peptides* Gross, E. and Meinhofer, J. Academic Press, 1981 and *Protective Groups in Organic Synthesis* Greene, T. W. John Wiley & Sons, New York, Chapter 7, 1981. Typically used coupling conditions are described by Gross, E.; Meinhofer, J. *"The Peptides"* vol. 3, Academic Press, 1981. The N-acylation may be carried out in a solvent which does not adversely affect the reaction (e.g. acetone, dichloromethane, chloroform, tetrahydrofuran, N,N-dimethylformamide, dimethylsulfoxide, diethylether, and the like, or a mixture thereof). The reaction may be conducted above, at, or below ambient temperature. Alternatively, metal salts may be formed from the desired amines and then condensed with an ester which may or may not be activated. These salts may be formed by treatment of the neutral amine with trialkylaluminums (See J. I. Levin, E. Turos, S. M. Weinreb *Synthetic Communications* 1982, 12, 989-93), Sn[N(Si(CH$_3$)$_3$)]$_2$ (See W. Wang, E. J. Roskamp *J. Org. Chem.* 1992, 57, 6101-3), or grignard reagents. For other methods see A. Solladie-Cavallo, M. Bencheqroun *J. Org. Chem.* 1992, 57, 5831-4 as well as footnotes 2, 3, 4, 5, 6 and 7 therein.

In process (e), N-alkylations may be carried. out using aldehydes or ketones-followed by reduction of the initially formed iminium ion {The following reagents can be used for the reduction; sodium cyanoborohydride-boron trifluoride or the reducing reagents cited in process (c) }, corresponding halides in the presence of bases listed in process (a), or lithium dialkyl cuprate (King, F. E.; King, T. J.; Muir, I. H. M. *J. Chem. Soc.* 1946, 5; Yamamoto, H.; Maruoka, K. *J. Org. Chem.* 1980, 45, 2739). Suitable reagents for N-alkylation include, but are not limited to benzyl halide, 3,4-dimethoxybenzyl halide, nitrobenzyl halide, di(pmethoxyphenyl)methyl halide, triphenylmethyl halide, and the like. Other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-alkylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (f), urea formation may be carded out from the following reactions; reaction with silicon tetraisocyanate or silicon tetraisothiocyanate (Neville, R. G.; McGee, J. *J. Can. J. Chem.* 1963, 41, 2123), reactibn with N,N-carbonyldiimidazole or N,N-thiocarbonyldiimidazole, followed by N-substituted primary or secondary amines or ammonia (Staab, H. A.; Wendel, K. *Org. Synth.* 1968, 48, 44), and reaction with phosgene or thiophosgene in the presence of tert-amine, followed by N-substituted primary or secondary amines or ammonia. The ureido formation may be carried out in a solvent which does not adversely affect the reaction (e.g. acetone, toluene, dichloromethane, tetrahydrofuran, pyridine, N,N-dimethylformamide, etc. or a mixture thereof). The reaction may be conducted above, at, or below ambient temperature.

Alternatively, urea formation may be carried out by first forming an acyl azide by activating a carboxylic acid in the molecule with a chloroformate, such as isobutyl chloroformate, in the presence of a tertiary amine, such as N-methylmorpholine or N-methyl-piperidine, and treating with an azide source, such as sodium azide, hydrazoic acid, trimethylsilylazide, or tetramethylguanidinium azide. The acyl azide may also be formed directly using diphenylphophorylazide in the presence of a tertiary amine. The reaction mixture is then heated at from 40° C. to 100° C. for 0.5 to 6 hours, whereupon the amine HNR$^{14}$R$^{15}$ is added at a temperature at from 23° C. to 100° C. The reaction is conducted in an inert organic solvent such as diethyl ether, tetrahydrofuran, 1,4-dioxane, chloroform, methylene chloride, benzene, or toluene.

In process (g), N-sulfonylation may be carded out using substituted sulfonylhalides in the presence of suitable tert-amines such as trialkylamine, pyridine, and the like (Remers, W. A.; Roth, R. H.; Gibs, G. J.; Weiss, M. J. *J. Org. Chem.* 1971, 36, 1232). Suitable reagents include, but are not limited to benzenesulfonyl halide, p-methyoxybenzene-sulfonyl halide, 2,4,6-trimethylbenzenesulfonyl halide, toluenesulfonyl halide, benzylsulfonyl halide, p-methoxybenzylsulfonyl halide, trifluoromethylsulfonyl halide, phenacylsulfonyl halide, and the like. Some other representative groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-aryl- or alkylsulfonylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (h), N-carbamate fonnations may be carded out using common protecting groups for amino group such as, but not limited to methylcarbamates (cyclopropylmethyl, 9-fluorenylmethyl, and the like), substituted ethylcarbamates (2,2,2-trichloroethyl, 2-phosphonoethyl, 2-methylthioethyl, and the like), substituted propyl and isopropylcarbamates (1,1 -dimethylpropynyl, 1 -methyl- 1 -(4-biphenylyl)ethyl, tert-butyl, phenyl, p-nitrobenzyl, 8-quinolyl, N-hydroxypiperidinyl, benzyl, dimethoxybenzyl, 9-anthrylmethyl, 1-adamantyl, cyclohexyl, tert-amyl, cinnamoyl, isobutyl, N'-p-phenylaminothiocarbonyl, N'-piperidinylcarbonyl, diphenylmethyl, and the like). Preparations of N-carbamates and other groups may be found in volume 3 of *The Peptides*, Gross, E. and Meinhofer, J. Academic Press, 1981 and Protective Groups in Organic Synthesis, Greene, T. W. John Wiley & Sons, New York, Chapter 7, 1981. The N-carbamate formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (i), N-guanidium formation may be carried out using several common reagents such as 1-guanyl-3,5-dimethylpyrazole (Salvadori, S.; Sarto, G. P.; Tomatis, R. Eur. *J. Med. Chem. Chim. Ther.* 1983, 18, 489), 0-methylisourea (Van Nispen, J. W.; Tesser, G. I.; Nivard, R. J. F. *Int. J. Peptide Protein Res.* 1977, 9, 193), and thiourea sulfonylate (Maryanoff, C. A.; Stanzione, R. C.; Plampin, J. N.; Mills, J. E. *J. Org. Chem.* 1986, 51, 1882). The N-guanidinium formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (j), N-sulfenamides may be prepared from an amine and a sulfenyl halide (Davis, F. A.; Nadir, U. K. *Org. Prep. Proc. Int.* 1979, 11, 33; Kobayashi, T.; Iino, K.; Hiraoka, T. *J. Am. Chem. Soc.* 1977, 99, 5505; Zervas, L.; Borovas, D.; Gazis, E. *J. Am. Chem. Soc.* 1963, 85, 3660). Suitable reagents include, but are not limited to benzenesulfenyl halide, o-nitrobenzenesuffenyl halide, 2,4-dinitrosulfenyl halide, pentachlorobenzenesulfenyl halide, 2-nitro-4-methoxybenzenesulfenyl halide, triphenylmethylsulfenyl halide, and the like. Other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-sulfenylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (k), suitable halogenation reagents include, but are not limited to triphenylphosphine with halogens (Verheyden, J.P. H.; Moffatt, J. G. *J. Am. Chem. Soc.* 1964, 86, 2093; Bergman, R. G. *ibid.*, 1969, 91, 7405; Hrubiec, R. T.; Smith, M. B. *J. Org. Chem.*, 1983, 48, 3667), triphenylphosphine with cyanogen halides (Homer, L.; Oediger, H.; Hoffmann, H. *Annalen Chem.* 1959, 626, 26), triphenylphosphine with carbon tetrahalides (Hooz, J.; Gilani, S. S. H. *Can. J. Chem.* 1968, 46, 86; *Chem. Commun.* 1968, 1350), triphenylphosphine with NBS (N-bromosuccinimide)(Schweizer, E. E.; Creasy, W. S.; Light, K. K.; Shaffer, E. T. *J. Org. Chem.* 1969, 34, 212), and triphenylphosphine with hexachloroacetone (Magid, R. M.; Stanley-Fruchey, O.; Johnson, W. L. *Tetrahedron Lett.* 1977, 2999; Magnid, R. M.; Stanley-Fruchey, O.; Johnson, W. L.; Allen, T. G. *J. Org. Chem.* 1979, 44, 359). The halogenation may also be accomplished by other reagents such as mono-or tri-alkylsilyl halides with or without sodium halides (Olah, G. A.; Husain, A.; Singh, B. P.; Mehrota, A. K. *J. Org. Chem.* 1983, 48, 3667; Balme, G.; Fournet, G.; Gore, *J. Tetrahedron Lett.* 1986, 27, 1907), polymer bound trimethylsilyl derivatives (Cainelli, G.; Contento, M.; Manescalchi, F.; Plessi, L.; Panunzio, M. *Synthesis* 1983, 306; Imamoto, T.; Matsumoto, T.; Kusumoto, T.; Yokoyama, M. Synthesis 1983, 460), N,N-dichlorophosphoramidic dichloride (*Chem. Lett.* 1978, 923), phosphorus trihalide-zinc halide (Anderson, Jr. A. G.; Owen, N. E. T.; Freenor, F. J.; Erickson, D. *Synthesis* 1976, 398), diethylaminosulfur trifluoride (Middleton, W. J. *J. Org. Chem.* 1975, 40, 574), triphenoxyphosphonium alkyl halide (Rydon, H. N. *Org. Synth.* 1971, 51, 44; Verheyden, J. P. H.; Moffatt, J. G. *J. Org. Chem.* 1972, 37, 2289), and the like.

The halogenation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (1), phosphonic acid ester formation may be carded out using Michaelis-Arbuzov reactions (Bhattacharya, A. K.; Thyagarajan, G. Chem. Rev. 1981, 81, 415; Bauer, G.; Haegele, G. *Angew. Chem. Int. Ed. Engl.* 1977, 16, 477).

The phosphonic acid ester formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (m), phosphorylation may be carded out using, but is not limited to the 2-halo-2-oxo-1,3,2-dioxaphospholane-triethylamine reaction (Chandrarakumar, N. S.; Hajdu, J. *J. Org. Chem.* 1983, 48, 1197). The phosphorylation may be carried out in a solvent which does not adversely affect the reaction (e.g., benzene, toluene, acetone, dichloromethane, tetrahydrofuran or N,N-dimethylformamide or a mixture thereof). Further, the reaction is preferably conducted in the presence of organic or inorganic bases, as described in process (a), preferably in the presence of organic bases such as triethylamine, pyridine etc. The reaction may be conducted above, at, or below ambient temperature, more preferably from 0° to 50° C.

In process (n), thioether formation may be carried out using, but is not limited to arylor alkylmercaptan in the presence of suitable tert-amines such as trialkylamine, pyridine, and the like. The reaction may also be carried out by a metal-catalyzed thioether formation (Guindon, Y; Frenette, R; Fortin, R.; Rokach, J. *J. Org. Chem.* 1983, 48, 1357), alkali metal salts of aryl- or alkyhnercaptans with a compound of formula I which contains CH—OLg group (OLg is the leaving group). The alkali metal may be selected from sodium, potassium, lithium, and cesium. The thioether formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (o), aryl- or alkyloxythiocarbonylation may be carried out using aryl- or alkyloxythiocarbonylchloride or corresponding halides in the presence of suitable tert-amines such as trialkylamine, pyridine, and the like. The aryl- or alkylthiocarbonylation may be carried out in a solvent which does not adversely affect the reaction (e.g. acetone, dichloromethane, tetrahydrofuran, pyridine, N,N-dimethylformamide etc. or a mixture thereof). The reaction may be conducted above, at, or below ambient temperature.

In process (p), ether formation may be carried out using, for example, aryl-, arylalkyl(heterocyclic)alkylo, (heterocyclic)alkenyl-, (heterocyclic)alkynyl-, loweralkoxycarbonylalkyl-, arylalkoxycarbonylalkyl-, arylalkylcarbonylalkyl-, trialkylsilylcarbonylalkyl-, trialkyl-stannylcarbonylalkyl-, amidocarbonylalkyl-, alkylamidocarbonylalkyl-, dialkylamido-carbonylalkyl-, arylamidocarbonylalkyl-, alkylamidocarbonylalkyl-, heterocyclicamido-carbonylalkyl-, heterocyclic or alkylhalides in the presence of KY-zeolite (Onaka, M.; Kawai, M.; Izumi, Y. *Chem. Lett.* 1983, 1101), polymeric materials (Kimura, Y.; Kirszensztejn, P.; Regen, S. L. *J. Org. Chem.* 1983, 48, 385), nickel-catalysis (Camps, F.; Coll, J.; Moreto, J. M. *Synthesis* 1982, 186; Yamashita. *Synthesis* 1977, 803), arylalkyl—O—p-toluenesulfonate (Dewick, P. M. *Synth. Commun.* 1981, 11,853), potassium or sodium alkoxides (Bates, R. B.; Janda, K. D. *J. Org. Chem.* 1982, 47, 4374), pyridine or other bases (*Chem. Lett.* 1978, 57), tetraalkylammonium halide (Miller, J. M.; So, K. H.; Clark, J. H. Can. *J. Chem.* 1979, 1887), mercury perchlorate (McKillop, A.; Ford, M. E. *Tetrahedron* 1974, 30, 2467), silver triflate or silver oxide (Kuhn, R.; Löw, I.; Trischmann, H. *Chem. Ber.* 1957, 90, 203. Croon, I.; Lindberg, B. Acta Chem. Scand., 1959, 13, 593) or a phase transfer catalyst (McKillop, A.; Fiaud, J. -C.; Hug, R. P. *Tetrahedron* 1974, 30, 1379). The ether formation may also be carried out with dialkyl- or diarylphosphoric acid in the presence of p-toluenesulfonic acid (Kashman, Y. *J. Org. Chem.* 1972, 37, 912), with diazo compounds with tin(H) chloride (Christensen, L. F.; Broom, A. D. *J. Org. Chem.* 1972, 37, 3398), or with 2,2,2-trichloroalkanols in the presence of base (Corey, E. J.; Link, J. O. *J. Am. Chem. Soc.* 1992, 114, 1906; Corey, E. J.; Link, J. O. *Tetrahedron Lett.* 1992, 33,3431 ). Additionally, ether formation may be accomplished with a suitable trichloroacetimidate in the presence of an acid catalyst (Wessel, H. P.; Iversen, T.; Bundle, D. R. *J. Chem. Soc. Perk Trans.* 1985, 1, 2247.) The ether formation may be carried out in a solvent which does not adversely affect the reaction (e.g. acetone, dichloromethane, tetrahydrofuran, pyridine, N,N-dimethylformamide, ether, cyclohexane, etc. or a mixture thereof). The reaction may be conducted above, at, or below ambient temperature.

More specifically, O-alkylation may be carried out using bromoacetic acid derivatives, iodoacetic acid derivatives, trifluoromethanesulfonyloxy acetic acid derivatives, chlorobromo- or iodomethanesulfonic acid derivatives, chlorobromo- or iodoacetyltrimethylsilane and the like in the presence of an appropriate base such as triethylamine, potassium fluoride or silver(I) oxide. The reaction is performed in an inert solvent such as N,N-dimethylformamide, acetonitrile or dichloromethane, preferably between −50° C. and 80° C. Alternatively, alkylation can be carded out using alkyl-, or arylalkyldiazoacetates in the presence of a metal catalyst, for example $Rh(OAc)_2$ in an inert solvent such as dichloromethane preferably between −20° C. and 80° C.

In process (q), N-cyclic imide formations may be carried out using phthalic anhydride (Sasaki, T.; Minamoto, K.; Itoh, H. *J. Org. Chem.* 1978, 43, 2320), o-methoxycarbonylbenzoyl chloride with trialkylamine (Hoogwater, D. A.; Reinhoudt, D. N.; Lie, T. S.; Gunneweg, J. J.; Beyerman, H. C. *Recl. Trav. Chim. Pays-Bas.* 1973, 92, 819), or N-ethoxycarbonylphthalimide (Nefkens, G. H. L.; Tesser, G. I.; Nivard, R. J. F. *Recl. Trav. Chim. Pays-Bas.* 1960, 79, 688). Other groups and reagents may be found in volume 3 of *The Peptides,* Gross, E. and Meinhofer, J. Academic Press, 1981 and *Protective Groups in Organic Synthesis,* Greene, T. W. John Wiley & Sons, New York, Chapter 7, 1981. The N-cyclic imide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (t), deoxygenation may be carried out using, but is not limited to phenoxythiocarbonyl derivative with tributyltin hydride and 2,2-azobis-2-methylpropionitrile (AIBN) (Robins, M. J.; Wilson, J. S.; Hansske, F. *J. Am. Chem. Soc.* 1983, 105, 4059; Barton, D. H. R.; McCombie, S. W. *J. Chem. Soc., Perkin Trans.1* 1975, 1574), or a phenyldithiocarbonyl derivative with tributyltin hydride and AIBN (Hayashi, T.; Iwaoka, T.; Takeda, N.; Ohki, E. *Chem. Pharm. Bull.* 1978, 26, 1786). The deoxygenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (u), suitable oxidizing reagents include activated dialkyl sulfoxides (e.g. dimethylsulfoxide, methylethylsulfoxide) (Mancuso, A. J.; Swern, D. *Synthesis* 1981, 165), organo chromates [e.g. pyridinium chlorochromate (Corey, E. J.; Suggs, J. W. *Tetrahedron Lett.* 1975, 2647; Corey, E. J.; Boger, D. L. *Tetrahedron Lett.* 1978, 2461 ), pyridinium dichromate (Corey, E. J.; Schmidt, G. *Tetrahedron Lett.* 1979, 5, 399), Collins reagent (Collins, J. C.; Hess, W. W.; Frank, F. J. *Tetrahedron Lett.* 1968, 3363)], tetrapropylammonium perruthenate (Griffith, W. P.; Ley, S. V.; Whitcombe, G. P.; White, A. D. *Chem. Commun.* 1987, 1625; Griffith, W. P. *Aldrichimica Acta.* 1990, 23, 13), and the like. The oxidation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (v), suitable alkylating reagents include, but are not limited to aldehydes and ketones in the presence of reducing agents (Hrubowchak, D. M.; Smith, F. X. *Tetrahedron Lett.* 1983, 24, 4951 ), alkyl-, aryl, or arylalkyl halides (Shono, T.; Kashimura, S.; Sawamura, M.; Soejima, T. *J. Org. Chem.* 1988, 53, 907). In the case that the reaction is conducted in the presence of an organic or inorganic bases such as an alkaline earth metal (e.g. calcium, balium, magnesium, thallium etc.), an alkali metal hydride (e.g. sodium hydride, lithium hydride, etc.), an alkali metal hydroxide (e.g. sodium hydroxide, potassium hydroxide, etc.), an alkali metal carbonate (e.g. sodium carbonate, potassium carbonate, etc.), an alkali metal hydrogen carbonate (e.g. sodium hydrogen carbonate, potassium hydrogen carbonate, etc.), an alkali metal alkoxide (e.g. sodium methoxide, sodium ethoxide, thallium ethoxide, potassium tenbutoxide, etc.), an alkali metal alkanoic acid (e.g. sodium acetate, etc.), a trialkylamine (e.g. triethylamine, trimethylamine, etc.), or a pyridine compound (e.g. pyridine, luffdine, picoline, 4-N,N-dimethylaminopyridine, etc.), quinoline, and the like. The alkylation may be carded out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (w), suitable halogenation reagents include, but are not limited to halogens treated by irradiation (sun lamp) for several hours (Heffner, R.; Safaryn, J. E.; Joullie, M. M.; *Tetrahedron Lett.* 1987, 28, 6539) or oxalyl chloride (Evans, D. A.; Dow, R. L.; Shih, T. L.; Takecs, J. M.; Zahler, R. *J. Am. Chem. Soc.* 1990, 112, 5290). The halogenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (x), suitable oxidation reagents include, but are not limited to oxodiperoxymolybdenum(pyridine)-1,3-dimethyl-3,4,5,6-tetrahydro-2(1H )-pyrimidinone (Anderson, J. C.; Smith, S.C. SYNLETT 1990, 2, 107) and oxodiperoxymolybdenum(pyridine)-hexamethylphosphoramide (Vedejs, E. *J. Am. Chem. Soc.* 1974, 96, 5944; Vedejs, E.; Engler, D. A.; Telschow, J. E. *J. Org. Chem.* 1978, 43, 188). The oxidation may be carried out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (aa), suitable olefination reagents include, but are not limited to Wittig reagents (Maecker, M., *Org. React.* 1965, 14, 270; Johnson, A. W., *"Ylid Chemistry,"* Academic Press, New York, 1966) and $CH_2I_2$—Zn—$TiCl_4$ [or $Ti(NEt_2)_4$] reagent (Hibino, J.; Okazoe, T.; Takai, K.; Nozaki, H. *Tetrahedron Lett.* 1985, 26, 5579; Okazoe, T.; Hibino, J.; Takai, K.; Nozaki, H. ibid. 1985, 26, 5581 ). The carbonyl olefination may be carried out in a solvent which does not adversely affect the reaction (e.g. acetone, dichloromethane, tetrahydrofuran, pyridine, N,N-dimethylformamide, etc., or a mixture thereof). The reaction may be conducted at room temperature.

In process (bb), suitable O-acylation reagents include, but are not limited to alkyl, aryl, or arylalkyl acyl halides (Lakhvich, F. A.; Khlebnicova, T. S.; Akhrem, A. A. *Synthesis* 1985, 8,784). The O-acylation may be carried out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (cc), suitable amination reagents include, but are not limited to amino acid derivatives and lower alkyl, aryl, or arylalkyl amines (Winkler, J. D.; Hershberger, P.M.; Springer, J.P. *Tetrahedron Lett.* 1986, 27, 5177). The reaction may be carried out in refluxing in benzene, toluene or a solvent which does not adversely affect the reaction (e.g. tetrahydrofuran, pyridine, N,N-dimethylformamide, etc., or a mixture thereof). The reaction may be conducted at room temperature.

In process (dd), the alkylidene formation may be carried out using, but is not limited to aldehydes and ketones with active methylene compounds. (Schonberg, A.; Singer, E. *Chem. Ber.* 1970, 103, 3871; Chatterjee, S. J. *Chem. Soc.* B, 1969, 725). The alkylidene formation may be carried out in a solvent which does not adversely affect the reaction (eg. acetone, dichloromethane, tetrahydrofuran, pyridine, N,N-dimethylformamide, etc., or a mixture thereof). The reaction may be conducted under cooling to heating.

In process (ee), L may be hydroxy, or a good leaving group (halogen, tosylate, mesylate or triflate, for example). When a precursor compound contains a C(OH)—$CH_2$—C=O group, the elimination of $H_2O$ may be carried out in a solvent which is inert under the reaction conditions (e.g. toluene) with a trace of acid (e.g. toluenesulfonic acid), at a temperature selected from 50° to 100° C. When the precursor compound contains a good leaving group, the elimination may be carried out in the presence of a base (e.g. triethyl amine or potassium carbonate), at a temperature selected from 0° to 100° C.

In process (ff), suitable diamines include phenylene diamine and substituted 1,2-phenyl diamines, 2,3-diaminopyridine, 3,4-diaminopyridine, 4,5-diaminopyridazine, 4,5-diaminopyrimidine and their acid salts, preferably in the presence of tertiary amines (e.g. Nmethylmorpholine). Suitable solvents include methanol, ethanol, propanol, acetonitrile, 2-butanone and N,N-dimethylformamide, and a reaction temperature selected from 50° to 100 ° C.

In process (gg), suitable reagents include sodium borohydride, zinc in acetic acid, sodium triacetoxyborohydride in acetic acid, lithium trialkoxyaluminum hydride in tetrahydrofuran, potassium or lithium tri-sec-butylborohydride in tetrahydrofuran, and borane/t-butylamine complex in a solvent such as methanol or ethanol. The reduction may be conducted at –70° C. to room temperature.

In process (hh), suitable 2-aminothiophenols include substituted 1,2-aminothiophenols, preferably in the presence of tertiary amine (e.g. N-methylmorpholine). Suitable solvents include methanol, ethanol and n-propanol; and the reaction may be conducted at a temperature selected from 50° to 100° C.

In process (ii), the reagent to be used in this reaction may include di(lower)alkyl sulfoxide (e.g. dimethyl sulfoxide, ethyl methyl sulfoxide, propyl methyl sulfoxide, isobutyl methyl sulfoxide, butyl methyl sulfoxide, isobutyl methyl sulfoxide, hexyl methyl sulfoxide, etc). This reaction is usually conducted in the presence of oxalyl chloride, acid chlorides, lower alkanoic anhydride such as acetic anhydride in a conventional solvent that does not adversely influence the reaction such as dichloromethane, acetone, ethyl acetate, tetrahydrofuran, pyridine, N,N-dimethylformamide, etc., followed by the addition of a tertiary amine (e.g. triethyl amine). The reaction may be conducted at –70° C. to room temperature.

In process (jj), the dithiols are lower alkyl dithiols (e.g. ethanedithiol, propanedithiol or butanedithiol) and 1,2-aryl dithiols (e.g. 1,2-benzenedithiol) in the presence of a Lewis acid (e.g. boron trifluoride etherate or lanthanum trichloride) in a conventional solvent that does not adversely influence the reaction such as dichloromethane, tetrahydrofuran or ether. The reaction may be conducted at –70° C. and room temperature.

In process (kk), suitable oxygen-substituted amines include hydroxyl amine, O-alkylhydroxyl amines, and O-arylalkyl hydroxyl amines, for example O-benzyl hydroxyl amine. Suitable solvents include those that do not adversely affect the reaction, for example ethanol or methanol. The reaction is preferably carded out with one equivalent of hydroxyl amine, and at a temperature of 25° to 100° C., more preferably at the reflux temperature of the solvent.

In process (ll), suitable hydrazines include alkylhydrazines (e.g. butylhydrazine), arylhydrazines (e.g. phenylhydrazine), acylhydrazines (e.g. acetylhydrazine), semicarbazides (e.g. t-butyloxycarbonyl hydrazine) and sulfonyl hydrazines (e.g. tosyl hydrazine) in a conventional solvent that does not adversely affect the reaction such as tetrahydrofuran, methanol or ethanol. The reaction may be conducted at 20° to 100° C.

In process (mm), 2-substitutions on the pyrimidine may be hydrogen, alkyl, aryl, hydroxyl, alkoxy, thiol, amino, alkylamino, arylamino, acylamino, carbamylamino, and sulphonylamino groups. The appropriate pyrimidine containing compounds may be prepared according to the methods described in *"The Chemistry of Heterocyclic Compounds, Vol. 16, supplement II,* Chapter II, pp 21–60", D. J. Brown, John Wiley & Sons, 1985.

In process (nn), the furan containing compounds may be prepared according to the method described by Paulissen, R., et. al. in *Tetrahedron Lett.* 1974, 607.

In process (oo), one equivalent of hydroxyl amine hydrochloride and tertiary amine (e.g. N-methylmorpholine) in a conventional solvent that does not adversely affect the reaction such as tetrahydrofuran, methanol, ethanol or isopropanol is used to prepare the compound. The reaction is conducted at 20° to 100° C.

In process (pp), the pyridine containing compounds may be prepared according to the literature: Osman, A. N.; lsmail, M. M.; Barakat, M. A. Rev. *Roum. Chim.* 1986, 31, 615–624; Ried W.; Meyer, A., *Ber. Deutsch. Chem. Ges.* 1957, 90, 2841; Troschutz, R.; Troschultz, J.; Sollhuberkretzer, M. *Arch Pharm.* 1985, 318, 777–781.

In process (qq), a substituted 2-aminothiophenol, a 2-aminophenol or an aromatic 1,2-diamine is used in a conventional solvent that does not adversely affect the reaction such as tetrahydrofuran, ethanol, isopropanol, acetonitrile or N,N-dimethylformamide. The reaction may be conducted at 20° to 100° C.

In process (rr), the keto-substituted furan containing compound may be prepared according to the literature: Williams, P. H. et al, *J. Am. Chem. Soc.* 1960, 82, 4883; E. J. Corey et al., *Chem. Lett.* 1987, 223.

In process (ss), suitable 1-halo-2-nitroaromatics may be substituted 1-fluoro-2-nitrobenzene, o-fluoro-nitropyridines, or o-bromo-nitro-naphthalene, etc. The arylation may be carried out in a solvent which does not adversely affect the reaction (e.g. tetrahydrofuran, N,N-dimethylformamide, dimethoxyethane, diglyme, etc.).

The base used to generate the anion may be isopropyl magnesium chloride, lithium diisopropyl amine or sodium hydride. The reaction may be conducted at a temperature selected from –70° C. to 100° C.

In process (uu), a nitrile oxide may be formed either by oxidation of an aldoxime or dehydration of a nitro compound as described in the following references or literature cited therein: (1) Torssell, K. G. B. "Nitrile Oxides, Nitrones and Nitronates in Organic Synthesis"; VCH Publishers: New York, 1988, p 64; (2) Kim, J. N.; Ryu, E. K. *Synthetic Communications* 1990, 20, 1373; (3) Chow, Y. L.; Shy, Y. Y.; Bakker, B. H.; Pillay, K. S. *Heterocycles* 1989, 29, 2245. The nitrile oxide is placed in the presence of an alpha, betaunsaturated enone in an inert solvent to yield an 2-isoxazolines. Any isomers may subsequently be chomatographically separated.

In process (zz), an isoxazoline may be transformed to the corresponding beta-hydroxy ketone using but is not limited to molybenum hexacarbonyl in wet acetonitfile according to: Baraldi, P. G.; Barco, A.; Benetti, S.; Manfredini, S.; Simoni, D. *Synthesis* 1987, 276. Alternatively, $Ti^{3+}$ may be employed to attain N—O bond cleavage: Das, N. B.; Torssell, K. B. G. *Tetrahedron* 1983, 39, 2227. Additionally, Raney-nickel may also selectively cleave the N—O bond without reducing the imino functionality as described in the following reference and literature cited therein: Torssell, K. G. B. "Nitrile Oxides, Nitrones and Nitronates in Organic Synthesis"; VCH Publishers: New York, 1988, p 16 and 290. During the course of this transformation, a significant amount of dehydration occurs to produce alpha-beta unsaturated enones which may be separated from the beta-hydroxy ketones.

In process (eee), an aryl- or alkylsulfonyl hydrazone may be formed by treatment of a ketone with an aryl- or alkylsulfonyl hydrazide in the presence of an acid catalyst in a solvent suitable for the reaction such as methanol or ethanol at temperatures ranging from ambient to the reflux temperature of the solvent.

In process (hhh), an allylic alcohol may be produced by selective reduction of an alpha-beta unsaturated enone. This is accomplished with but not limited to sodium borohydride in the presence of cerium(IH) chloride heptahydrate in a suitable solvent such as methanol at or near 0° C.

In process (iii), an epoxide may be produced on the central carbonyl of a tricarbonyl moiety by but not limited to excess diazomethane as described in: Fisher, M. J.; Chow, K.; Villalobos, A.; Danishefsky, S. J. *J. Org. Chem.* 1991, 56, 2900–2907.

In process (jjj), liberation of the ester to the acid may be achieved by the cleavage of a suitably substituted ester function. Such a functional group may be benzyl, 2,2,2-trichloroethyl, 9-fluorenylmethyl and the like. These are cleaved by methods well known to those skilled in the art.

In process (kkk), condensation of an amine with the acid may be performed using the mixed or symmetrical anhydride of said acid, or an ester of the acid, preferably activated, such as the ester derived from hydroxybenzotriazole, or the corresponding acylcyanide, acylimidazole, or acylazide of the aforementioned acid.

In process (lll), selective protection of the 32-hydroxyl moiety may be achieved using one of a variety of trialkylsilyl groups. This then leaves exposed a lone secondary alcohol on C-24 for selective inversion, which may be accomplished by activation of the 24-hydroxy as a mesylate, tosylate, etc., followed by inversion with a suitable nucleophile such as water, benzoic acid, formic acid, etc. On the other hand inversion of the unactivated 24-hydroxy group may be achieved using well described Mitsunobu conditions. Liberation of the silyl ether and inverted C-24 acylated hydroxy (if carboxylic acids are used as the nucleophile) is accomplished using methods well known to those skilled in the art. Alternatively, inversion may be accomplished without protection of the 32-hydroxyl group if ascomycin, FK506, or similar compounds are treated with diethylaminosulfur tfifhoride (DAST) in an inert solvent such as methylene chloride.

In process (mmm), condensation of an alkyloxy or substituted alklyoxy carbonyl hydrazine with ascomycin, FK506, similar compounds, or a suitable derivative thereof wherein the C-22 is available as a reactive center, including but not limited to a carbonyl, is performed in an inert solvent such as methanol, ethanol, 2-propanol, etc., in the presence of a catalyst which may be an acid such as formic acid, p-toluenesulfonic acid, or camphorsulfonic acid.

In process (ppp), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, acetonitrile, dioxane, N,N-dimethylformamide, tetrahydrofuran, etc.). The reaction may be carried out in the presence of base (e.g. triethylamine, 4-methylmorpholine or magnesium carbonate, etc.), at a temperature selected from 0° to 100° C. The appropriate thiazole containing compound may be prepared according to *Hantzsch's synthesis* described by: Katritzky, A.R.; Rees, C.W. "Comprehensive Heterocyclic Chemistry"; Pergamon Press: Oxford, 1984, Vol. 6, Part 4B, p.294–299.

In process (qqq), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of base (e.g. triethylamine, 4-methylmorpholine, potassium carbonate or magnesium carbonate, etc.), at a temperature selected from 0° to 100° C.

Suitable amidines include formamidine, alkylamidines, arylamidines and alkylisoureas. Suitable guanidines include N-arylguanidines, N-acylated guanidines and Nsulfonylated guanidines.

In process (rrr), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g., triethylamine, 4-methylmorpholine, potassium carbonate or magnesium carbonate), at a temperature selected from 0° to 100° C.

The amides are primary amides such as formamide, alkylacylamides and arylacylamides.

In process (sss), the organometallic reagent may be a Grignard reagent, an alkyllithium, or an aryllithium reagents.

The selective addition may be carried out in a solvent which does not adversely affect the reaction (e.g., hexanes, ether, tetrahydrofuran, dimethoxyethane or 2-methoxyethyl ether). The reaction may be carried out in the presence of cerium (III) at a temperature selected from −100° C. to 0° C.

In process (ttt), the gamma amino alpha hydroxy carbonyl or a masked gamma amino alpha hydroxy carbonyl of a corresponding compound prepared by process (sss) may have substitutions (e.g. alkyl, aryl groups, etc.) at the alpha and/or beta positions. Furthermore, the amino group may have N-alkyl or aryl substitutions.

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g. triethylamine, 4-methylmorpholine, potassium carbonate or magnesium carbonate, etc.), at a temperature selected from 0° to 100° C.

In process (uuu), the reaction is generally carried out in two steps: first the condensation of an alpha diketone or a masked alpha diketone with an 1,2-diaminoalkane gives a dihydropyrazine. Once the dihydropyrazine has been prepared, it may be oxidized by air in the presence of Pd/C, PtO$_2$ or other catalysts. Metal oxides (e.g. MnO$_2$ or CuO) may also be used for the aromatization.

The condensation and oxidation may be carried out in a solvent which does not adversely affect the reactions (e.g. isopropanol, acetonitrile, dioxane, benzene, toluene, etc.). The reaction may be carried out in the presence of drying agent such as magnesium sulfate or molecular sieves at a temperature selected from 0° C. to 100° C.

In process (vvv), a 1,5-dicarbonyl group or a masked 1,5-dicarbonyl group prepared by process (sss) may have substitutions (e.g. alkyl, aryl groups etc.) at the alpha and/or beta positions. The condensation may be carried out with anhydrous ammonia in a solvent which does not adversely affect the reactions (e.g. liquid ammonia, isopropanol, acetonitrile, dioxane, benzene, toluene, etc.). The reaction may be carried out at a temperature selected from −40° C. to 100° C.

In process (www), a 1,4-dicarbonyl group or a masked 1,4-dicarbonyl group prepared by process (sss) may have substitutions (e.g. alkyl, aryl groups, etc.) at the alpha position.

The condensation and oxidation may be carried out with anhydrous hydrazine in a solvent which does not adversely affect the reactions (e.g. isopropanol, acetonitrile, dioxane, benzene, toluene, etc.). The reaction may be carried out in the presence of a drying agent such as magnesium sulfate or molecular sieves at a temperature selected from 0° C. to 100° C.

In process (xxx), the thiocarbonate formation may be carried out in a solvent which does not adversely affect the reactions (e.g. toluene, acetone, methylene chloride, tetrahydrofuran or pyridine, etc.). The reaction may be carried out in the presence of a base such as triethylamine, pyridine, dimethylaminopyridine and sodium carbonate at a temperature selected from 0° C. to 100° C. The thiocarbonylating reagent may be N,N'-thiocarbonyl-diimidazole, N,N'-thiocarbonylbis(2-pyridone), thiophosgene, or O-phenylthiochloroformate.

In process (yyy), the carbonate formation may be carried out in a solvent which does not adversely affect the reactions (e.g. toluene, acetone, butanone, methylene chloride, tetrahydrofuran or pyridine etc.). The reaction may be carried out in the presence of a base such as triethylamine, pyridine, dimethylaminopyridine and sodium carbonate at a temperature selected from 0° C. to 100° C.

The carbonylating reagent may be N,N'-carbonyldiimidazole, N,N'-carbonyl-bis-( 2-pyridone), phosgene, triphosgene, ethyl chloroformate, ethyl trichloroacetate, or ophenylchloroformate.

In process (zzz), the cyclic phosphonate formation may be carried out by first reacting a diol from a selected compound with phosphorous trichloride followed by the addition of an appropriate alcohol and amine. The alcohol used may be an alkyl alcohol, or an aryl alcohol. The amine used may be primary or secondary. Alternatively, the cyclic phosphonate formation may be carried out by directly reacting the diol from a corresponding compound with an appropriate alkoxyphophoryl dichloride.

The phosphonate formation may be carried out in a solvent which does not adversely affect the reactions (e.g. carbon tetrachloride, chloroform, methylene chloride, toluene, tetrahydrofuran, etc.). The reaction may be carried out in the presence of a base such as triethylamine, pyridine, dimethylaminopyridine, and sodium carbonate at a temperature selected from 0° C. to 100° C.

In process (aaaa), the reduction of thiocarbonate may be carded out in a solvent which does not adversely affect the reactions (e.g., toluene or tetrahydrofuran) at a temperature selected from 0° C. to 100° C.

The reducing agent used may be trimethylphosphite, triethylphosphite, trialkylphosphite or tri-n-butyltin hydride.

In process (bbbb), the reduction of a 1,2-dicarbonyl group of a corresponding compound may be carried out in a solvent which does not adversely affect the reactions (e.g., methanol, ethanol, ethanol, pyridine or N,N-dimethylformamide).

The reducing agents used may be tin amalgam, aluminum amalgam with hydrogen chloride in ethanol, or may be hydrogen sulfide in pyridine or N,N-dimethylformamide.

In process (cccc), the reduction and condensation of a 2-(o-nitrophenyl)-1,3-diketone of a corresponding compound may be carried in a solvent which does not adversely affect the reactions (e.g. ethanol, tetrahydrofuran, ethyl acetate or benzene, etc.).

The reducing agents used may be hydrogen gas over Pd/C, or Pt/C, zinc dust with ammonium chloride, zinc dust with hydrochloric acid at a temperature selected from 0° C. to 100° C.

In process (dddd), triazole formation may be carried out using, but is not limited to an azide derivative with suitable acetylene analogues include diethylacetylene dicarboxylate, dimethylacetylene dicarboxylate, methyl cyanoacetylenecarboxylate, and the likes. The reaction may be conducted above, or below ambient temperature, more preferably from 0° to 50° C.

In process (eeee), pyrrole formation may be carded out using, but is not limited to amine compounds with 1,4-dicarbonyl analogues, such as acetonylacetone, and the likes. Suitable solvents include methanol, ethanol, n-propanol, isopropanol, acetonitrile and N,N-dimethylformanfide. The reaction may be conducted above, or below ambient temperature, more preferably from 50° to 100° C.

In process (ffff), suitable reagents for vicinal hydroxylation include osmium tetraoxide, potassium permanganate, and iodine in conjunction with silver acetate. Osmium tetroxide is preferably used with a regenerating agent such as hydrogen peroxide, alkaline tbutyl hydroperoxide or N-methylmorpholine-N-oxide, and a solvent that does not adversely affect the reaction, for example diethyl ether or tetrahydrofuran. Potassium permanganate is preferably used in mild conditions, for example alkaline aqueous solution or suspensions. Co-solvents such as t-butanol or acetic acid may also be used. Iodine-silver acetate under 'wet' conditions yields ci-diols. Preferably, iodine is used in aqueous acetic acid in the presence of silver acetate. Iodine-silver acetate under 'dry' conditions yields trans-diols. Here, the initial reaction is carried out in the absence of water, and final hydrolysis yields the diol. In each case, the oxidation is preferably carried out at a temperature of 0° to 100° C.

Suitable reagents for the oxidative cleavage of the vicinal diol include lead tetraacetate, phenyliodoso acetate, periodic acid or sodium metaperiodate. Suitable solvents for the first two reagents include benzene and glacial acetic acid. The second two reagents are preferably used in aqueous solution. The reaction is preferably carried out at a temperature of 0° to 100° C.

In process (gggg), suitable reagents for the oxidation of an aldehyde of the corresponding compound may include silver oxide, chromic acid and potassium permanganate. In the presence of a variety of catalysts, oxygen may also be used in converting an aldehyde to a carboxylic acid of a corresponding compound. The catalysts may be palladium or platinum oxide. The air oxidation may be carried out in a solvent which does not adversely affect the reaction (e.g., ethanol, water, acetonitrile, aqueous acetone or pyridine) at a temperature of 0° to 100° C.

In process (hhhh), esters of a corresponding carboxylic acid may be prepared under neutral conditions at room temperature by the reaction of the carboxylic acid with alcohols in the presence of molar amounts of activating reagents such as triphenyl phosphine and diethyl azodicarboxylate, carbodiimides, N,N'-carbonyldiimidazole and 1-methyl-2-halopyridinium iodide. Esters may also be formed by reacting the corresponding carboxylic acid with diazoalkanes in a solvent which does not adversely affect the reaction (e.g., ether, tetrahydrofuran or methylene chloride) at a temperature of from 0° to 100° C.

In process (iiii), the cyclopropanation of the allyl group of a corresponding compound may be carried out with diazoalkanes in a solvent which does not adversely affect the reaction (e.g., ether, methylene chloride or tetrahydrofuran) in the presence of a catalyst such as palladium (II) acetate. The temperature of the reaction is of −15° to 5° C.

In process (jjjj), a pyrrole ring may be produced by reacting a 1,4-dicarbonyl group of a corresponding compound with ammonia, or a substituted amine such as benzylamine or 2-aminoethanol. Suitable solvents include those which do not adversely affect the reaction (e.g., methylene chloride, tetrahydrofuran or dioxane). The reaction is preferably carried out at a temperature of 0° to 100° C.

In process (kkkk), the cyclization of a 1,4-dicarbonyl group of a corresponding compound may be carried out in the presence of a catalytic amount of acid (e.g., acetic acid or arylsulfonic acid). The reaction may be carried out in a solvent which does not adversely affect the reaction (e.g., methylene chloride, ether, benzene or toluene). The reaction is preferably carried out at a temperature of 0° to 60° C.

In process (llll), suitable reagents include air, a palladium (II) halide (e.g. palladium (1I) chloride), in conjunction with a cuprous halide (e.g. cupper (I) chloride). Suitable solvents include those that do not adversely affect the reaction (e.g. DMF and water). The reaction is preferably carried out at a temperature of 0° to 100° C.

In process (nnnn), suitable reducing agents include but are not limited to sodium cyanoborohydride, lithium aluminum hydride, borane-pyridine, or hydrogen in the presence of such catalysts as Raney nickel, platinum, platinum oxide, or palladium. An acidic environment may promote the reduction in some cases, and acids such as hydrochloric acid or p-toluenesulfonic acid may be added for this purpose. The reduction may be carried out in a solvent which does not adversely affect the reaction (e.g. ethanol, ethyl acetate).

In process (oooo), reduction of an oxime to the corresponding amine may be accomplished with but not limited to hydrogenation with a suitable catalyst such as palladium on carbon in a solvent inert to the reaction conditions (e.g. ethanol) at temperatures ranging from 0° to 100° C.

In process (pppp), reduction of an enone to the corresponding saturated ketone may be accomplished with but not limited to hydrogenation with a suitable catalyst such as either palladium on carbon or rhodium on alumina in a solvent inert to the reaction conditions (e.g. methanol, ethanol, isopropanol, ethyl acetate) in a temperature range from −78° to 100° C.

In process (qqqq), isoxazoline formation may be accomplished by, but not limited to the following sets of reaction conditions involving a beta-hydroxy oxime. One possible method is to treat the beta-hydroxy oxime with Martin's sulfurane alehydrating reagent at or near room temperature in a solvent inert to the reaction conditions such as methylene chloride. Alternatively, the beta-hydroxy oxime may be treated with p-toluenesulfonyl chloride in a solvent such as pyridine at temperatures ranging from 0° to 100° C.

In process (rrrr), an intramolecular aldol reaction may be accomplished by, but is not limited to treatment of a carbonyl with a base such as potassium or sodium hydride in a solvent which is inert to the reaction conditions (e.g. tetrahydrofuran or N,N-dimethylformamide) at a temperature range from −78°60 to 150° C.

In process (ssss), a cyclic imine may be formed by, but is not limited to treatment of an alpha,beta-unsaturated enone with the sodium enolate of a glycine ester imine in an inert solvent such as tetrahydrofuran in a temperature range from −78° to 100° C. Upon aqueous workup, the imine hydrolyzes and spontaneously cyclizes to form the cyclic imine.

In process (tttt), a substituted pyrrole may be formed by but is not limited to a 1,3-dipolar cycloaddition between an alpha,beta-unsaturated enone with a glycine ester imine in the presence of a suitable catalyst such as lithium bromide and triethylamine in a solvent inert to the reaction conditions (e.g. tetrahyctrofuran) at or near room temperature.

In process (uuuu), alpha diazoketones can be decomposed by exposure to UV light or by heating. Wolff rearrangements often ensue yielding beta-keto carboxylic acids when run in a solvent mixture containing water, beta-keto esters when run in a solvent containing an alcohol, or beta-keto amides when run in a solvent containing ammonia, a primary or a secondary amine.

Moreover, in process (vvvv), if a beta-keto carboxylic acid is formed, decarboxylation can occur spontaneously or by heating.

In process (yyyy), aryl-, heterocyclic-, or alkyloxycarbonylation may be carried out using aryl-, heterocyclic-, or alkyl- chloroformate in the presence of amines like triethylamine, diisopropylethylamine, pyridine and the like. Alternatively, the reaction may be carried out by reacting the corresponding aryl-OH, heterocyclic-OH or alkyl-OH with —CHOC(O)Cl or —CHOC(O)-(p-nitrophenyl) in a corresponding compound in the presence of amine base. The reaction may be carried out in a solvent which does not adversely affect the reaction (e.g. acetone, dichloromethane, tetrahydrofuran, pyridine and N,N-dimethylformamide, or a mixture thereof). The reaction may be conducted above, at or below ambient temperature.

In process (zzzz) allylic oxidations may be carried out using selenium dioxide with or without a co-oxidant, such as tert-butyl hydroperoxide, in an inert solvent such as tetrahydrofuran, ether, ethylacetate, water, or a combination thereof. The reaction may be conducted at room temperature to 100° C.

The compounds of the present invention are formed by modification of FR-900520 (ascomycin) or one of its congeners (such as FK-506, etc.) by alkylation of the C-32-hydroxyl group with optional modifications exercised at C-18 and/or C-21 and/or C-23 and/or C-24. The compounds, processes and uses of the present invention will be better understood in connection with the following examples, which are intended as an illustration of and certainly not a limitation upon the scope of the invention. Both below and throughout the specification, it is intended that citations to the literature are expressly incorporated by reference.

Example 1

Formula I: R=ethyl: n=1: $R^2=R^{2a}=R^3=R^5=H$:
$R^4=OH$: $R^{1a}=OCH_3$: $R^1=$—$OCH_2C(O)OC_2H_5$
(R-Configuration).

A solution of ascomycin (0.5 g, 0.63 mmol) in dichloromethane (10 mL) containing rhodium(II)acetate dimer (3 mg) was refluxed while ethyl diazoacetate (66 uL, 0.63 mmol) in dichloromethane (1 mL) was added dropwise. After complete addition the reaction was refluxed for 30 minutes and additional ethyl diazoacetate (132 uL, 1.26 mmol) in dichloromethane (1.5 mL) was added dropwise with reflux continuing 30 minutes after complete addition. Solvent was removed in vacuo and the residue purified by HPLC on silica gel eluting with hexane:acetone (3:1). Fractions containing desired product were pooled, concentrated, dissolved in $CCl_4$, and concentrated to constant weight under high vacuum to give the desired product (274 mg) as an oil in 50% yield. IR ($CDCl_3$) 3500, 2930, 1742, 1700, 1645, 1452 cm$^{-1}$; $^{13}$C NMR (125 MHz) delta 9.4, 11.7, 14.1, 14.2, 15.8, 16.2, 20.5, 21.1, 24.2, 24.6, 26.3, 27.6, 30.3, 30.8, 32.7, 32.9, 33.6, 34.6, 36.4, 39.2, 39.7, 43.1, 48.7, 54.7, 56.3, 56.6, 56.9, 57.2, 60.6, 68.5, 70.1, 72.9, 73.7, 75.2, 77.2, 82.8, 83.6, 97.0, 123.1, 129.6, 132.4, 138.7, 164.7, 169.0, 171.1, 196.1, 213.5; MS (FAB) m/z: M+K=916; Anal. calc'd. for $C_{47}H_{75}NO_{14} \cdot 1.0$ $CCl_4$:C, 54.70; H, 7.33; N, 1.36. Found: C, 54.42; H, 7.22; N, 1.26.

Example 2

Formula I: R=ethyl: n=1; $R^2=R^{2a}=R^3=R^5=H$:
$R^4=OH$: $R^{1a}=OCH_3$: $R^1=$—$OCH_2C(O)OCH_2C_6H_5$
(R-Configuration).

The prior procedure was modified using benzyl diazoacetate instead of ethyl diazoacetate. Ascomycin (0.5 g) provided title compound (0.1 g) in 20% yield. mp. 65°–72° C.; IR ($CDCl_3$) 3510, 2930, 1740, 1695, 1642, 1450 cm$^{-1}$; $^{13}$C NMR (125 MHz)delta 9.4, 11.7, 14.1, 15.8, 16.2, 20.4, 21.1, 24.1, 24.5, 26.3, 27.6, 30.3, 30.8, 32.7, 32.8, 34.4, 34.5, 36.3, 39.2, 39.6, 43.1, 48.6, 53.4, 54.6, 56.3, 56.6, 57.1, 66.3, 68.5, 70.1, 72.8, 73.6, 75.1, 76.8, 82.7, 83.6, 96.9, 123.0, 128.3, 128.4, 128.5, 129.5, 132.3, 135.6, 138.7, 164.7, 168.9, 171.0, 196.2, 213.4; MS (FAB) m/z: M+H—$H_2O$=922, M+K=978. Anal. calc'd. for $C_{52}H_{77}NO_{14}$: C, 66.43; H, 8.26; N, 1.49. Found: C, 66.12; H, 8.14; N, 1.41.

Example 3

Formula I: R=ethyl; n=1: $R^2=R^{2a}=R^3 \times R^5=H$:
$R^4=OH$; $R^{1a}=OCH_3$: $R^1=$—$OCH_2C(O)OH$
(R-Configuration).

The resultant product of Example 2 (25 mg, 0.03 mmol) and 10% Pd/C (3 mg), were placed in a flask and the vessel was flushed with nitrogen for 10 min. Methanol (250 uL) was added via syringe, and the reaction stirred under a hydrogen atmosphere (1 atm) for 45 min. The mixture was filtered, the catalyst washed with additional methanol (1 mL), and the solvent removed in vacuo. The resulting residue was partitioned between ethyl acetate (5 mL) and water (5 mL), the organic layer was dried ($MgSO_4$), filtered and concentrated to constant weight, thus producing the title compound (23 mg) as a white powder. MS (FAB) m/z: M+K=888.

Example 4

Formula I: R=ethyl: n=1; $R^2=R^{2a}=R^3=R^5=H$:
$R^4=OH$; $R^{1a}=OCH_3$; $R^1=$—$OCH_2C(O)R^{12}$
(R-Configuration):
$R^{12}=NR^{14}R^{15}$:$R^{14}=H$:$R^{15}=$benzyl.

The product of Example 3 (0.50 g, 0.59 mmol) was dissolved in dichloromethane (5 mL) and the solution cooled to 0° C. 4-Dimethylaminopyridine (DMAP) (14.4 mg, 0.118 mmol) was added followed by 1-(3-dimethylaminopropyl)-3-ethylcarbodiimide hydrochloride (EDAC) (206 mg, 1.07 mmol) then benzylamine (128.3 uL, 1.18 mmol). The reaction was warmed to room temperature and stirred overnight. Ethyl acetate (150 mL) was added and the organic phase washed with I N hydrochloric acid (HCl) (2×150 mL), saturated bicarbonate solution (2×150 mL), and then brine (2×150 mL). The organic layer was dried using anhydrous sodium sulfate($Na_2SO_4$), filtered, and solvent removed in vacuo to give 395.7 mg yellow foam. The crude product was purified by HPLC (30×300 mm silica column) eluting with 2:1 hexane/acetone. Fractions containing product were combined and solvent removed in vacuo to give the title compound (273.2 mg, 49% yield) as a white solid: MS (FAB) m/z: (M+K)=977.

Example 5

Formula I: R=ethyl: n=1; $R^2=R^{2a}=R^3=R^5=H$;
$R^4=OH$; $R^{1a}=OCH_3$; $R^1=$—$OCH_2C(O)R^{12}$
(R-Configuration); $R^{12}=NR^{14}R^{15}$: $R^{14}=CH_3$:
$R^{15}=$benzyl.

The resultant product of Example 3 (0.8 g, 0.94 mmol) was dissolved in THF (3 mL) and the solution cooled to 0° C. before adding N-methylmorpholine (103.4 uL, 0.94 mmol) followed by isobutyl chloroformate (122.2 uL, 0.94 mmol). The resulting suspension was stirred for 20 minutes at 0° C. after which N-methylbenzylamine (243 uL, 1.88 mmol) was added. Stirring was continued overnight as the ice melted. The reaction mixture was loaded onto silica (40 mL) in a fritted funnel then eluted with dichloromethane (100 mL), 2:1 hexane/acetone (200 mL), 1:1 hexane/acetone (200 mL), and acetone (100 mL). Fractions containing product were combined and solvent removed in vacuo to give 0.64 g yellow foam. The crude product was further purified by HPLC (30×300 mm silica column) eluting with 1.5:1 hexane/acetone to provide the title compound (523 mg, 58% yield) as a white foam. MS (FAB)m/z: (M+K)=991.

Example 6

Formula I: R=ethyl; n=1; $R^2=R^{2a}=R^3=R^5$=H:
$R^4$=OH; $R^{1a}$=OCH$_3$; $R^1$=—OCH$_2$C(O)R$^{12}$
(R-Configuration): $R^{12}$=NR$^{14}$R$^{15}$; $R^{14}$=R$^{15}$=H.

The crude isolate from Example 81 (1.5 g, ~1.2 mmol) was dissolved in THF (4 mL) and the solution cooled to 0° C. before adding N-methylmorpholine (129.4 uL, 1.2 mmol) followed by isobutyl chloroformate (152.8 uL, 0.59 mmol). The resulting suspension was stirred for 20 minutes at 0° C. after which ammonium hydroxide (14.8M, 159.2 uL, 2.4 mmol) was added.

Stirring was continued overnight as the ice melted. The reaction mixture was loaded onto silica (80 mL) in a fritted funnel then eluted with dichloromethane (200 mL), 2:1 hexane/acetone (400 mL), 1:1 hexane/acetone (400 mL), and acetone (200 mL). Fractions containing product were combined and solvent removed in vacuo to give 358 mg yellow foam. The crude product was further purified by RP-HPLC (Rainin Dynamax 41.4 mm phenyl column) eluting with a gradient of 20% methanol/water and acetonitrile to provide the title compound (188.7 mg, 19% yield) as a white foam. MS (FAB)m/z: (M+K)=887.

Example 7

Formula I: R=ethyl; n=1; $R^2=R^{2a}=R^3=R^5$=H:
$R^4$=OH; $R^{1a}$=OCH$_3$; $R^1$=—OCH$_2$C(O)R$^{12}$
(R-Configuration); R12=NR$^{14}$R$^{15}$; $R^{14}$=H;
$R^{15}$=CH$_3$.

The product of Example 3 is activated as in Example 5 and then treated with methylamine instead of N-methylbenzylamine to provide the title compound.

Example 8

Formula I: R=ethyl; n=1; $R^2=R^{2a}=R^3=R^5$=H;
$R^4$=OH; $R^{1a}$=OCH$_3$; $R^1$=—OCH$_2$C(O)R$^{12}$
(R-Configuration); $R^{12}$=NR$^{14}$R$^{15}$; $R^{14}$=H:R$^{15}$=CH$_3$.

The product of Example 3 is activated as in Example 5 and then treated with dimethylamine instead of N-methylbenzylamine to provide the title compound.

Example 9

Formula I: R=ethyl; n=1; $R^2=R^{2a}=R^3=R^5$=H;
$R^4$=OH; $R^{1a}$=OCH$_3$; $R^1$=—OCH$_2$C(O)R$^{12}$
(R-Configuration); $R^{12}$=NR$^{14}$R$^{15}$; $R^{14}$=H;
$R^{15}$=ethyl.

The product of Example 3 is activated as in Example 5 and then treated with ethylamine instead of N-methylbenzylamine to provide the title compound.

Example 10

Formula I: R=ethyl; n=1; $R^2=R^{2a}=R^3=R^5$=H;
$R^4$=OH; $R^{1a}$=OCH$_3$; $R^1$=—OCH$_2$C(O)R$^{12}$
(R-Configuration); $R^{12}$=NR$^{14}$R$^{15}$; $R^{14}$=CH$_3$;
$R^{15}$=ethyl.

The product of Example 3 is activated as in Example 5 and then treated with N,N-methyl,ethylamine instead of N-methylbenzylamine to provide the title compound.

Example 11

Formula I: R=ethyl; n=1; $R^2=R^{2a}=R^3=R^5$=H;
$R^4$=OH; $R^{1a}$=OCH$_3$; $R^1$=—OCH$_2$C(O)R$^{12}$
(R-Configuration); $R^{12}$=NR$^{14}$R$^{15}$; $R^{14}$=H;
$R^{15}$=—CH$_2$CH$_2$CH$_3$.

The product of Example 3 is activated as in Example 5 and then treated with propylamine instead of N-methylbenzylamine to provide the title compound.

Example 12

Formula I: R=ethyl; n=1; $R^2=R^{2a}=R^3=R^5$=H:
$R^4$=OH; $R^{1a}$=OCH$_3$; $R^1$=—OCH$_2$C(O)R$^{12}$
(R-Configuration): $R^{12}$=NR$^{14}$R$^{15}$; $R^{14}$=CH$_3$;
$R^{15}$=—CH$_2$CH$_2$CH$_3$.

The product of Example 3 is activated as in Example 5 and then treated with N,N-methyl,propylamine instead of N-methylbenzylamine to provide the title compound.

Example 13

Formula I: R=ethyl; n=1; $R^2=R^{2a}=R^3=R^5$=H:
$R^4$=OH; $R^{1a}$=OCH$_3$; $R^1$=—OCH$_2$C(O)R$^{12}$
(R-Configuration); $R^{12}$=NR$^{14}$R$^{15}$; $R^{14}$=H:
$R^{15}$=—CH(CH$_3$)$_2$.

The product of Example 3 is activated as in Example 5 and then treated with 2-aminopropane instead of N-methylbenzylamine to provide the title compound.

Example 14

Formula I: R=ethyl: n=1: $R^2=R^{2a}=R^3=R^5$=H:
$R^4$=OH; $R^{1a}$=OCH$_3$; $R^1$=—OCH$_2$C(O)R$^{12}$
(R-Configuration): $R^{12}$=NR$^{14}$R$^{15}$; $R^{14}$=CH$_3$; $R^{15}$=—CH(CH$_3$)$_2$.

The product of Example 3 is activated as in Example 5 and then treated with N,N-methyl, 2-propylamine instead of N-methylbenzylamine to provide the title compound.

Example 15

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$:R$^{14}$=H;
$R^{15}$=cyclopropyl.

The product of Example 3 is activated as in Example 5 and then treated with cyclopropylamine instead of N-methylbenzylamine to provide the title compound.

Example 16

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=H;
$R^{15}$=—CH$_2$CH$_2$CH$_2$CH$_3$.

The product of Example 3 is activated as in Example 5 and then treated with n-butylamine instead of N-methylbenzylamine to provide the title compound.

Example 17

Formula I: R=ethyl: n=1: $R^2=R^{2a}=R^3=R^5=H$: $R^4=OH$: $R^{1a}=OCH_3$; $R^1=$—$OCH_2C(O)R^{12}$ (R-Configuration): $R^{12}=NR^{14}R^{15}$; $R^{14}=CH_3$; $R^{15}=$—$CH_2CH_2CH_2CH_3$.

The product of Example 3 is activated as in Example 5 and then treated with N,N-methylbutylamine instead of N-methylbenzylamine to provide the title compound.

Example 18

Formula I: R=ethyl: n=1: $R^2=R^{2a}=R^3=R^5=H$: $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}=$—$CH_2CH(CH_3)_2$.

The product of Example 3 is activated as in Example 5 and then treated with isobutylamine instead of N-methylbenzylamine to provide the title compound.

Example 19

Formula I: R=ethyl: n=1: $R^2=R2a=R^3=R^5=H$: $R^4=OH$: $R^{1a}=OCH_3$; $R^1=$—$OCH_2C(O)R^{12}$ (R-Configuration): $R^{12}=NR^{14}R^{15}$; $R^{14}=CH_3$; $R^{15}=$—$CH_2CH(CH_3)_2$.

The product of Example 3 is activated as in Example 5 and then treated with N,N-methyl,isobutylamine instead of N-methylbenzylamine to provide the title compound.

Example 20

Formula I: R=ethyl; n1; $R^2=R^{2a}=R^3=R^5=H$; $R^4=OH$; $R^{1a}=OCH_3$; $R^1=$—$OCH_2C(O)R^{12}$ (R-Configuration); $R^{12}=NR^{14}R^{15}$; $R^{14}=H$; $R^{15}=$cyclobutyl.

The product of Example 3 is activated as in Example 5 and then treated with cyclobutylamine instead of N-methylbenzylamine to provide the title compound.

Example 21

Formula I: R=ethyl: n=1: $R^2=R^{2a}=R^3=R^5=H$: $R^4=OH$: $R^{1a}=OCH_3$; $R^1=$—$OCH_2C(O)R^{12}$ (R-Configuration); $R^{12}=NR^{14}R^{15}$; $R^{14}=H$; $R^{15}=$—$CH_2CH_2CH_2CH_2CH_3$.

The product of Example 3 is activated as in Example 5 and then treated with pentylamine instead of N-methylbenzylamine to provide the title compound.

Example 22

Formula I: R=ethyl: n=1: $R^2=R^{2a}=R^3=R^5=H$: $R^4=OH$: $R^{1a}=OCH_3$; $R^1=$—$OCH_2C(O)R^{12}$ (R-Configuration): $R^{12}=NR^{14}R^{15}$; $R^{14}=CH_3$; $R^{15}=$—$CH_2CH_2CH_2CH_2CH_3$.

The product of Example 3 is activated as in Example 5 and then treated with N,N-methyl,pentylamine instead of N-methylbenzylamine to provide the title compound.

Example 23

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}=CH_2CH_2CH_2(CH_3)_2$.

The product of Example 3 is activated as in Example 5 and then treated with 3-methylbutylamine instead of N-methylbenzylamine to provide the title compound.

Example 24

Formula I: R=ethyl: n=1: $R^2=R^{2a}=R^3=R^5=H$: $R^4=OH$; $R^{1a}=OCH_3$; $R^1$——$OCH_2C(O)R^{12}$ (R-Configuration); $R^{12}=NR^{14}R^{15}$; $R^{14}=CH_3$; $R^{15}=$—$CH_2CH_2CH_2(CH_3)_2$.

The product of Example 3 is activated as in Example 5 and then treated with N,N-methyl,3methylbutylamine instead of N-methylbenzylamine to provide the title compound.

Example 25

Formula I: R=ethyl: n=1: $R^2=R^{2a}=R^3=R^5=H$: $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}=$cyclopentyl.

The product of Example 3 is activated as in Example 5 and then treated with cyclopentylamine instead of N-methylbenzylamine to provide the title compound.

Example 26

Formula I: R=ethyl: n=1: $R^2=R^{2a}=R^3=R^5=H$: $R^4=OH$; $R^{1a}=OCH_3$; $R^1=$—$OCH_2C(O)R^{12}$ (R-Configuration): $R^{12}=NR^{14}R^{15}$; $R^{14}=H$: $R^{15}=$—$CH_2CH_2CH_2CH_2CH_2CH_3$.

The product of Example 3 is activated as in Example 5 and then treated with n-hexylamine instead of N-methylbenzylamine to provide the title compound.

Example 27

Formula I: R=ethyl; n=1; $R^2=R^{2a}=R^3=R^5=H$; $R^4=OH$; $R^{1a}=OCH_3$; $R^1=$—$OCH_2C(O)R^{12}$(R-Configuration): $R^{12}=NR^{14}R^{15}$: $R^{14}=CH_3$; $R^{15}=$—$CH_2CH_2CH_2CH_2CH_2CH_3$.

The product of Example 3 is activated as in Example 5 and then treated with N,N-methyl,hexylamine instead of N-methylbenzylamine to provide the title compound.

Example 28

Formula I: R=ethyl; n=1; $R^2=R^{2a}=R^3=R^5=H$; $R^4=OH$; $R^{1a}=OCH_3$; $R^1=$—$OCH_2C(O)R^{12}$ (R-Configuration); $R^{12}=NR^{14}R^{15}$; $R^{14}=H$: $R^{15}=$cyclohexyl.

The product of Example 3 was activated as in Example 5 and then treated with cyclohexylamine instead of N-methylbenzylamine to provide the title compound. MS (FAB) m/z: M+H=931.

Example 29

Formula I: R=ethyl; n=1; $R^2=R^{2a}=R^3=R^5=H$; $R^4=OH$; $R^{1a}=OCH_3$; $R^1=-OCH_2C(O)R^{12}$ (R-Configuration); $R^{12}=NR^{14}R^{15}$; where $R^{14}$ and $R^{15}$ taken together=$-CH_2CH_2OCH_2CH_2-$, thus forming a six membered ring incorporating the nitrogen to which they are attached.

The product of Example 3 was activated as in Example 4 and then treated with morpholine instead of benzylamine to give the title compound. MS (FAB)m/z: (M+K)=957.

Example 30

Formula I: R=ethyl; n=1; $R^2=R^{2a}=R^3=R^5=H$; $R^4=OH$; $R^{1a}=OCH_3$; $R^1=-OCH_2C(O)R^{12}$ (R-Configuration); $R^{12}=NR^{14}R^{15}$; $R^{14}=H$; $R^{15}=-CH_2CH_2OH$.

The product of Example 3 was activated as in Example 4 and then treated with 2-aminoethanol instead of benzylamine to give the title compound. MS (FAB)m/z: (M+K)=931.

Example 31

Formula I: R=ethyl; n=1; $R^2=R^{2a}=R^3=R^5=H$; $R^4=OH$; $R^{1a}=OCH_3$; $R^1=-OCH_2C(O)R^{12}$ (R-Configuration); $R^{12}=NR^{14}R^{15}$; $R^{14}=H$; $R^{15}=-CH_2CH_2CH_2OH$.

The product of Example 3 was activated as in Example 4 and then treated with 3-aminopropanol instead of benzylamine to give the title compound. MS (FAB)m/z: (M+K)=945.

Example 32

Formula I: R=ethyl; n=1; $R^2=R^2a=R^3=R^5=H$; $R^4=OH$; $R^{1a}=OCH_3$; $R^1=-OCH_2C(O)R^{12}$ (R-Configuration); $R^{12}=NR^{14}R^{15}$; $R^{14}=H$; $R^{15}=-CH_2CH_2CH_2CH_2OH$.

The product of Example 3 was activated as in Example 5 and then treated with 4-aminobutanol instead of N-methylbenzylanfine to give the title compound. MS (FAB)m/z: (M+K)=959.

Example 33

Formula I: R=ethyl; n=1; $R^2=R^{2a}=R^3=R^5=H$; $R^4=OH$; $R^{1a}=OCH_3$; $R^1=-OCH_2C(O)R^{12}$(R-Configuration): $R^{12}=NR^{14}R^{15}$; $R^{14}=H$; $R^{14}=-CH_2CH_2CH_2CH_2CH_2OH$.

The product of Example 3 is activated as in Example 5 and then treated with 5-hydroxypentylamine instead of N-methylbenzylamine to provide the title compound.

Example 34

Formula I: R=ethyl; n=1; $R^2=R^{2a}=R^3=R^5=H$; $R^4=OH$; $R^{1a}=OCH_3$; $-OCH_2C(O)R^{12}$ (R-Configuration); $R^{12}=NR^{14}R^{15}$; $R^{14}=H$; $R^{15}=-CH_2CH_2NH_2$.

The product of Example 3 is activated as in Example 5, and then treated with 1,2-diaminoethane instead of N-methylbenzylamine to provide the title compound.

Example 35

Formula I: R=ethyl; n=1; $R^2=R^{2a}=R^3=R^5=H$; $R^4=OH$; $R^{1a}=OCH_3$; $-OCH_2C(O)R^{12}$(R-Configuration): $R^{12}=NR^{14}R^{15}$; $R^{14}=H$; $R^{15}=-CH_2CH_2CH_2NH_2$.

The product of Example 3 is activated as in Example 5, and then treated with 1,3-diaminopropane instead of N-methylbenzylamine to provide the title compound.

Example 36

Formula I: R=ethyl; n=1; $R^2=R^{2a}=R^3=R^5=H$; $R^4=OH$; $R^{1a}=OCH_3$; $-OCH_2C(O)R^{12}$ (R-Configuration); $R^{12}=NR^{14}R^{15}$; $R^{14}=H$; $R^{15}=-CH_2CH_2CH_2CH_2NH_2$.

The product of Example 3 is activated as in Example 5, and then treated with 1,4-diaminobutane instead of N-methylbenzylamine to provide the title compound.

Example 37

Formula I: R=ethyl; n=1; $R^2=R^{2a}=R^3=R^5=H$; $R^4=OH$; $R^{1a}=OCH_3$; $-OCH_2C(O)R^{12}$ (R-Configuration); $R^{12}=NR^{14}R^{15}$; $R^{14}=H$; $R^{15}=-CH_2CH_2CH_2CH_2CH_2NH_2$.

The product of Example 3 is activated as in Example 5, and then treated with 1,5-diaminopentane instead of N-methylbenzylamine to provide the title compound.

Example 38

Formula I: R=ethyl; n=1; $R^2=R^{2a}=R^3=R^5=H$; $R^4=OH$; $R^{1a}=OCH_3$; $-OCH_2C(O)R^{12}$ (R-Configuration); $R^{12}=NR^{14}R^{15}$; $R^{14}=H$; $R^{15}=-CH_2CO_2CH_2Ph$.

The product of Example 3 was activated as in Example 4 and then treated with glycine benzyl ester instead of benzylamine to give the title compound. MS (FAB)m/z: (M+K)=1035.

Example 39

Formula I: R=ethyl; n=1; $R^2=R^{2a}=R^3=R^5=H$; $R^4=OH$; $R^{1a}=OCH_3$; $R^1=-OCH_2C(O)R^{12}$ (R-Configuration): $R^{12}=NR^{14}=R^{15}$; $R^{14}=H$; $R^{15}=-CH_2CO_2H$.

The title compound was synthesized in the manner described in Example 3 substituting the product from Example 38 for the product from Example 2. MS (FAB)m/z: (M+K)=945.

Example 40

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=H: $R^{15}$=
—CH$_2$CH$_2$CO$_2$CH$_2$Ph.

The product of Example 3 was activated as in Example 4 and then treated with beta-alanine benzyl ester instead of benzylamine to give the title compound. MS (FAB)m/z: (M+K)=1049.

Example 41

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$=R$^{15}$; $R^{14}$=H: $R^{15}$=
—CH$_2$CH$_2$CO$_2$H.

The title compound was synthesized in the manner described in Example 3 substituting the product from Example 40 for the product from Example 2. MS (FAB)m/z: (M+K)=959.

Example 42

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$=R$^{15}$; $R^{14}$=H: $R^{15}$=
—CH(CH$_3$)CO$_2$H (R configuration).

The product of Example 3 is activated as in Example 5, and then treated with (R)-2-aminopropanoic acid instead of N-methylbenzylamine to provide the title compound.

Example 43

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$=R$^{15}$; $R^{14}$=H: $R^{15}$=
—CH9CH$_3$)CO$_2$H (S configuration).

The product of Example 3 is activated as in Example 5, and then treated with (S)-2-aminopropanoic acid instead of N-methylbenzylamine to provide the title compound.

Example 44

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$=R$^{15}$; $R^{14}$=H: $R^{15}$=
—CH(CH3)CONHCH(CH3)CONHCH(CH3)CO2H
(all chiral centers in R$^{15}$ are R configuration).

The product of Example 3 is activated as in Example 5, and then treated with D-alaninyl-D-alaninyl-D-alanine instead of N-methylbenzylamine to provide the title compound.

Example 45

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=H:
$R^{15}$=3-phenyl-phenyl.

The product of Example 3 is activated as in Example 5 and then treated with 3-biphenylamine instead of N-methylbenzylamine to give the title compound.

Example 46

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=H:
$R^{15}$=3-phenyl-phenyl.

The product of Example 3 is activated as in Example 5 and then treated with N,N-(ethanol-2 -yl)-(3-biphenyl)-amine instead of N-methylbenzylamine to give the title compound.

Example 47

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=H:
$R^{15}$=—CH$_2$CH$_2$N(CH$_3$)(CH$_2$CH$_2$OH): $R^{15}$=phenyl.

The product of Example 3 is activated as in Example 5 and then treated with N-phenyl-N'-methyl-N'-(ethanol-2-yl)-ethyldiamine instead of N-methylbenzylamine to give the title compound.

Example 48

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$;
$R^{14}$=CH$_2$CH$_2$N(CH$_3$)$_2$; $R^{15}$=phenyl.

The product of Example 3 is activated as in Example 5 and then treated with N-phenyl-N',N'-dimethyl-ethyldiamine instead of N-methylbenzylamine to give the title compound.

Example 49

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$;
$R^{14}$=CH$_2$(3-pyridyl): $R^{15}$=CH$_2$(3-pyridyl).

The product of Example 3 was activated as in Example 5 and then treated with 3,3'-dipipicolylamine instead of N-methylbenzylamine to give the title compound. MS (FAB) m/z: M+K=1069.

Example 50

Formula I: R=ethyl; n=1; $R^2=R^{2a}=R^3=R^5$=H:
$R^4$=OH: $R^{1a}$=OCH$_3$; $R^1$=—OCH$_2$C(O)R$^{12}$
(R-Configuration): $R^{12}$=NR$^{14}$R$^{15}$; $R^{14}$=cyclohexyl;
$R^{15}$=cyclohexyl.

The product of Example 3 is activated as in Example 5 and then treated with dicyclohexylamine instead of N-methylbenzylamine to give the title compound.

Example 51

Formula I: R=ethyl: n=1: $R^2=R^{2a}=R^3=R^5$=H;
$R^4$=OH; $R^{1a}$=OCH$_3$; $R^1$=—OCH$_2$C(O)R$^{12}$
(R-Configuration): $R^{12}$=NR$^{14}$R$^{15}$; $R^{14}$=H;
$R^{15}$=NH-(4-morpholinyl).

The product of Example 3 was activated as in Example 5 and then treated with 1 equivalent of 4-aminomorpholine and 0.1 equivalents of 4-dimethylaminopyridine instead of N-methylbenzylamine to give the title compound. MS (FAB) m/z: M+K=972.

Example 52

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-thiomorpholinyl.

The product of Example 3 was activated as in Example 5 and then treated with thiomorpholine instead of N-methylbenzylamine to give the title compound. MS (FAB) m/z: M+K=973.

Example 53

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-$CF_3$-phenyl.

The product of Example 3 was activated as in Example 4 and then treated with 4-aminobenzotrifluoride instead of benzylamine to give the title compound. MS (FAB)m/z: (M+K)=1031.

Example 54

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-F-phenyl.

The product of Example 3 was activated as in Example 4 and then treated with 4-fluoroaniline instead of benzylamine to give the title compound. MS (FAB)m/z: (M+K)=981.

Example 55

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-(4-morpholino)-phenyl.

The product of Example 3 was activated as in Example 4 and then treated with 4-morpholinoaniline instead of benzylamine to give the title compound. MS (FAB)m/z: (M+K)=1048.

Example 56

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-HO-phenyl.

The product of Example 3 was activated as in Example 5 and then treated with p-aminophenol instead of Nomethylbenzylamine to give the title compound. MS (FAB)m/z: (M+K)=979.

Example 57

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=3-pyridyl.

The product of Example 3 was activated as in Example 5 and then treated with 3-aminopyridine instead of N-methylbenzylamine to give the title compound. MS (FAB)m/z: (M+K)=964.

Example 58

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=4-pyridyl.

The product of Example 3 was activated as in Example 5 and then treated with 4-aminopyridine instead of N-methylbenzylamine to give the title compound. MS (FAB)m/z: (M+K)=964.

Example 59

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}$=2-pyridyl.

The product of Example 3 was activated as in Example 5 and then treated with 2-aminopyridine instead of N-methylbenzylamine to give the title compound. MS (FAB)m/z: (M+K)=964.

Example 60

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}=CH_2CH_2OH$.

The product of Example 3 was activated as in Example 5 and then treated with 2-(methylamino)ethanol instead of N-methylbenzylamine to give the title compound. MS (FAB)m/z: (M+K)=945.

Example 61

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}=NR^{14}R^{15}$; $R^{14}=H$; $R^{15}=NHCO_2CH_3$.

The product of Example 3 is activated as in Example 5 and then treated with methylcarbazate instead of N-methylbenzylamine to give the title compound.

Example 62

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}$=L-prolinocarboxamide.

The product of Example 3 is activated as in Example 5 and then treated with L-prolinecarboxamide instead of N-methylbenzylamine to give the title compound.

Example 63

Formula I: R=ethyl: n=1: $R^2=R^{2a}=R^3=R^5=H$; $R^4=OH$; $R^{1a}=OCH_3$; $R^1=$—$OCH_2C(O)R^{12}$ (R-Configuration): $R^{12}$= D-prolinocarboxamide.

The product of Example 3 is activated as in Example 5 and then treated with D-Prolinecarboxamide instead of N-methylbenzylamine to give the title compound.

Example 64

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}$=L-prolinol.

The product of Example 3 is activated as in Example 5 and then treated with L-prolinol instead of N-methylbenzylamine to give the title compound.

Example 65

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}$=D-prolinol.

The product of Example 3 is activated as in Example 5 and then treated with D-prolinol instead of N-methylbenzylamine to give the title compound.

Example 66

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^8NR^6R^7$;
$R^8=CH_2CH_2OH$; $R^6=H$, $R^7=CO_2CH_3$.

The product of Example 3 is activated as in Example 5 and then treated with N-(ethanol- 2-yl)-N'-carbomethoxyhydrazine instead of N-methylbenzylamine to give the title compound.

Example 67

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$; $R^{14}=H$;
$R^{15}$=3-(phenylethynyl)phenyl.

The product of Example 3 is activated as in Example 5 and then treated with 3-phenylethynylaniline instead of N-methylbenzylamine to give the title compound.

Example 68

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$;
$R^{14}=CH_2CH_2CH_2OH$; $R^{15}$=4-fluorophenyl.

The product of Example 3 is activated as in Example 5 and then treated with 3-(4-fluoroanilino)-1-propanol instead of N-methylbenzylamine to give the title compound.

Example 69

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$;
$R^{14}=CH_2CH_2CH_2OCOCH_2CH_2CO_2H$;
$R^{15}$=4-fluorophenyl.

The product of Example 68 is treated with succinic anhydride, as published in *Tetrahedron Letts.* 1989, 30, 5045–48, to give the title compound.

Example 70

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$; $R^{14}$ and $R^{15}$ are taken together as the following diradical,
$-CH_2CH_2C(OCH_2CH_2O)CH_2CH_2-$.

The product of Example 3 was activated as in Example 5 and then treated with 1,4-dioxa-8-azaspiro[4.5]decane instead of N-methylbenzylamine to give the title compound. MS (FAB) m/z: M+K=1013.

Example 71

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^8NR^6R^7$; $R^8=H$; $R^6=H$;
$R^7$=CO-(4-pyridyl).

The product of Example 3 was activated as in Example 5 and then treated with isonicotinic acid hydrazide instead of N-methylbenzylamine to give the title compound. MS (FAB) m/z: M+K= 1007.

Example 72

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$; $R^{14}=H$;
$R^{15}$=3-fluorophenyl.

The product of Example 3 was activated as in Example 5 and then treated with m-fluoroaniline instead of N-methylbenzylamine to give the title compound. MS (FAB) m/z: M+2K-H=1045.

Example 73

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$; $R^{14}=H$;
$R^{15}$=3-hydroxy-phenyl.

The product of Example 3 was activated as in Example 5 and then treated with m-aminophenol instead of N-methylbenzylamine to give the title compound. MS (FAB) m/z: M+K=979.

Example 74

Formula I: R=ethyl: n=1: $R^2=R^{2a}=R^3=R^5=H$;
$R^4=OH$; $R^{1a}=OCH_3$; $R^1=\!\!-\!\!OCH_2C(O)R^{12}$
(R-Configuration): $R^{12}=NR^{14}R^{15}$; $R^{14}$ and $R^{15}$ are taken together as the following diradical;
$-CH_2CH_2-NCH_3-CH_2CH_2-$.

The product of Example 3 was activated as in Example 5 and then treated with N-methylpiperazine instead of N-methylbenzylamine to give the title compound. MS (FAB) m/z: M+H =932.

Example 75

Formula I: R=ethyl: n=1: $R^2=R^{2a}=R^3=R^5=H$;
$R^4$=OH; $R^{1a}$=OCH$_3$; $R^1$=—OCH$_2$C(O)R$^{12}$
(R-Configuration): $R^{12}$=NR$^{14}$R$^{15}$; R$^{14}$=H;
$R^{15}$=6-(1,4-benzodioxanyl)—.

The product of Example 3 is activated as in Example 5 and then treated with 1,4-benzodioxan-6-amine instead of N-methylbenzylamine to give the title compound.

Example 76

Formula I: R=ethyl: n=1: $R^2=R^{2a}=R^3=R^5=H$;
$R^4$=OH; $R^{1a}$=OCH$_3$;
$R^1$=—OCH$_2$C(O)R$^{12}$(R-Configuration);
$R^{12}$=NR$^{14}$R$^{15}$; R$^{14}$=H;
$R^{15}$=3,4-methylenedioxyphenyl—.

The product of Example 3 is activated as in Example 5 and then treated with 3,4-(methylenedioxy)-aniline instead of N-methylbenzylamine to give the title compound.

Example 77

Formula I: R=ethyl: n=1: $R^2=R^{2a}=R^3=R^5=H$;
$R^4$=OH; $R^{1a}$=OCH$_3$;
$R^1$=—OCH$_2$C(O)R$^{12}$(R-Configuration);
$R^{12}$=NR$^{14}$R$^{15}$; R$^{14}$=H; R$^{15}$=1-naphthalenyl.

The product of Example 3 is activated as in Example 5 and then treated with 1-naphthylamine instead of N-methylbenzylamine to give the title compound.

Example 78

Formula I: R=ethyl: n=1: $R^2=R^{2a}=R^3=R^5=H$;
$R^4$=OH; $R^{1a}$=OCH$_3$;
$R^1$=—OCH$_2$C(O)R$^{12}$(R-Configuration);
$R^{12}$=NR$^{14}$R$^{15}$; where R$^{14}$ and R$^{15}$ taken
together=—CH$_2$CH$_2$CH$_2$CH$_2$—, thus forming a
five membered ring incorporating the nitrogen to
which they are attached.

The product of Example 3 is activated as in Example 5 and then treated with pyrrolidine instead of N-methylbenzylamine to provide the title compound.

Example 79

Formula I: R=ethyl: n=1: $R^2=R^{2a}=R^3=R^5=H$;
$R^4$=OH; $R^{1a}$=OCH$_3$;
$R^1$=—OCH$_2$C(O)R$^{12}$(R-Configuration);
$R^{12}$=NR$^{14}$R$^{15}$; where R$^{14}$ and R$^{15}$ taken
together=—CH$_2$CH$_2$CH$_2$CH$_2$CH$_2$—, thus forming a
six membered ring incorporating the nitrogen to
which they are attached.

The title compound was isolated as a by-product of the reaction described in Example 6. The product was purified by HPLC (30×300 mm silica column) eluting with 5:4 acetonitrile/dichloromethane. Fractions containing pure product were combined and solvent removed in vacuo to give the title compound as a white foam (215.5 mg, 23% yield). MS (FAB)m/z: (M+K)=955.

Example 80

Formula I: R=ethyl: n=1: $R^2=R^{2a}=R^3=R^5=H$;
$R^4$=OH; $R^{1a}$=OCH$_3$;
$R^1$=—OCH$_2$C(O)OCH$_2$-(9-fluorenyl)
(R-Configuration).

Ascomycin (10 g, .012 mol) was dissolved in distilled CH$_2$Cl$_2$ (50 ml). Rhodium (II) acetate dimer (100 mg) was added and the mixture cooled to 0° C. 9-Fluorenylmethyl diazoacetate (3.35 g, 0.012 mol) was dissolved in CH$_2$Cl$_2$ (10 mL) and the solution added to the reaction via syringe pump at a rate of approximately 0.5 mL/hour. Addition was complete in approximately 24 hours. The reaction was stirred at 0° C. for an additional 24 hours then loaded onto silica (230–400 mesh, 400 g) and the solvent evaporated by airflow in the hood. The adsorbed silica was layered over fresh silica (800 g) in a 1 L fritted glass funnel. The silica plug was eluted with the following solvents: CH$_2$Cl$_2$ (2 L), 3:1 CH$_2$Cl$_2$/CH$_3$CN (4 L), 2:1 CH$_2$Cl$_2$/CH$_3$CN (3 L), and 1:1 CH$_2$Cl$_2$/CH$_3$CN (3 L). Fractions containing product were combined and concentrated in vacuo to give 7.32 g yellow foam. Fractions containing ascomycin were combined and concentrated in vacuo to give 3.30 g green foam (contains some catalyst). The product was further purified by HPLC (silica gel, 230–400 mesh, 50×500 mm column) eluting with 3.5:1 hexane/acetone at a flow rate of 80 ml/min. Fractions containing purest material were combined and concentrated in vacuo to give the title compound as a white foam (4.0 g, 45% yield based on recovered ascomycin).

IR (KBr) 3440, 1740, 1710 (sh), 1650 cm$^{-1}$; MS (FAB) m/z 1066 (M+K). Anal. calcd. for C$_{59}$H$_{81}$NO$_{14}$.0.7 H$_2$O: C, 68.08; H, 7.98; N, 1.35. Found: C, 68.11; H, 7.88; N, 1.51.

Example 81

Formula I: R=ethyl: n=1: $R^2=R^{2a}=R^3=R^5=H$;
$R^4$=OH; $R^{1a}$=OCH$_3$; $R^1$=—OCH$_2$C(O)OH
(R-Configuration).

The resultant product of Example 80 (5.10 g, 5 mmol) was dissolved in CH$_2$Cl$_2$ (45 mL), whereupon pipeddine (5 ml) was added. The solution was stirred at room temperature for 2 hours then transferred to a separatory funnel, diluted with additional CH$_2$Cl$_2$ (100 mL), then washed with 1N HCl (2×100 mL) and brine (2×100 mL). The organic layer was dried (Na$_2$SO$_4$), filtered, and the solvent removed in vacuo to give 5.08 g of a mixture of the title compound and N-(9-fluorenylmethyl)piperidine. MS (FAB) m/z 888 (M+K), 926 (M+2K-H).

Example 82

Formula I: R=ethyl: n=1: $R^2=R^{2a}=R^3=R^5=H$;
$R^4$=OH; $R^{1a}$=OCH$_3$;
$R^1$=—OCH$_2$C(O)R$^{12}$(R-Configuration):
$R^{12}$=NR$^{14}$R$^{15}$; R$^{15}$=—CH$_2$CH$_2$C$_6$H$_5$.

The product of Example 81 ( 100 mg, .118 mmol) was dissolved in dichloromethane ( 1 mL) and the solution cooled to 0° C. HOBT.H$_2$O (21.6 mg, .142 mmol) was added followed by EDAC (27.1 mg, .142 mmol) then phenethylamine (26.7 μL, .212 mmol). The reaction was warmed to room temperature and stirred overnight. Dichloromethane (10 mL) was added and the organic phase washed with 1N HCl (2×20 mL), saturated bicarbonate solution (2×20 mL), and then brine (2×20 mL). The organic layer was dried (Na$_2$SO$_4$), filtered, and solvent removed in vacuo to give 87.5 mg yellow foam. The crude product was purified by HPLC (20×300 mm silica column) eluting with 2:1 hexane/acetone. Fractions containing product were combined and solvent removed in vacuo to give the title compound (49.6 mg, 44% yield) as a white solid: 93°–105° C. (top); IR (KBr) 3435, 1740, 1700, 1650 cm$^{-1}$; MS (FAB) m/z 953 (M+H), 991 (M+K).

Anal. calcd. for $C_{53}H_{80}N_2O_{13}$: C, 66.78; H, 8.46; N, 2.94. Found: C, 67.13; H, 8.33; N, 3.04.

Example 83

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=CH_3$; $R^{15}=CH_2CH_2C_6H_5$.

Example 82 was repeated substituting N,N-methyl, 2-phenylethyl amine for 2-phenylethylamine to provide the title compound. MS (FAB) m/z: M+K=1005.

Example 84

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=$—$HN(CH_2)_5NH$-dansyl.

The title compound was synthesized in the manner described for Example 82 substituting dansyl cadaverine for 2-phenylethylamine. IR (KBr) 3420, 1740, 1700, 1645 cm$^{-1}$; MS (FAB) m/z 1205 (M+K).

Anal. calcd. for $C_{62}H_{94}N_4O_{15}S$: C, 63.78; H, 8.12; N, 4.80. Found: C, 63.43; H, 8.25; N, 4.48.

Example 85

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=HNC_6H_5$.

The title compound was synthesized in the manner described for Example 82 substituting aniline for 2-phenylethylamine. 112°–120° C. (mp); IR (KBr) 3440, 3400 (sh), 3300 (sh), 1740, 1700, 1650, 1540, 1500 cm$^{-1}$; MS (FAB) m/z 963 (M+K).

Anal. calcd. for $C_{51}H_{76}N_2O_{13}$: C, 66.21; H, 8.28; N, 3.03. Found: C, 66.11; H, 8.15; N, 3.23.

Example 86

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=HN(CH_2)_2N(CH_2CH_2)_2O$.

The title compound was synthesized in the manner described for Example 5 substituting 2-(4-morpholino)-ethylamine for N-methylbenzylanfine. MS (FAB) m/z: M+H=962.

Example 87

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=$—$HN(CH_2)_3N(CH_2CH_2)_2O$.

The title compound was synthesized in the manner described for Example 82 substituting 3-(4-morpholino)-propylamine for 2-phenylethylamine. MS (FAB) m/z: M+K=1014.

Example 88

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=$—$HN(CH_2)_2N(CH_3)_2$.

The title compound was synthesized in the manner described for Example 5 substituting 2-dimethylamino-ethylamine for N-methylbenzylamine. MS (FAB) m/z: M+H=920.

Example 89

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=$—$HN(CH_2)_3N(CH_3)_2$.

The title compound was synthesized in the manner described for Example 82 substituting 3-dimethylamino-propylamine for 2-phenylethylamine. MS (FAB) m/z: M+H=934.

Example 90

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=(S)$—$HNCH(CH_2C_6H5)CO_2CH_2Ph$.

The title compound was synthesized in the manner described for Example 82 substituting L-phenylalanine benzylester for 2-phenylethylamine. MS (FAB) m/z 1125 (M+K).

Example 91

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=(S)$—$HNCH(CH_2C_6H_5)CO_2H$.

The title compound was synthesized in the manner described in Example 3 substituting the product from Example 90 for the product from Example 2. IR (CDCl$_3$) 1740, 1700(sh), 1645 cm$^{-1}$; MS (FAB) m/z 1035 (M+K).

Example 92

Formula I: R=ethyl: n=1: $R^2=R^{2a}=R^3=R^5=H$;
$R^4=OH$; $R^{1a}=OCH_3$;
$R^1=$—$OCH_2C(O)R^{12}$(R-Configuration);
$R^{12}=(R)$—$HNCH(CH_2C_6H_5)CO_2CH_2Ph$.

The title compound is synthesized in the manner described for Example 82 substituting D-phenylalanine benzylester for 2-phenylethylamine.

Example 93

Formula I: R=ethyl; n=1; $R^2=R^{2a}=R^3=R^5$=H;
$R^4$=OH; $R^{1a}$=OCH$_3$;
$R^1$=—OCH$_2$C(O)R$^{12}$(R-Configuration);
$R^{12}$=(R)—HNCH(CH$_2$C$_6$H$_5$)CO$_2$H.

The title compound is synthesized in the manner described in Example 3 substituting the product from Example 92 for the product from Example 2.

Example 94

Formula I: R=ethyl; n=1; $R^2=R^{2a}=R^3=R^5$=H;
$R^4$=OH; $R^{1a}$=OCH$_3$;
$R^1$=—OCH$_2$C(O)R$^{12}$(R-Configuration);
$R^{12}$=—HN(CH$_2$)$_2$SH.

The product of Example 3 (1.2 g, 1.4 nunol) was dissolved in THF (4.5 mL) and the solution cooled to 0° C. before adding N-methylmorpholine (155.1 uL, 1.4 mmol) followed by isobutyl chloroformate (122.2 uL, 1.4 nunol). The resulting suspension was stirred for 20 minutes at 0° C. then 2-aminoethanethiol hydrochloride(320.8 mg, 2.8 mmol) was added. The mixture was stirred for 3 h at room temperature before addition of more N-methylmorpholine (387.8 uL, 3.5 mmol). The reaction was stirred overnight, loaded onto silica (40 mL) in a fritted funnel, then eluted with dichloromethane (100 mL), 1:1 hexane/acetone (200 mL), followed by acetone (100 mL). Fractions containing product were combined and solvent removed in vacuo to give 0.83 g yellow foam. The crude product was further purified by HPLC (30×300 mm silica column) eluting with 1.25:1 hexane/acetone to provide the title compound (320 mg, 25% yield) as a white foam. MS (FAB)m/z: (M+K)= 947.

Example 95

Formula I: R=ethyl; n=1; $R^2=R^{2a}=R^3=R^5$=H;
$R^4$=OH; $R^{1a}$=OCH$_3$;
$R^1$=—OCH$_2$C(O)R$^{12}$(R-Configuration);
$R^{12}$=—HN(CH$_2$)$_3$SH.

The title compound is synthesized in the manner described for Example 94 substituting 3-amino-propanethiol for 2-aminoethanethiol.

Example 96

Formula I: R=ethyl; n=1; $R^2=R^{2a}=R^3=R^5$=H;
$R^4$=OH; $R^{1a}$=OCH$_3$;
$R^1$=—OCH$_2$C(O)OC$_2$H$_5$(R-Configuration).

Silver (I) oxide (926 mg, 4.0 mmol) was added to ascomycin (791 mg, 1.0 mmol) dissolved in acetonitrile (0.8 mL) and ethyl iodoacetate (828 gL, 7.0 mmol). Mixture was stirred at room temperature for 3 days, removed volatiles in vacuo, and isolated product by chromatography on silica gel as described in Example 1. Spectral data were identical to those obtained for the product of Example 1.

Example 97

Formula I: R=ethyl; n=1; $R^2=R^{2a}=R^3=R^5$=H;
$R^4$=OH; $R^{1a}$=OCH$_3$;
$R^1$=—OCH$_2$C(O)R$^{12}$(R-Configuration);
$R^{12}$=NR$^{14}$R$^{15}$; $R^{14}$=H; $R^{15}$=2-naphthyl.

The product of Example 3 is activated as in Example 5 and then treated with 2-naphthylamine instead of N-methylbenzylamine to give the title compound.

Example 98

Formula I: R=ethyl; n=1; $R^2=R^{2a}=R^3$H;
$R^{1a}$=OCH$_3$; $R^1$=—OCH$_2$C(O)OCH$_2$Ph
(R-Configuration); $R^4$ and $R^5$ taken together form a bond.

The product of Example 2 (4.7 g, 5.0 mmol) was dissolved in toluene (7.5 mL) and triethylamine (5 mL). At 0° C. methanesulfonic anhydride (2.58g, 15.0 mmol) and 4-dimethylamino-pyridine (180mg, 1.5 mmol) were added all at once. The reaction mixture was then stirred at ambient temperature for 18h, concentrated to constant weight in vacuo, and then filtered remaining residue through silica gel (70–230 mesh, 40 mL) eluting with hexane ( 1: 1 ) until no more desired product eluted. The eluant was concentrated to dryness and further purified by HPLC on a 30×500mm column (230–400 mesh SiO$_2$), eluting with hexane:acetone (4: 1). Fractions containing desired product were pooled and concentrated in vacuo to provide the title compound (2.2 g). MS (FAB)m/z: (M+K)=960.

Example 99

Formula I: R=ethyl; n=1; $R^2=R^{2a}=R^3=R^5$=H;
$R^4$=OH; $R^{1a}$=OCH$_3$; $R^1$=—OCH$_2$C(O)OH
(R-Configuration).

The product of Example 98 (2.2 g, 2.4 mmol) was dissolved in EtOH (150 mL), to which was added 10% palladium on carbon (0.22 g). After shaking under hydrogen (1 atm) atmosphere for 5 hours, the catalyst was filtered from the mixture and the solution was concentrated under reduced pressure. The crude material is purified by chromatography as follows. A coarse fritted 350 mL Buchner funnel was charged with 230–400 mesh SiO$_2$ (175 mL). The silica bed was wetted with CH$_2$Cl$_2$:i-PrOH (10:1 with 0.5% AcOH), and tamped to constant volume, whereupon a circle of filter paper was placed over the bed. A solution of the crude product in CH$_2$Cl$_2$:i-PrOH (10:1 with 0.5% AcOH) was then carefully loaded to the top of the column. The pad was eluted with 1L of the same collecting 50 mL fractions throughout. The title product eluted in fractions 4 and 5, which concentrated down to 924 mg. MS (FAB) m/z: M+K=872.

Example 100

Formula I: R=ethyl; n=1; $R^2=R^{2a}=R^3=R^4=R^5$=H;
$R^{1a}$=OCH$_3$; $R^1$=—OCH$_2$C(O)R$^{12}$(R-Configuration);
$R^{12}$=NR$^{14}$R$^{15}$, where $R^{14}$ and $R^{15}$ are taken together as the diradical: —CH$_2$CH$_2$OCH$_2$CH$_2$—.

The product of example 99 is activated as in example 5 and treated with morpholine instead of N-methylbenzylamine to give the title compound.

Example 101

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=H$; $R^{15}=$4-$(H_2NSO_2)$-phenyl—.

The product of Example 3 is activated as in Example 5 and then treated with sulfanilamide instead of N-methylbenzylamine to give the title compound.

Example 102

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}$ and $R^{15}$ are taken together as the following diradical:
—$CH_2CH_2N(CH_2CH_2OH)CH_2CH_2$—.

The product of Example 3 is activated as in Example 5 and then treated with N-(2-hydroxyethyl)-piperazine instead of N-methylbenzylamine to give the title compound.

Example 103

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=CH_3$; $R^{15}=$phenyl.

The product of Example 3 was activated as in Example 5 and then treated with N-methylaniline instead of N-methylbenzylamine to give the title compound. MS (FAB) m/z: M+K=977.

Example 104

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=R^{15}$ —$CH_2CH_2OH$.

The product of Example 3 was activated as in Example 5 and then treated with N,N-bis-(2-hydroxyethyl)-amine instead of N-methylbenzylamine to give the title compound. MS (FAB) m/z: M+K=975.

Example 105

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=CH_3$ $R^{15}=$—$CH_2CH_2CH_2N(CH_3)_2$.

The product of Example 3 was activated as in Example 5 and then treated with N,N'-methyl-(3-dimethylaminopropyl)-amine instead of N-methylbenzylamine to give the title compound. MS (FAB) m/z: M+H=948.

Example 106

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=$phenyl $R^{15}=$—$CH_2CH_2CH_2OH$.

The product of Example 3 was activated as in Example 5 and then treated with N,N-phenyl-(3-hydroxypropyl)-amine instead of N-methylbenzylamine to give the title compound. MS (FAB) m/z: M+K=1021.

Example 107

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=H$; $R^{15}=$—$CH(CH_2OH)_2$.

The product of Example 3 was activated as in Example 5 and then treated with serinol instead of N-methylbenzylamine to give the title compound. MS (FAB) m/z: M+K=961.

Example 108

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=H$; $R^{15}=$—3-$(CF_3)$-phenyl.

The product of Example 3 was activated as in Example 5 and then treated with 3-trifluoromethylaniline instead of N-methylbenzylamine to give the title compound. MS (FAB) m/z: M+K=1031.

Example 109

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}=R^{15}$ —$CH_2CN$.

The product of Example 3 was activated as in Example 5 and then treated with iminodiacetonitrile instead of N-methylbenzylamine to give the title compound, MS (FAB) m/z: M+K=965.

Example 110

Formula I: R=ethyl: n=1; $R^2=R^{2a}=R^3=R^5=H$;
$R^4=OH$; $R^{1a}=OCH_3$;
$R^1=$—$OCH_2C(O)R^{12}$(R-Configuration);
$R^{12}=NR^{14}R^{15}$; $R^{14}$ and $R^{15}$ are taken together as the following diradical: —$CH_2CH_2$—.

The product of Example 3 was activated as in Example 5 and then treated with aziridine instead of N-methylbenzylamine to give the title compound. MS (FAB) m/z: M+K=913.

Example 111

Formula I: R=ethyl: n=1; $R^2=R^{2a}=R^3=R^5=H$;
$R^4=OH$; $R^{1a}=OCH_3$;
$R^1=$—$OCH_2NH(CO)NR^{14}R^{15}$(R-Configuration);
$R^{14}$ and $R^{15}$ are taken together as the following diradical: —$CH_2CH_2OCH_2CH_2$—.

The product of Example 3 (0.5g, 0.58 mmmol) in THF(6 mL) was stirred together with N-methylpiperidine (146 uL, 1.2 mmol) and diphenylphosphorylazide (258 uL, 1.2 mmol) at ambient temperature for 5 minutes, then at reflux for 3h. The stirring solution was cooled to ambient temperature and treated with morpholine (157 uL, 1.8 mmol) for 60h. The mixture was purified by HPLC on a column 20×300 mm (YMC 15 u, 60 Å spherical $SiO_2$) eluting with a step gradient of hexane:acetone (1:1) then hexane:acetone (2:3), to provide 440 mg (0.47 mmol) of pure title compound. MS (FAB)m/z: (M+K)=972.

Example 112

Formula I: R=ethyl: n=1: $R^2=R^{2a}=R^3=R^5=H$; $R^4=OH$; $R^{1a}=OCH_3$; $R^1=$—$OCH_2NH(CO)NR^{14}R^{15}$ (R-Configuration); $R^{14}=H$; $R^{15}$-phenyl.

The product of Example 3 was activated as in Example 111 and then treated with aniline instead of morpholine to give the title compound. MS (FAB) m/z: M+K=978.

Example 113

Formula I: R=ethyl: n=1: $R^2=R^{2a}=R^3=R^5=H$; $R^4=OH$; $R^{1a}=OCH_3$; $R^1=$—$OCH_2NHC(O)R^{14}$(R-Configuration); $R^{14}$-phenyl.

The product of Example 3 is activated as in Example 111 and then treated with benzoic acid instead of morpholine, whereupon the mixture is heated. Purification by chromatography on silica gel provides the title compound.

Example 114

Formula I: R=ethyl: n=1: $R^2=R^{2a}=R^3=R^5=H$; $R^4=OH$; $R^{1a}=OCH_3$; $R^1=$—$OCH_2C(O)OCH_2C_6H_5$(R-Configuration).

Foamed ascomycin (50g, 63 mmol, crystalline material completely dissolved in methylene chloride then concentrated to a dry foam) and benzyl iodoacetate (104g, 378 mmol, 6 eq) were mixed together, then dissolved in acetonitrile (24 mL) by stirring with an overhead mixer until homogeneous. The solution was cooled to 0° C. whereupon $Ag_2O$ (58.4g, 252 mmol, 4 eq) was added portionwise over 15 minutes (ca. 15 additions). After complete addition and mixing (5 minutes after last addition), the ice bath was removed and the reaction allowed to stir at ambient temperature for 7 days. Diethyl ether (125 mL) was added to the reaction mixture and this was then poured over silica gel (70–230 mesh, 400 mL), mixed and allowed to air dry over night. A 3L coarse fritted Buchner funnel was charged with silica gel (70–230 mesh, 2L) and the adsorbed silica carefully layered over the fresh bed, followed by a filter paper disk. The column was eluted with $CH_2Cl_2$ (4L), $CH_2Cl_2$:$CH_3CN$ (9:1, 10L), $CH_2Cl_2$:$CH_3CN$ (3:1, 8L), $CH_2Cl_2$:$CH_3CN$ (1:1, 2L), and acetone (4L), collecting 1L fractions throughout. Desired product eluted in fractions 14–20 to provide a compound that was identical to the title product of Example 2 (25.6g, 27.3 mmol) as a pale yellow foam.

Example 115

Formula I: R=ethyl: n=1: $R^2=R^{2a}=R^3=R^5=H$; $R^4=OH$; $R^{1a}=OCH_3$; $R^1=$—$OCH_2NH(CO)NR^{14}R^{15}$ (R-Configuration); $R^{14}=H$; $R^{15}=$—$CH_2CH_2CH_2OH$.

The product of Example 3 was activated as in Example 111 and then treated with 3-aminopropanol instead of morpholine to give the title compound. MS (FAB) m/z: M+K=960.

Example 116

Formula I: R=ethyl: n=1: $R^2=R^{2a}=R^3=R^5=H$; $R^4=OH$; $R^{1a}=OCH_3$; $R^1=$—$OCH_2C(O)R^{12}$(R-Configuration); $R^{12}=NR^{14}R^{15}$; $R^{14}=H$; $R^{15}=6$-carbomethoxymethylmercaptopurine hydrazid-yl.

The product of Example 3 was activated as in Example 5 and then treated with 6-carbomethoxymethylmercaptopurine hydrazide instead of N-methylbenzylamine to give the title compound.

Example 117

Formula I: R=ethyl: n=1: $R^2=R^{2a}=R^3=R^5=H$; $R^4=OH$; $R^{1a}=OCH_3$; $R^1=$—$OCH_2C(O)R^{12}$(R-Configuration); $R^{12}=NR^{14}R^{15}$; $R^{14}$ and $R^{15}$ are taken together as the following diradical: —$CH_2CH_2SO_2CH_2CH_2$—.

The product of Example 3 was activated as in Example 5 and then treated with thiomorpholine sulfone instead of N-methylbenzylamine to give the title compound. MS (FAB) m/z: M+K=1005.

Example 118

Formula I: R=ethyl: n=1: $R^2=R^{2a}=R^3=R^5=H$; $R^4=OH$; $R^{1a}=OCH_3$; $R^1=$—$OCH_2C(O)R^{12}$(R-Configuration); $R^{12}=NR^{14}R^{15}$; $R^{14}=H$; $R^{15}=$-$CH_2CH_2$-(4-F-phenyl)

The product of Example 3 was activated as in Example 5 and then treated with 4-fluorophenethylamine instead of N-methylbenzylamine to give the title compound. MS (FAB) m/z: M+K=1009.

Example 119

Formula I: R=ethyl: n=1: $R^2=R^{2a}=R^3=R^5=H$; $R^4=OH$; $R^{1a}=OCH_3$; $R^1=$—$OCH_2C(O)R^{12}$(R-Configuration); $R^{12}=NR^{14}R^{15}$; $R^{14}=H$; $R^{15}=$4-Cl-phenyl.

The product of Example 3 was activated as in Example 5 and then treated with 4-chloroaniline instead of N-methylbenzylamine to give the title compound. MS (FAB) m/z: M+K=997.

Example 120

Formula I: R=ethyl: n=1: $R^2=R^{2a}=R^3=R^5=H$; $R^4=OH$; $R^{1a}=OCH_3$; $R^1=$—$OCH_2C(O)R^{12}$(R-Configuration); $R^{12}=NR^{14}R^{15}$; $R^{14}=H$; $R^{15}=$4-($OCH_3$)-phenyl The product of Example 3 was activated as in Example 5 and then treated with 4-methoxyaniline instead of N-methylbenzylamine to give the title compound. MS (FAB) m/z: M+K=993.

Example 121

Formula I: R=ethyl: n=1: $R^2=R^{2a}=R^3=R^5=H$;
$R^4=OH$; $R^{1a}=OCH_3$;
$R^1=\text{—}OCH_2C(O)R^{12}$(R-Configuration);
$R^{12}=NR^{14}R^{15}$; $R^{14}=H$; $R^{15}=4\text{-}CH_3\text{-phenyl}$.

A solution of p-toluidine (1.03 g, 9.6 mmol) in dry THF (1 mL) was added dropwise to a stirred solution of ethylmagnesium bromide (9.6 mmol) in dry THF (9.6 mL) at 0° C. The mixture was stirred for 15 minutes then cooled to −78° C. before the addition of a solution of the product of Example 114 (750 mg, 0.8 mmol) in dry THF (2 mL). The mixture was stirred for 1 hour then added dropwise to a stirring biphasic mixture of 1N HCl (75 mL) and EtOAc (75 mL). The mixture was transferred to a separatory funnel, the organic layer washed with 1N HCl (75 mL), saturated NaHCO₃ solution (2×75 mL) and brine (2×75 mL), dried (Na₂SO₄), filtered, and concentrated in vacuo to give 0.93 g yellow oil. The crude material was purified by chromatography to give 385 mg of the title compound as a white foam. MS (FAB) m/z: M+K=977.

Example 122

Formula I: R=ethyl: n=1: $R^2=R^{2a}=R^3=R^5=H$;
$R^4=OH$; $R^{1a}=OCH_3$;
$R^1=\text{—}OCH_2C(O)R^{12}$(R-Configuration);
$R^{12}=NR^{14}R^{15}$; $R^{14}=H$; $R^{15}=3,4\text{-}Cl_2\text{-phenyl}$.

The product of Example 114 was treated as in Example 121 using 3,4-dichloroaniline instead of p-toluidine to give the title compound. MS (FAB) m/z: M+K=1031.

Example 123

Formula I: R=ethyl: n=1: $R^2=R^{2a}=R^3=R^5=H$;
$R^4=OH$; $R^{1a}=OCH_3$;
$R^1=\text{—}OCH_2C(O)R^{12}$(R-Configuration);
$R^{12}=NR^{14}R^{15}$; $R^{14}=H$; $R^{15}=3\text{-I-phenyl}$.

The product of Example 114 was treated as in Example 121 using 3-iodoaniline instead of p-toluidine to give the title compound. MS (FAB) m/z: M+K=1088.

Example 124

Formula I: R=ethyl: n=1: $R^2=R^{2a}=R^3=R^5=H$;
$R^4=OH$; $R^{1a}=OCH_3$;
$R^1=\text{—}OCH_2C(O)R^{12}$(R-Configuration);
$R^{12}=O\text{—}CH_2\text{—}[(1R)\text{-}(+)\text{-alpha-pinen-10-yl})]$.

(a) A three-neck 2L roundbottom flask equipped with an overhead stirrer was charged with diethylether (800 mL), chloroacetyl chloride (40 mL, 0.5 mol) and (1R)-(−)-nopol (85.3 mL, 0.5 mol). At 0° C., triethylamine (69.5 mL, 0.5 mol) was added dropwise over 15 minutes. After stirring at 0° C. for 1 hour, the mixture was warmed to ambient temperature and stirred for 18h. The mixture was vacuum filtered through a Buchner funnel and the white cake was extracted with ether (2×200 mL). The flitrates were then washed sequentially with 0.5N HCl (500 mL), water (500 mL) and brine (500 mL). After drying the organics (Na₂SO₄), the mixture was filtered and concentrated to a light tan oil (104 g). The resultant nopol chloroacetate was sufficiently pure to process in the next step.

(b) Sodium Iodide (20.1 g, 134 mmol) was refluxed in acetone (55 mL) for 5 minutes and cooled to room temperature. Nopol chloroacetate from step (a) (5.85 g, 24.17 mmol) was added and the reaction was stirred for 30 minutes. The solvent was removed in vacuo and the resulting slurry was partitioned between water (30 mL) and ethyl acetate (20 mL). The aqueous portion was extracted with additional ethyl acetate (20 mL) and the combined organics were washed sequentially with saturated sodium bicarbonate (30 mL) and 10% sodium bisulfite (30 mL); dried (sodium sulfate) and concentrated in vacuo to an amber oil (7 g). The resulting nopol iodoacetate was sufficiently pure to use in the next step.

(c) Ascomycin (2.5 g, 3.16 mmol) was foamed in a round bottom flask (See Example 114). To it was added the nopol iodoacetate from step (b) (5.70 g, 17.1 mmol, 5.4 eq) followed by acetonitrile (1.5 mL). After a homogeneous solution was obtained, it was cooled to 0° C. and silver(I) oxide (3.13 g, 13.4 mmol) was added portionwise (15 min). The solution was brought to room temperature by gradual melting of the ice and was stirred for 8 days. The reaction was diluted in diethyl ether and poured onto silica gel (70–230 mesh, 20 mL) and allowed to air dry. The adsorbed silica was layered on fresh silica (70–230 mesh, 100 mL) and eluted with methylene chloride (150 mL); methylene chloride:acetonitrile (9:1, 450 mL); (3:1,300 mL); (1:1,200 mL); acetone (200 mL). 50 mL fractions were collected. Fractions 11–17 contained desired crude product which was further purified by HPLC on silica eluting with 3:1 hexane:acetone (3:1). Isolated pure title compound (0.4 g). MS (FAB) m/z: M+K=1036.

Example 125

Formula I: R=ethyl: n=1: $R^2=R^{2a}=R^3=R^5=H$;
$R^4=OSi(CH_3)_3$;
$R^{12}=O\text{—}CH_2\text{—}[(1R)\text{-}(+)\text{-a-pinen-10-yl})]$.

The product of example 124 (0.200 g, 0.201 mmol) was dissolved in dry DMF (2 mL). Imidazole (0.054 g, 0.80 mmol) was added. TMS-Cl (0.051 mL, 0.401 mmol) was added and the reaction was stirred at room temperature overnight. The reaction mixture was partitioned between water (10 mL) and ethyl acetate (20 mL). The organics were washed with water (10 mL), brine (20 mL) dried (sodium sulfate) and concentrated to a faint yellow film (0.225 g). MS (FAB) m/z: M+K=1108.

Example 126

Formula I: R=ethyl: n=1: $R^2=R^{2a}=R^3=H$; $R^4$ and $R^5$ taken together form a bond; $R^{1a}=OCH_3$;
$R^1=\text{—}OCH_2C(O)R^{12}$ (R-Configuration);
$R^{12}=4\text{-(morpholinyl)}$.

Morpholine (0.104 mL, 1 g/mL, 1.19 mmol) was dissolved in acetonitrile (1.5 mL, dried over sieves). Trimethyl aluminum (0.60 mL of a 6 M solution in hexanes, 1.2 mmol) was added and the solution was stirred at room temperature for 5 minutes, then cooled to 0° C. A solution of the product from Example 125 (0.225 g, 0.210 mmol) in acetonitrile (1 mL, dried over sieves) was added dropwise and the reaction was stirred for 3 hours. The reaction mixture was diluted in ethyl acetate (15 mL) and HCl (0.25 N, 15 mL). A thick white gel formed at the interface. The organics were washed with water (15 mL) and the aqueous portion was extracted with additional ethyl acetate (15 mL). The combined organics were washed with brine (15 mL), dried (Na₂SO₄), and concentrated to a yellow oil which was purified by HPLC on silica gel and eluted with hexane:acetone (1.5:1 ). Yielded title compound: 34 mg, 17%; MS (FAB) m/z: M+K=939.

Yield product of example 29: 42 mg, 22%.

Example 127

Formula I: R=ethyl; n=1; $R^2=R^3=R^5=H$;
$R^{2a}=R^4=OH$; $R^{1a}=OCH_3$; $R^1=OCH_2C(O)R^{12}$
(R-Configuration); $R^{12}$—NH-(3-fluoro-phenyl).

The product of example 72 (1.0 g, 1.06 mmol) in THF (10 mL) and water (1 mL) was treated with selenium dioxide (0.18 g, 1.59 mmol) and t-butylhydroperoxide (1.4 mL of a 3M solution in 2,2,4-trimethylpentane, 4.24 mmol). The mixture was stirred at ambient temperature for 4 days, whereupon additional t-butylhydroperoxide solution (1.4 mL, 4.24 mmol) was added. After 2 days the reaction mixture was heated to 40° C. for 24h, then 70° C. for 48h. The solution was concentrated in vacuo and purified by HPLC on silica gel eluting with hexane:acetone (2:1). Yielded title compound: 0.18 g, 18%. MS (ESI) m/z: M+Na=963.

Example 128

Formula I: R=ethyl; n=1; $R^2=R^{2a}=R^3=R^5=H$;
$R^4=OH$; $R^{1a}=OCH_3$; $R^1=OCH_2C(O)R^{12}$
(R-Configuration); $R^{12}=O$—$CH_2$-[4-nitrophenyl].

(a) A three-neck 2L roundbottom flask equipped with an overhead stirrer was charged with diethylether (800 mL), chloroacetyl chloride (40 mL, 0.5 mol) and 4-nitrobenzylalcohol (76.5 g, 0.5 mol). At 0° C., triethylamine (69.5 mL, 0.5 mol) was added dropwise over 15 minutes. After stirring at 0° C. for 1 hour, the mixture was warmed to ambient temperature and stirred for 18h. The mixture was vacuum filtered through a Buchner funnel and the white cake was extracted with ether (2×200 mL). The flitrates were then washed sequentially with 0.5N HCl (500 mL), water (500 mL) and brine (500 mL). After drying the organics ($Na_2SO_4$), the mixture was filtered and concentrated to a light tan solid (74.8 g). The crude product was recrystallized from diethylether (71°–72° C.)

(b) Sodium Iodide (39.5 g, 260 mmol) was refluxed in acetone (104 mL) for 3 minutes and cooled to room temperature. 4-Nitrobenzyl chloroacetate from step (a) (10.7 g, 47 mmol) was added and the reaction was stirred for 30 minutes. The solvent was removed in vacuo and the resulting slurry was partitioned between water (50 mL) and ethyl acetate (50 mL). The aqueous portion was extracted with additional ethyl acetate (50 mL) and the combined organics were washed sequentially with saturated sodium bisulfite (2×50 mL) and brine (50 mL). The organics were dried (sodium sulfate) and concentrated in vacuo to pure product (15.6 g).

(c) Ascomycin (5 g, 6.3 mmol) was foamed in a round bottom flask (See Example 114). To it was added the 4-nitrobenzyl iodoacetate from step (b) (15.6 g, 48.6 mmol, 7.7 eq) followed by acetonitrile (2.5 mL). After a homogeneous solution was obtained, it was cooled to 0° C. and silver(I) oxide (5.9 g, 25.6 mmol) was added portionwise (15 min). The solution was brought to room temperature by gradual melting of the ice and was stirred for 5 days. The reaction was diluted in diethyl ether (25 mL), poured onto silica gel (70–230 mesh, 40 mL) and allowed to air dry. The adsorbed silica was layered on fresh silica (70–230 mesh, 200 mL) and eluted with methylene chloride (500 mL); methylene chloride:acetonitrile (9:1, 400 mL); (6:1, 300 mL); (3:1, 1000 mL); (1:1, 500 mL); (1:2, 300 mL). 100 mL fractions were collected. Fractions containing desired product ($CH_2Cl_2:CH_3CN$ 3:1) were pooled and concentrated in vacuo to provide the title compound (2.86 g, 2.9 mmol). Ascomycin was recovered in the later fractions (1.59 g, 2.0 mmol). MS (ESI) m/z: M+Na=1007.

Example 129

Formula I: R=ethyl; n=1; $R^2=R^{2a}=R^3=R^5=H$;
$R^4=OH$; $R^{1a}=OCH_3$; $R^1=$—$OCH_2C(O)R^{12}$
(R-Configuration); $R^{12}=$—$NR^{14}R^{15}$;
$R^{14}=$—$(CH_2(_2N(CH_2CH_2)_2O$; $R^{14}=$—$CH_2CH_2OH$.

The title compound was synthesized in the manner described for Example 5 substituting N,N-[2-hydroxyethyl] [2-(4-morpholino)-ethyl]amine for N-methylbenzylamine. MS (FAB) m/z: M+H=962.

Example 130

Formula I: R=ethyl; n=1; $R^2=R^{2a}=R^3=R^5=H$;
$R^4=OH$; $R^{1a}=OCH_3$; $R^1=$—$OCH_2C(O)R^{12}$
(R-Configuration); $R^{12}=$—$OCH_2CCl_3$.

Example 128 was repeated substituting 2,2,2-trichloroethanol for p-nitrobenzylalcohol.

Example 131

In Vivo Assay of Biological Activity

The immunosuppressant activity of the compounds of the present invention was determined using the human mixed lymphocyte reaction (MLR) assay described by Kino, T. et al. in Transplantation Proceedings, XIX(5):36–39, Suppl. 6 (1987). The results of the assay, shown below in Table 1, demonstrate that the compounds tested are effective immunomodulators at sub-micromolar and, in some instances, sub-nanomolar concentrations.

TABLE 1

| Ex. # | $IC_{50}(M)$ |
|---|---|
| 1 | $0.9 \times 10^{-9}$ |
| 2 | $7.6 \times 10^{-9}$ |
| 3 | $140.0 \times 10^{-9}$ |
| 4 | $0.5 \times 10^{-9}$ |
| 6 | $0.1 \times 10^{-9}$ |
| 29 | $0.7 \times 10^{-9}$ |
| 31 | $1.1 \times 10^{-9}$ |
| 39 | $172.6 \times 10^{-9}$ |
| 51 | $0.3 \times 10^{-9}$ |
| 53 | $0.2 \times 10^{-9}$ |
| 54 | $0.02 \times 10^{-9}$ |
| 56 | $0.01 \times 10^{-9}$ |
| 57 | $0.10 \times 10^{-9}$ |
| 58 | $0.15 \times 10^{-9}$ |
| 59 | $0.05 \times 10^{-9}$ |
| 71 | $0.1 \times 10^{-9}$ |
| 72 | $0.08 \times 10^{-9}$ |
| 73 | $0.04 \times 10^{-9}$ |
| 74 | $0.06 \times 10^{-9}$ |
| 82 | $0.3 \times 10^{-9}$ |
| 83 | $0.4 \times 10^{-9}$ |
| 85 | $0.5 \times 10^{-9}$ |
| 87 | $1.1 \times 10^{-9}$ |
| 88 | $0.1 \times 10^{-9}$ |
| 89 | $0.5 \times 10^{-9}$ |
| 99 | $0.9 \times 10^{-9}$ |
| 111 | $1.8 \times 10^{-9}$ |
| 112 | $0.1 \times 10^{-9}$ |

It is understood that the foregoing detailed description and accompanying examples are merely illustrative and are not to be taken as limitations upon the scope of the invention, which is defined solely by the appended claims and equivalents thereof. Variations and modifications of the disclosed embodiments will be apparent to those skilled in the art. Such variations and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula:

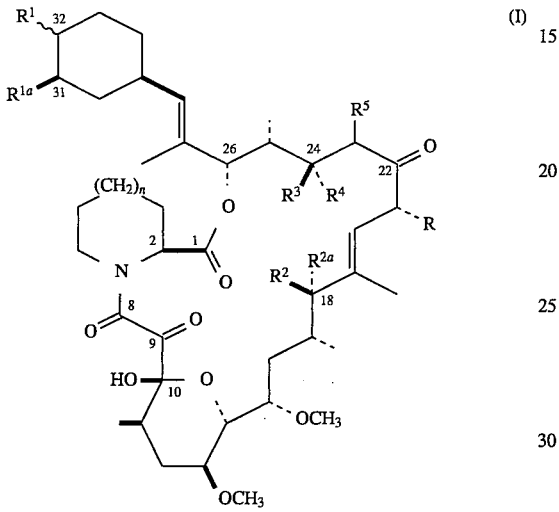

(I)

or a pharmaceutically acceptable salt, ester or amide thereof, wherein the ester is selected from $C_1$-to-$C_6$ -alkyl esters, $C_5$-to-$C_7$ cycloalkyl esters, aryl-$C_1$-to-$C_6$-alkyl esters and esters resulting from reaction of an alcohol moiety in the compound of formula I with a $C_1$ -to-$C_6$-alkyl carboxylic acid, a $C_1$-to-$C_6$-alkyl dicarboxylic acid or an arylcarboxylic acid and wherein the amide results from reaction of a carboxylic acid moiety in the compound of formula I with $NH_3$, $NH_2(C_1$-to-$C_3$-alkyl), $NH(C_1$-to-$C_2$ alkyl)$_2$ or a 5 - or 6- membered ring heterocycle containing one nitrogen atom, wherein n is zero or one;

R is selected from the group consisting of hydrogen, methyl, ethyl, allyl, propyl, 2-hydroxyethyl, cyclopropylmethyl, 2-oxopropyl and 2-ethanal;

$R^1$ and $R^{1a}$ are selected such that one of $R^1$ and $R^{1a}$ is hydrogen, —($C_1$–$C_6$-alkyl)oxy or hydroxy, and the other is chosen from the group consisting of:

(I) —O(CH$_2$)jC(O)R$^{12}$, where j is one-to-five, and $R^{12}$ is selected from the group consisting of:

(A) hydroxy;

(B) —OR$^{13}$, wherein $R^{13}$ is:
  (i) —($C_1$–$C_{10}$-alkyl);
  (ii) —(cyclo-$C_3$–$C_8$-alkyl);
  (iii) —(cyclo-$C_3$–$C_8$-alkyl-$C_1$–$C_3$-alkyl);
  (iv) aryl-($C_1$–$C_6$-alkyl)—, where the zero, one, two or three substituents on the aryl group, each designated $R^{301}$, are independently selected from the group consisting of:
    (a) —($C_1$-to-$C_7$-alkyl);
    (b) —($C_2$-to-$C_6$-alkenyl);
    (c) halogen;
    (d) —(CH$_2$)$_m$NR$^8$R$^9$, where m is zero-to-six, and NR$^8$R$^9$ is either a nitrogen atom attached to R$^8$ and R$^9$, wherein $R^8$ and $R^9$ are independently selected from the group consisting of:

(1) hydrogen;
(2) —R$^{400}$, wherein $R^{400}$ is selected from the group consisting of:
a. mod-aryl, wherein mod-aryl is an unsubstituted aryl group or a substituted aryl group substituted with one, two or three substituents $R^{302}$ wherein at each occurrence $R^{302}$ is independently selected from the group consisting of:
  1. —($C_1$-to-$C_7$-alkyl);
  2. —($C_2$-to-$C_6$-alkenyl);
  3. halogen;
  4. —(CH$_2$)$_m$NR$^{18}$R$^{19}$, where m is as defined above and NR$^{18}$R$^{19}$ is either a nitrogen atom attached to R$^{18}$ and R$^{19}$, wherein $R^{18}$ and $R^{19}$ are independently selected from the group consisting of hydrogen, —($C_1$–$C_6$-alkyl), unsubstituted aryl-, and unsubstituted aryl-($C_1$–$C_6$-alkyl); or NR$^{18}$R$^{19}$ may be a 5-to-7 -membered heterocyclic ring;
  5. —CN;
  6. —CHO;
  7. mono-, di-, tri-, or perhalogenated —$C_1$–$C_6$-alkyl;
  8. —S(O)$_s$R$^{18}$, where s and $R^{18}$ are as defined above;
  9. —C(O)NR$^{18}$R$^{19}$, where NR$^{18}$R$^{19}$ is as defined above;
  10. —(CH$_2$)$_m$OR$^{18}$, where m and $R^{18}$ are as defined above;
  11. —CH(OR$^{16}$)(OR$^{17}$), where $R^{16}$ and $R^{17}$ are independently selected from —($C_1$-to-$C_3$ alkyl) groups or, taken together, $R^{16}$ and $R^{17}$ form an ethylene or propylene bridge;
  12. —(CH$_2$)$_m$OC(O)R$^{18}$, where m and $R^{18}$ are as defined above;
  13. —(CH$_2$)$_m$C(O)OR$^{18}$, where m and $R^{18}$ are as defined above;
  14. OR$^{10}$, where $R^{10}$ is:
    (i) —PO(OH)OH,
    (ii) —SO$_3$H,
    (iii) —C(O)(CH$_2$)$_m$C(O)OH, wherein m is as defined above;
  15. —NO$_2$;
  16. —N$_3$;
  17. —($C_2$-to-$C_6$-alkynyl);
  18. —C≡C—Si(CH$_3$)$_3$; and
  19. guanidino substituted by:
    a) hydrogen;
    b) —($C_1$–$C_6$-alkyl);
    c) unsubstituted aryl;
    d) ($C_1$–$C_8$-alkyl)—C(O)—;
    e) unsubstituted aryl—S(O)$_2$;
    f) ($C_1$–$C_6$-alkyl)—OC(O)—;
    g) unsubstituted aryl-($C_1$–$C_6$-alkyl)-OC(O);
    h) unsubstituted aryl—OC(O); or
    i) ($C_1$–$C_6$-alkyl)SO$_2$—; or
taken together, any two adjacent $R^{302}$ substituents in a di- or trisubstituted mod-aryl group form a 5-, 6- or 7-membered carbocyclic ring, or a 5-, 6-, or 7-membered heterocyclic ring;
b. —Q-mod-aryl, wherein mod-aryl is defined as above and where the divalent radical —Q— is selected from the group consisting of:
  1. —($C_1$-to-$C_6$-alkyl)—;
  2. —($C_2$-to-$C_6$-alkenyl)—;

3. —($C_2$-to-$C_6$-alkynyl)—;
4. —$(CH_2)_m$O—, wherein m is as defined above;
5. —O$(CH_2)_m$—, wherein m is as defined above;
6. —N($R^{18}$)C(O)—, wherein $R^{18}$ is as defined above;
7. —C(O)N($R^{18}$)—, wherein $R^{18}$ is as defined above;
8. —S(O)$_s$—, wherein s is as defined above;
9. —N($R^{18}$)—, wherein $R^{18}$ is as defined above;
10. —N($R^{18}$)S(O)$_t$—, wherein t is one or two, and $R^{18}$ is as defined above;
11. —S(O)$_t$N($R^{18}$)—, wherein t and $R^{18}$ are as defined above;
12. —C(O)—;
13. —NN—;
14. —CHN—;
15. —NCH—;
16. —ONCH—; and
17. —CHNO—;
c. —mod-Het, wherein mod-Het is an unsubstituted Het or a substituted Het group substituted with one, two or three substituents $R^{302}$ wherein at each occurrence $R^{302}$ is independently defined as above;
d. —Q-mod-Het wherein mod-Het is defined as above and, where Q is as defined above;
e. —biaryl;
f. —Q-biaryl, where Q is as defined above;
g. —mod-aryl-Q-mod-aryl, wherein mod-aryl is defined as above and where Q is as defined above;
h. —mod-aryl-Q-mod-Het, wherein mod-aryl and mod-Het are defined as above and where Q is as defined above;
i. —med-Het-Q-mod-aryl, wherein mod-aryl and mod-Het are defined as above and where Q is as defined above;
j. —mod-Het-Q-mod-Het, wherein med-Het is defined as above and where Q is as defined above;
k. —mod-Het-mod-aryl wherein mod-aryl and mod-Het are defined as above and;
l. —mod-aryl-mod-Het wherein mod-aryl and mod-Het are defined as above and; and
m. —mod-Het-mod-Het wherein mod-Het is defined as above and;
(3) —($C_1$-to-$C_6$-alkyl);
(4) substituted-$C_1$-to-$C_6$-alkyl;
(5) —($C_3$-to-$C_6$-alkenyl);
(6) substituted-$C_3$-to-$C_6$-alkenyl;
(7) —($C_3$-to-$C_6$-alkynyl);
(8) substituted-$C_3$-to-$C_6$-alkynyl;
(9) —(cyclo-$C_3$-to-$C_{10}$-alkyl);
(10) substituted-cyclo-$C_3$-to-$C_{10}$-alkyl;
(11) —(cyclo-$C_4$-to-$C_{10}$-alkenyl);
(12) substituted-cyclo-$C_4$-to-$C_{10}$-alkenyl;
(13) —(bicyclo-$C_6$-to-$C_{10}$-alkyl);
(14) substituted-bicyclo-$C_6$-to-$C_{10}$-alkyl;
(15) —(bicyclo-$C_6$-to-$C_{10}$-alkenyl);
(16) substituted -bicyclo-$C_6$-to-$C_{10}$-alkenyl;
(17) —(bicyclo-$C_6$-to-$C_{10}$-alkenyl)-$C_1$-to-$C_6$-alkyl; and
(18) substituted-bicyclo-$C_6$-to-$C_{10}$-alkenyl-$C_1$-to-$C_6$-alkyl; or —N$R^8R^9$ may be a 5- to 7-membered heterocyclic ring;
(e) —CN;
(f) —CHO;
(g) mono-, di-, tri-, or perhalogenated —$C_1$–$C_6$-alkyl;
(h) —S(O)$_s$$R^8$, where s and $R^8$ are as defined above;
(i) —C(O)N$R^8R^9$, where N$R^8R^9$ is as defined above;
(j) —$(CH_2)_m$O$R^8$, where m and $R^8$ are as defined above;
(k) —CH(O$R^{16}$)(O$R^{17}$), where $R^{16}$ and $R^{17}$ are as defined above;
(l) —$(CH_2)_m$OC(O)$R^8$, where m and $R^8$ are as defined above;
(m) —$(CH_2)_m$C(O)O$R^8$, where m and $R^8$ are as defined above;
(n) —O$R^{10}$, where $R^{10}$ is as defined above;
(o) —$NO_2$;
(p) —$N_3$;
(q) —$R^{400}$, as defined above;
(r) —S(O)$_t$N$R^8R^9$, where t and N$R^8R^9$ are as defined above;
(s) —N$R^8$S(O)$_t$$R^9$, where t, $R^8$ and $R^9$ are as defined above;
(t) —($C_2$-to-$C_6$-alkynyl);
(u) —C≡C—Si($CH_3$)$_3$; and
(v) guanidino substituted by:
(1) hydrogen;
(2) —($C_1$–$C_6$-alkyl);
(3) —mod-aryl wherein mod-aryl is defined as above;
(4) ($C_1$–$C_8$-alkyl)-C(O)—;
(5) mod-aryl-S(O)$_2$— wherein mod-aryl is defined as above;
(6) ($C_1$–$C_6$-alkyl)-OC(O)—;
(7) mod-aryl-($C_1$–$C_6$-alkyl)-OC(O) wherein mod-aryl is defined as above;
(8) mod-aryl-OC(O)— wherein mod-aryl is defined as above; or
(9) ($C_1$–$C_6$-alkyl)$SO_2$—; or
taken together, any two adjacent $R^{301}$ substituents in a di- or trisubstituted aryl group form a 5-, 6- or 7-membered carbocyclic ring, or a 5-, 6- or 7-membered heterocyclic ring;
with the proviso that each $R^{301}$ substituent or each ring formed by two adjacent $R^{301}$ groups may comprise no more than twenty non-hydrogen atoms;
(v) aryl—;
(vi) Het—;
(vii) heterocyclic—;
(viii) mono-, di-, tri-, or per-halogenated-$C_1$–$C_6$-alkyl-;
(ix) —(cyclo-$C_5$–$C_{10}$-alkenyl);
(x) —(cyclo-$C_5$–$C_{10}$-alkenyl-$C_1$–$C_3$-alkyl);
(xi) —(bicyclo-$C_6$–$C_{12}$-alkenyl); or
(xii) —(bicyclo-$C_6$–$C_{12}$-alkenyl-$C_1$–$C_3$-alkyl);
(C) —N$R^{14}R^{15}$ wherein $R^{14}$ and $R^{15}$ are independently selected from the group consisting of:
(i) hydrogen;
(ii) —$R^{400}$, as defined above;
(iii) —($C_1$-to-$C_{10}$-alkyl);
(iv) sub-$C_1$-to-$C_{10}$-alkyl;
(v) —(cyclo-$C_3$-to-$C_{10}$-alkyl);
(vi) sub-cyclo-$C_3$-to-$C_{10}$-alkyl;
(vii) —(cyclo-$C_3$-to-$C_{10}$-alkyl-$C_1$-to-$C_3$-alkyl);
(viii) sub-cyclo-$C_3$-to-$C_{10}$-alkyl-$C_1$-to-$C_3$-alkyl;
(ix) —($C_3$-to-$C_{10}$-alkenyl);
(x) sub-$C_3$-to-$C_{10}$-alkenyl;
(xi) —(cyclo-$C_4$-to-$C_{10}$-alkenyl);
(xii) sub-cyclo-$C_4$-to-$C_{10}$-alkenyl;
(xiii) —(cyclo-$C_6$-to-$C_{10}$-alkyl-$C_3$–$C_5$-alkenyl);
(xiv) sub-cyclo-$C_6$-to-$C_{10}$-alkyl-$C_3$–$C_5$-alkenyl;
(xv) —($C_3$-to-$C_{10}$-alkynyl);
(xvi) sub-$C_3$-to-$C_{10}$-alkynyl;
(xvii) —(cyclo-$C_6$-to-$C_{10}$-alkyl-$C_3$–$C_5$-alkynyl);

(xviii) sub-cyclo-$C_6$-to-$C_{10}$-alkyl-$C_3$–$C_5$-alkynyl;
(xix) —(bicyclo-$C_6$-to-$C_{10}$-alkyl);
(xx) sub-bicyclo-$C_6$-to-$C_{10}$-alkyl;
(xxi) —(bicyclo-$C_6$-to-$C_{10}$-alkenyl);
(xxii) sub-bicyclo-$C_6$-to-$C_{10}$-alkenyl;
(xxiii) —aryl;
(xxiv) —Het; and
(xxv) $R^6$, where $R^6$ is selected from the group consisting of:
(a) hydrogen;
(b) —($C_1$-to-$C_{10}$-alkyl);
(c) mod-$C_1$-to-$C_{10}$-alkyl;
(d) —($C_3$-to-$C_{10}$-alkenyl);
(e) mod-$C_3$-to-$C_{10}$-alkenyl;
(f) —($C_3$-to-$C_{10}$alkynyl);
(g) mod-$C_3$-to-$C_{10}$-alkynyl;
(h) —(cyclo-$C_3$-to-$C_{10}$-alkyl);
(i) mod-cyclo-$C_3$-to-$C_{10}$-alkyl;
(j) —( cyclo-$C_4$-to-$C_{10}$-alkenyl);
(k) mod-cyclo-$C_4$-to-$C_{10}$-alkenyl;
(l) —(bicyclo-$C_6$-to-$C_{10}$-alkyl);
(m) mod-bicyclo-$C_6$-to-$C_{10}$-alkyl;
(n) —(bicyclo-$C_6$-to-$C_{10}$-alkenyl);
(o) mod-bicyclo-$C_6$-to-$C_{10}$-alkenyl;
(p) —$R^8$, as defined above;
(q) —aryl; and
(r) —Het; or $NR^{14}R^{15}$ may be a 5- to 7-membered heterocyclic ring, where the ring consists of carbon atoms, the nitrogen atom shown, and zero, one or two additional heteroatoms independently selected from —O—, —S(O)$_s$—, wherein s is as defined above, and —$NR^8$—, wherein $R^8$ is as defined above, which ring is unsubstituted or substituted with from one-to-five compatible radicals independently selected from the group consisting of:
(i) $R^6$, as defined above;
(ii) —$(CH_2)_m OR^6$, where m and $R^6$ are as defined above;
(iii) —$(CH_2)_m NR^6R^7$, where m is as defined above and $NR^6R^7$ is either a nitrogen atom attached to $R^6$ and $R^7$, wherein $R^6$ is as defined above and $R^7$ is independently selected from the group defining $R^6$, or —$NR^6R^7$ may be a 5- to 7-membered heterocyclic ring, where the ring consists of carbon atoms, the nitrogen atom shown, and zero, one, or two additional heteroatoms independently selected from the group consisting of —O—, —S(O)$_s$—, wherein s is as defined above, and —$NR^8$—, wherein $R^8$ is as defined above, which ring is unsubstituted or substituted with from one-to-six compatible radicals independently selected from the group consisting of:
(a) —$R^8$, as defined above;
(b) —$(CH_2)_m OR^8$, wherein m and $R^8$ are as defined above;
(c) —$S(O)_s R^8$, wherein s and $R^8$ are as defined above;
(d) —$S(O)_t NR^8R^9$, wherein t and $NR^8R^9$ are as defined above;
(e) —$(CH_2)_m NR^8R^9$, wherein m and $NR^8R^9$ are as defined above;
(f) —$SO_3H$;
(g) =$NOR^8$, wherein $R^8$ is as defined above;
(h) —$R^{400}$, as defined above;
(i) —aryl;
(j) —Het; and
(k) —$R^{399}$, wherein $R^{399}$ is selected from the group consisting of:
(1) hydroxyl;
(2) —C(O)OH;
(3) —C(O)$OR^8$, where $R^8$ is as defined above;
(4) —(cyclo-$C_3$-to-$C_7$-alkyl);
(5) oxo;
(6) thiooxo;
(7) epoxy;
(8) halogen;
(9) —CN;
(10) —$N_3$;
(11) —$NO_2$;
(12) —$OR^{10}$, where $R^{10}$ is as defined above;
(13) —$S(O)_t NR^8R^9$, wherein t and $NR^8R^9$ are as defined above;
(14) —$NR^8 S(O)_t R^9$, where t, $R^8$ and $R^9$ are as defined above;
(15) —$CH(OR^{16})(OR^{17})$, where $R^{16}$ and $R^{17}$ are as defined above; and
(16) guanidino substituted by hydrogen; —($C_1$–$C_6$-alkyl); aryl; ($C_1$–$C_6$-alkyl)CO—; aryl-$SO_2$—; ($C_1$–$C_6$-alkyl)OC(O)—; aryl-($C_1$–$C_6$-alkyl)OC(O)—; aryl-OC(O)—; or ($C_1$–$C_6$-alkyl)-$SO_2$—;
(iv) —C(O)$OR^6$, where $R^6$ is as defined above;
(v) —$SO_3H$;
(vi) —$S(O)_s R^6$, where s and $R^6$ are as defined above;
(vii) —$S(O)_t NR^6R^7$, where t and $NR^6R^7$ are as defined above;
(viii) =$NOR^6$, where $R^6$ is as defined above;
(ix) —aryl;
(x) —Het;
(xi) —$R^{399}$, as defined above; and
(xii) —$R^{400}$, as defined above;
(D) —aryl;
(E) Het—;
(F) mono-, di-, tri-, or per-halogenated-$C_1$–$C_6$alkyl;
(G) —$N(R^8)NR^{14}R^{15}$, where $R^8$ and $NR^{14}R^{15}$ are as defined above;
(H) —$Si(R^{11})_3$, where each $R^{11}$ is independently —($C_1$–$C_6$-alkyl), aryl-($C_1$–$C_6$-alkyl)—, or aryl;
(I) —$OSi(R^{11})_3$, where each $R^{11}$ is independently as defined above;
(J) —$Sn(R^{11})_3$, where each $R^{11}$ is independently as defined above;
(K) —$P(R^{11})_2$, where each $R^{11}$ is independently as defined above;
(L) —$R^{14}$, as defined above; and
(M) halogen;
(II) —$O(CH_2)_m S(O)_s R^{12}$, where m, s and $R^{12}$ are as defined above;
(III) —$O(CH_2)jCN$, where j is as defined above;
(IV) —$O(CH_2)jC(=NOR^{14})R^{12}$, where j, $R^{12}$ and $R^{14}$ are as defined above;
(V) —$O(CH_2)jC(=N^+(O^-)R^{14})R^{12}$, where j, $R^{12}$ and $R^{14}$ are as defined above, with the proviso that $R^{14}$ may not be hydrogen;
(VI) —$O(CH_2)jC(=NOR^{14})R^{15}$, where j, $R^{14}$ and $R^{15}$ are as defined above;
(VII) —$O(CH_2)jC(=N^+(O^-)R^{14})R^{15}$, where j, $R^{14}$ and $R^{15}$ are as defined above, with the proviso that $R^{14}$ may not be hydrogen;
(VIII) —$OC(O)O(CH_2)jC(O)NR^{14}R^{15}$, where j and $NR^{14}R^{15}$ are as defined above;
(IX) —$O(CH_2)jNR^6C(O)OR^{14}$, where j, $R^6$ and $R^{14}$ are as defined above;

(X) —O(CH$_2$)jNR$^6$C(O)NR$^{14}$R$^{15}$, where j, R$^6$ and NR$^{14}$R$^{15}$ are as defined above;

(XI) —O(CH$_2$)jNR$^6$C(O)NR$^7$NR$^{14}$R$^{15}$, where j, R$^6$, R$^7$ and NR$^{14}$R$^{15}$ are as defined above;

(XII) —O(CH$_2$)jNR$^6$C(O)R$^{14}$, where j, R$^6$ and R$^{14}$ are as defined above; and (XIII) —O(CH$_2$)jNR$^6$C(O)OC(O)R$^{14}$, where j, R$^6$ and R$^{14}$ are as defined above;

R$^2$ and R$^{2a}$ are independently hydrogen, halogen, or —OR$^{14}$, wherein R$^{14}$ is as defined above, or one of R$^2$ and R$^{2a}$ may be hydroxy, when the other of R$^2$ or R$^{2a}$ is hydrogen, or R$^2$ and R$^{2a}$ taken together is oxo or thiooxo;

R$^3$ and R$^4$ are chosen, when R$^5$ is hydrogen, such that one of R$^3$ and R$^4$ is hydrogen and the other is selected from hydrogen, hydroxy, —OCOR$^8$, where R$^8$ is as defined above, or —OSi(R$^{11}$)$_3$, where each R$^{11}$ is independently as defined above, or one of R$^3$ and R$^4$ is joined with non-hydrogen R$^5$ to form a C-23/C-24 bond, with the other of R$^3$ and R$^4$ being hydrogen, hydroxy, —OCOR$^8$, where R$^8$ is as defined above, or —OSi(R$^{11}$)$_3$, where each R$^{11}$ is independently as defined above; and R$^5$ is hydrogen, or taken together with either R$^3$ or R$^4$, forms a C-23/C-24 bond;

with the proviso that when R$^{1a}$ is methoxy, R$^2$ is hydrogen and R$^{2a}$ is hydroxy or fluoro or R$^{2a}$ is hydrogen and R$^2$ is hydroxy or fluoro, R$^3$ is hydroxy, R$^4$ is hydrogen, R$^5$ is hydrogen and n is 2, then R$^1$ is other than —OCH$_2$C(O)OCH$_2$CH$_3$ and wherein at each occurrence the aryl group is independently selected from the group consisting of phenyl, 1-naphthyl, 2-naphthyl, azulenyl, fluorenyl, (1,2)-dihydronaphthyl, (1,2,3,4)-tetrahydronaphthyl, indenyl and indanyl and wherein each aryl group is unsubstituted or substituted with from one, two or three independently selected substituents, R$^{301}$, as defined above; and wherein at each occurrence, the heterocyclic group is independently selected from the group consisting of aziridinyl, thiomorpholine, thiomorpholine-oxide, thiomorpholine dioxide, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, and isothiazolidinyl wherein any carbon or heteroatom with suitable valence may bear a substituent, R$^{301}$, which at each occurrence is independently as defined above; and wherein at each occurrence, the Het group is independently selected from pyrrolyl, pyrazolyl, cytosinyl, thiocytosinyl, imidazolyl, pyridyl, pyrazinyl, pyrimidinyl, pyridazinyl, xanthenyl, xanthonyl, xanthopterinyl, oxazolyl, thiouracilyl, isoxazolyl, indolyl, quinolinyl, uracilyl, urazolyl, uricyl, thiazolyl, isothiazolyl, isoquinolinyl, thyminyl, benzimidazolyl, benzothiazolyl, benzoxazolyl, furyl, thienyl, and benzothienyl wherein any carbon or heteroatom with suitable valence may bear a substituent, R$^{301}$, which at each occurrence is independently as defined above; and wherein at each occurrence, the term mod when used as a prefix for a group selected from —C$_1$-to-C$_{10}$-alkyl, —C$_3$-to-C$_{10}$-alkenyl, —C$_3$-to-C$_{10}$-alkynyl, —cyclo-C$_3$-to-C$_{10}$-alkyl, —cyclo-C$_4$-to-C$_{10}$-alkenyl, —bicyclo-C$_6$-to-C$_{10}$-alkyl, and —bicyclo-C$_6$-to-C$_{10}$-alkenyl refers to said group substituted with from one to six radicals independently selected from the group consisting of —R$^8$, —(CH$_2$)$_m$OR$^8$, —S(O)$_t$NR$^8$R$^9$, —S(CH$_2$)$_m$NR$^8$R$^9$, —S(O)$_3$H, =NOR$^8$, —R$^{399}$, —R$^{400}$, and —Het where R$^8$, R$^9$, m, s, t, —R$^{399}$, —R$^{400}$, —aryl and —Het are independently as defined above; and wherein at each occurrence, the term sub when used as a prefix for a group selected from —C$_1$-to-C$_{10}$-alkyl, —cyclo-C$_3$-to-C$_{10}$-alkyl, —cyclo-C$_3$-to-C$_{10}$-alkyl-C$_1$-to-C$_3$-alkyl, —C$_3$-to-C$_{10}$-alkenyl, —cyclo-C$_4$-to-C$_{10}$-alkenyl, —cyclo-C$_6$-to-C$_{10}$-alkyl-C$_3$-to-C$_5$-alkenyl, —C$_3$-to-C$_{10}$-alkynyl, —cyclo-C$_6$-to-C$_{10}$-alkyl-C$_3$-to-C$_5$-alkynyl, —bicyclo-C$_6$-to-C$_{10}$-alkyl, and —bicyclo-C$_6$-to-C$_{10}$-alkenyl refers to said group substituted with from one to six radicals independently selected from the group consisting of —R$^6$, —(CH$_2$)$_m$OR$^6$, —NR$^6$R$^7$, —C(O)OR$^6$, —S(O)$_3$H, —S(O)$_s$R$^6$, —S(O)$_t$NR$^6$R$^7$, =NOR$^6$, —R$^{399}$, —R$^{400}$, —aryl and —Het where R$^6$, R$^7$, m, s, t, —R$^{399}$, —R$^{400}$, —aryl and —Het are independently as defined above; and wherein at each occurrence, the term substituted when used as a prefix for a group selected from —bicyclo-C$_6$-to-C$_{10}$-alkenyl, —bicyclo-C$_6$-to-C$_{10}$-alkyl, —C$_3$-to-C$_6$-alkenyl, —C$_1$-to-C$_6$-alkyl, —C$_3$-to-C$_6$-alkynyl, —cyclo-C$_4$-to-C$_{10}$-alkenyl, —cyclo-C$_3$-to-C$_{10}$-alkyl, and —bicyclo-C$_6$-to-C$_{10}$-alkenyl-C$_1$-to-C$_6$-alkyl, refers to said group substituted with from one to three radicals independently selected from the group consisting of halogen: —OH; (C$_1$–C$_6$-alkyl)NH—; di(C$_1$–C$_6$-alkyl)N—; —CO$_2$H; —CONH$_2$; —SH: (C$_1$–C$_6$-alkyl)S—; (C$_1$–C$_6$-alkyl)O—; (C$_1$–C$_6$-alkyl)OC(O)—; mod-aryl-(C$_1$–C$_6$-alkyl)OC(O)—; (C$_1$–C$_6$-alkyl)O-C(O)NH—; (C$_1$–C$_6$-alkyl)C(O)NH—; mod-aryl-(C$_1$–C$_6$-alkyl)OC(O)NH—; mod-aryl-OC(O)NH—; (C$_1$–C$_6$-alkyl)CO-guanidino; mod-aryl-(SO$_2$)-guanidino; (C$_1$–C$_6$-alkyl)OC(O)-guanidino; H$_2$N—; mod-aryl-(C$_1$–C$_6$-alkyl)OC(O)-guanidino; mod-aryl-OC(O)guanidino; (C$_1$–C$_6$-alkyl)NHC(O)—; di(C$_1$–C$_6$-alkyl)NC(O)—; mod-aryl-NHCO—; di(mod-aryl)NCO—; —OSO$_2$R$^{11}$; oxo; epoxy; mod-aryl-O—; mod-aryl-S—; mod-aryl-(C$_1$–C6-alkyl)O—;mod-aryl-(C$_1$–C$_6$-alkyl)-S—; mod-Het-O—; mod-Het-S—; mod-Het-(C$_1$–C$_6$-alkyl)O—; mod-Het-(C$_1$–C$_6$-alkyl)S—; mod-aryl—; mod-Het—; —SO$_3$H; —S(O)$_t$NH$_2$; —S(O)$_t$NHR$^{11}$; —S(O)$_t$NR$^{11}$R$^{11}$, where both R$^{11}$'s are independently selected; and —S(O)$_t$R$^{11}$; wherein guanidino, mod-aryl, oxo, epoxy, mod-Het—, s, t and R$^{11}$ are as independently defined above.

2. A compound according to claim 1, having the formula:

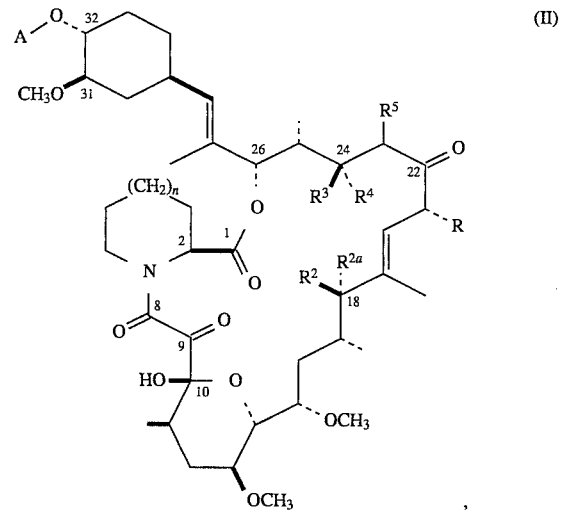

(II)

wherein n, R, R$^2$, R$^{2a}$, R$^3$, R$^4$ and R$^5$ are as defined in claim 1 and A is a radical having a formula selected from the group consisting of:

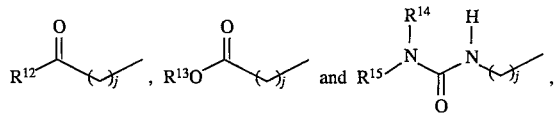

where j, $R^{12}$, $R^{13}$, $R^{14}$ and $R^{15}$ are as defined in claim 1.

3. A compound according to claim 1, having the formula:

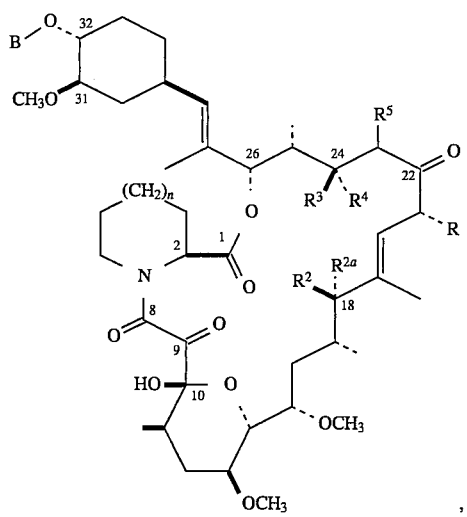

(III)

wherein n, R, $R^2$, $R^{2a}$, $R^3$, $R^4$ and $R^5$ are as defined in claim 1, and B is a radical having a formula selected from the group consisting of:

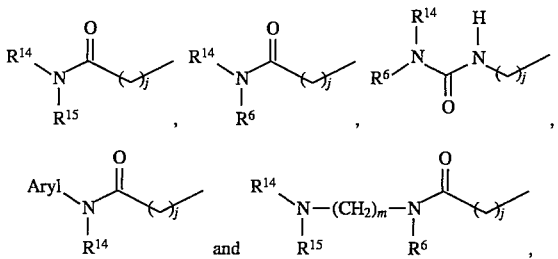

where j, m, $R^6$, $R^{14}$ and $R^{15}$ are as defined in claim 1.

4. A compound according to claim 1, having the formula:

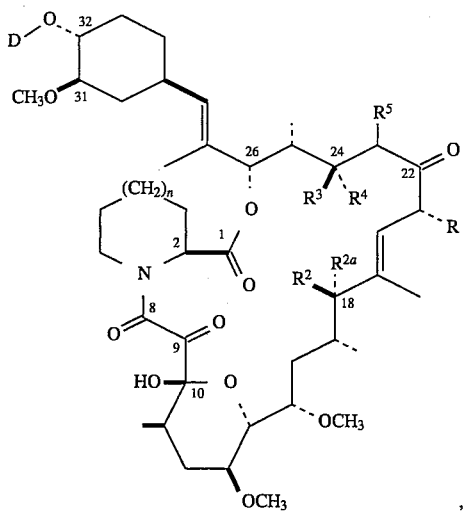

(IV)

wherein n, R, $R^2$, $R^{2a}$, $R^3$, $R^4$ and $R^5$ are as defined in claim 1, and D is a radical having a formula selected from the group consisting of:

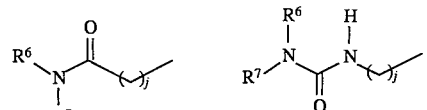

where j, $R^6$ and $R^7$ are as defined in claim 1.

5. A compound according to claim 1, selected from the group consisting of:

a compound wherein $R^1$ attaches to C-32 with R configuration and R=ethyl; n=1; $R^2=R^{2a}=R^3=R^5=H$; $R^4=OH$; $R^{1a}=OCH_3$; and $R^1=$—$OCH_2C(O)OC_2H_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)OCH_2C_6H_5$;

a compound wherein $R^1$ attaches to C-32 with R configuration and, wherein R=ethyl; n=1; $R^2=R^2a=R^3=R^5=H$; $R^4=OH$; $R^{1a}=OCH_3$; and $R^1=$—$OCH_2C(O)OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHCH_2Ph$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)CH_2Ph$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHCH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHC_2H_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)C_2H_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHCH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHCH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)CH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(cyclopropyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(CH_2CH_2CH_2CH_3)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(cyclobutyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH_2CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH_2CH(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(cyclopentyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH_2CH_2CH_2CH_2CH_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(cyclohexyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NR_{14}R^{15}$, where $R^{14}$ and $R^{15}$, taken together=—$CH_2CH_2OCH_2CH_2$—, a six-membered ring incorporating the nitrogen to which $R^{14}$ and $R^{15}$ are attached;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2CH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2NH_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2NH_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CH_2CH_2NH_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CO_2CH_2Ph$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CO_2H$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CO_2Ph$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH_2CH_2CO_2H$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_3)CO_2H$ (R configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_3)CO_2H$ (S configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_3)CONHCH(CH_3)CONHCH(CH_3)CO_2H$, where all chiral centers in $R^1$ are of R configuration;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(3$-phenyl-phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_2CH_2OH)(3$-phenyl-phenyl); phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N\{CH_2CH_2N(CH_3)(CH_2CH_2OH)\}(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N\{CH_2CH_2N(CH_3)_2\}(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N\{CH_2(3$-pyridyl)$\}\{CH_2(3$-pyridyl)$\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(cyclohexyl)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH-(4-morpholinyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(4-thiomorpholinyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH(4-CF$_3$-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH(4-F-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH{4-(4-morpholino)-phenyl};

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(4-HO-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH(3-pyridyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(4-pyridyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(2-pyridyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)N(CH$_3$)CH$_2$CH$_2$OH;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(NHCO$_2$CH$_3$);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)-L-prolinocarboxamide;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)-D-prolinocarboxamide;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)-L-prolinol;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)-D-prolinol;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)N(CH$_2$CH$_2$OH)NHCO$_2$CH$_3$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH{3-(phenylethynyl)phenyl};

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)N(CH$_2$CH$_2$CH$_2$OH)(4-fluorophenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)N(CH$_2$CH$_2$CH$_2$OCOCH$_2$CH$_2$CO$_2$H)(4-fluorophenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NR$^{14}$R$^{15}$, where $R^{14}$ and $R^{15}$, taken together, are the diradical, —CH$_2$CH$_2$C(OCH$_2$CH$_2$O)CH$_2$CH$_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NHNH{CO-(4-pyridyl)};

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(3-fluorophenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(3-hydroxy-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NR$^{14}$R$^{15}$, where $R^{14}$ and $R^{15}$, taken together, are the diradical, —CH$_2$CH$_2$—NCH$_3$—CH$_2$CH$_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH{6-(1,4-benzodioxanyl)};

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH(3,4-methylenedioxy-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NH(1-naphthalenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NR$^{14}$R$^{15}$; where $R^{14}$ and $R^{15}$, taken together =—CH$_2$CH$_2$CH$_2$CH$_2$—, ta five-membered ring incorporating the nitrogen to which $R^{14}$ and $R^{15}$ are attached;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1$ =—OCH$_2$C(O)NR$^{14}$R$^{15}$; where $R^{14}$ and $R^{15}$, taken together =—CH$_2$CH$_2$CH$_2$CH$_2$CH$_2$—, a six-membered ring incorporating the nitrogen to which $R^{14}$ and $R^{15}$ are attached;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)OCH$_2$-(9-fluorenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)OH;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)NHCH$_2$CH$_2$C$_6$H$_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—OCH$_2$C(O)N(CH$_3$)CH$_2$CH$_2$C$_6$H$_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —OCH$_2$C(O)NH(CH$_2$)$_5$NH-dansyl;

a compound wherein $R^1$ attaches to C-32 with R configuration and, wherein R=ethyl; n=1 $R^2=R^{2a}=R^3=R^5=H$; $R^4=OH$; $R^{1a}=OCH_3$; and $R^1=$ —$OCH_2C(O)NHC_6H_5$;

a compound wherein $R^1$ attaches to C-32 with R configuration and, wherein R=ethyl; n=1 $R^2=R^{2a}=R^3=R^5=H$; $R^4=OH$; $R^{1a}=OCH_3$; and $R^1=$ —$OCH_2C(O)NH(CH_2)_2N(CH_2CH_2)_2O$;

a compound wherein $R^1$ attaches to C-32 with R configuration and, wherein R=ethyl; n=1 $R^2=R^{2a}=R^3=R^5=H$; $R^4=OH$; $R^{1a}=OCH_3$; and $R^1=$ —$OCH_2C(O)NH(CH_2)_3N(CH_2CH_2)_2O$;

a compound wherein $R^1$ attaches to C-32 with R configuration and, wherein R=ethyl; n=1 $R^2=R^{2a}=R^3=R^5=H$; $R^4=OH$; $R^{1a}=OCH_3$; and $R^1=$ —$OCH_2C(O)NH(CH_2)_2N(CH_3)_2$;

a compound wherein $R^1$ attaches to C-32 with R configuration and, wherein R=ethyl; n=1 $R^2=R^{2a}=R^3=R^5=H$; $R^4=OH$; $R^{1a}=OCH_3$; and $R^1=$ —$OCH_2C(O)NH(CH_2)_3N(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_2C_6H_5)CO_2CH_2Ph$ (S configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_2C_6H_5)CO_2H$ (S configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_2C_6H_5)CO_2CH_2Ph$ (R configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NHCH(CH_2C_6H_5)CO_2H$ (R configuration);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(CH_2)_2SH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(CH_2)_3SH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)OC_2H5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(2$-naphthyl);

a compound wherein $R^1$ attaches to C-32 with R configuration and, wherein R=ethyl; n=1; $R^2=R^{2a}=R^3=H$; $R^{1a}=OCH_3$; $R^1=$ —$OCH_2C(O)OCH_2Ph$; and $R^4$ and $R^5$, taken together, form a bond;

a compound wherein $R^1$ attaches to C-32 with R configuration and, wherein R=ethyl; n=1; $R^2=R^{2a}=R^3=R^4=R^5=H$; $R^{1a}=OCH_3$; and $R^1=$ —$OCH_2C(O)OH$;

a compound wherein $R^1$ attaches to C-32 with R configuration and, wherein R=ethyl; n=1; $R^2=R^{2a}=R^3=R^4=R^5=H$; $R^{1a}=OCH_3$; and $R^1=$ —$OCH_2C(O)NR^{14}R^{15}$, where $R^{14}$ and $R^{15}$, taken together, are the diradical, —$CH_2CH_2OCH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH\{4\text{-}(H_2NSO_2)\text{-phenyl}\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NR^{14}R^{15}$, $R^{14}$ and $R^{15}$, taken together, are the diradical, —$CH_2CH_2N(CH_2CH_2OH)CH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_2CH_2OH)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_3)CH_2CH_2CH_2N(CH_3)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(phenyl)CH_2CH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH\{CH(CH_2OH)_2\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH\{3\text{-}(CF_3)\text{-phenyl}\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)N(CH_2CN)_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NR^{14}R^{15}$, where $R^{14}$ and $R^{15}$, taken together, form the diradical, —$CH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2NH(CO)NR^{14}R^{15}$, where $R^{14}$ and $R^{15}$, taken together, form the diradical, —$CH_2CH_2OCH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2NH(CO)NH(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2NHC(O)(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)OCH_2C_6H_5$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2NH(CO)NHCH_2CH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH(6$-carbomethoxymethylmercaptopurine hydrazidyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NR^{14}R^{15}$, where $R^{14}$ and $R^{15}$, taken together, form the diradical, —$CH_2CH_2SO_2CH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$ —$OCH_2C(O)NH\{CH_2CH_2\text{-}(4\text{-F-phenyl})\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(4$-Cl-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH\{4$-$(OCH_3)$-phenyl\};

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(4$-$CH_3$-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(3,4$-$Cl_2$-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(3$-I-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)O$-$CH_2$-$[(1R)$-$(+)$-alpha-pinen-10-yl)];

a compound wherein $R^1$ attaches to C-32 with R configuration and, wherein R=ethyl; n=1; $R^2=R^{2a}=R^3=R^5=H$; $R^4=OSi(CH_3)_3$; $R^{1a}=OCH_3$; and $R^1=$—$OCH_2C(O)O$-$CH_2$-$[(1R)$-$(+)$-a-pinen-10-yl)];

a compound wherein $R^1$ attaches to C-32 with R configuration and, wherein R=ethyl; n=1; $R^2=R^{2a}=R^3=H$; $R^4$ and $R^5$, taken together, form a bond; $R^{1a}=OCH_3$; and $R^1=$—$OCH_2C(O)(4$-(morpholinyl));

a compound wherein $R^1$ attaches to C-32 with R configuration and, wherein R=ethyl; n=1; $R^2=R^3=R^5=H$; $R^{2a}=R^4=OH$; $R^{1a}=OCH_3$; and $R^1=$—$OCH_2C(O)NH$-$(3$-fluoro-phenyl); or a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)O$-$(4$-nitrophenyl).

6. A compound according to claim 5, selected from the group consisting of:

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH_2$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NR^{14}R^{15}$, where $R^{14}$ and $R^{15}$ taken together=—$CH_2CH_2OCH_2CH_2$—, a six-membered ring incorporating the nitrogen to which $R^{14}$ and $R^{15}$ are attached;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(CH_2CH_2CH_2OH)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHCH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2NH(CO)NHCH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2NH(CO)NHCH_2CH_2OH$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH$-$(4$-morpholinyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(4$-HO-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2NH(CO)NH(phenyl)$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(3$-hydroxy-phenyl);

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NR^{14}R^{15}$; $R^{14}$ and $R^{15}$, taken together, are the diradical, —$CH_2CH_2$—$NCH_3$—$CH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NR^{14}R^{15}$, where $R^{14}$ and $R^{15}$, taken together, are the diradical, —$CH_2CH_2C(OCH_2CH_2O)CH_2CH_2$—;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NHNH\{CO$-$(4$-pyridyl)\}$;

a compound wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)N(CH_3)CH_2CH_2C_6H_5$;

a compound wherein $R^1$ attaches to C-32 with R configuration and, R=ethyl; n=1; $R^2=R^{2a}=R^3=R^5=H$; $R^4=OH$; $R^{1a}=OCH_3$; $R^1=$—$OCH_2C(O)N[(CH_2)_2N(CH_2CH_2)_2O][$-$CH_2CH_2OH]$;

a compound wherein $R^1$ attaches to C-32 with R configuration and, R=ethyl; n=1; $R^2=R^{2a}=R^3=R^5=H$; $R^4=OH$; $R^{1a}=OCH_3$; $R^1=$—$OCH_2C(O)OCH_2CCl_3$; and a compound wherein $R^1$ attaches to C-32 with R configuration and, R=ethyl; n=1; $R^2=R^{2a}=R^3=R^5=H$; $R^4=OH$; $R^{1a}=OCH_3$; $R^1=$—$OCH_2C(O)Cl$.

7. A compound according to claim 1 wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH\{4$-$(4$-morpholino$)$-phenyl\}$.

8. A compound according to claim 1 wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(4$-OH-phenyl).

9. A compound according to claim 1 wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH(3$-hydroxy-phenyl).

10. A compound according to claim 1 wherein $R^1$ attaches to C-32 with R configuration and, wherein R=ethyl; n=1; $R^2=R^{2a}=R^3=R^5=H$; $R^4=OH$; $R^{1a}=OCH_3$; and $R^1=$—$OCH_2C(O)NH\{4$-$(H_2NSO_2)$-phenyl\}$.

* * * * *

UNITED STATES PATENT AND TRADEMARK OFFICE
CERTIFICATE OF CORRECTION

PATENT NO. : 5,563,172
DATED : October 8, 1996
INVENTOR(S) : Wagner, et. Al.

It is certified that error appears in the above-indentified patent and that said Letters Patent is hereby corrected as shown below:

Column 83, line 51, change "-O(CH$_2$)jC(O)R$^{12}$" to -- -O(CH$_2$)$_j$C(O)R$^{12}$--.

Column 85, line 34, change "med" to --mod--.

Column 85, line 37, change "med-Het" to --mod-Het--.

Column 88, line 52, change "-O(CH$_2$)jCN" to -- -O(CH$_2$)$_j$CN--.

Column 88, line 53, change "O(CH$^2$)jC" to --O(CH$_2$)$_j$C--.

Column 88, line 55, change "O(CH$_2$)jC" to --O(CH$_2$)$_j$C--.

Column 88, line 58, change "O(CH$_2$)jC" to --O(CH$_2$)$_j$C--.

Column 88, line 60, change "O(CH$_2$)jC" to --O(CH$_2$)$_j$C--.

Column 88, line 63, change "(CH$_2$)jC" to --(CH$_2$)$_j$C--.

Column 88, line 65, change "O(CH$_2$)jNR$^6$" to --O(CH$_2$)$_j$NR$^6$--.

Column 89, line 1, change "O(CH$_2$)jNR$^6$" to --O(CH$_2$)$_j$NR$^6$--.

Column 89, line 3, change "O(CH$_2$)jNR$^6$" to --O(CH$_2$)$_j$NR$^6$--.

Column 89, line 5, change "O(CH$_2$)jNR$^6$" to --O(CH$_2$)$_j$NR$^6$--.

Column 89, line 7, change "O(CH$_2$)jNR$^6$" to --O(CH$_2$)$_j$NR$^6$--.

Column 90, line 37, change "C$_1$-C6-alkyl" to --C$_1$-C$_6$-alkyl--.

UNITED STATES PATENT AND TRADEMARK OFFICE
CERTIFICATE OF CORRECTION

PATENT NO. : 5,563,172
DATED : October 8, 1996
INVENTOR(S) : Wagner, et. Al.

It is certified that error appears in the above-indentified patent and that said Letters Patent is hereby corrected as shown below:

Column 93, line 19, change "-$OCH_2C(O)NHCH_2CH_2CH_2CH_3$" to -- -$OCH_2C(O)NHCH_2CH_2CH_2CH_2CH_3$--.

Column 93, line 49, change "-$OCH_2C(O)NR_{14}R^{15}$" to -- -$OCH_2C(O)NR^{14}R^{15}$--.

Column 94, line 27, change "$OCH_2C(O)NHCH_2CH_2CO_2Ph$" to --$OCH_2C(O)NHCH_2CH_2CO_2CH_2Ph$--.

Column 94, lines 42-43, change "$OCH_2C(O)NHCH(CH_3)CONHCH(CH_3)CONHCH(CH_3)CO_2H$" to --$OCH_2C(O)NHCH(CH3)CONHCH(CH3)CONHCH(CH3)CO2H$--.

Column 94, lines 51-52, delete the second occurrence of "phenyl);".

Column 96, line 10, change "-$CH_2CH_2C(OCH_2CH_2O)CH_2CH_2$;" to -- -$CH_2CH_2C(OCH_2CH_2O)CH_2CH_2$-;--.

Column 97, line 47, change "-$OCH_2C(O)OC_2H5$" to -- -$OCH_2C(O)OC_2H_5$--.

Column 100, line 50, change "claim 1" to --claim 5--.

UNITED STATES PATENT AND TRADEMARK OFFICE
CERTIFICATE OF CORRECTION

PATENT NO. : 5,563,172
DATED : October 8, 1996
INVENTOR(S) : Wagner, et al.

It is certified that error appears in the above-indentified patent and that said Letters Patent is hereby corrected as shown below:

Column 100, line 54, change "claim 1" to --claim 5--.

Signed and Sealed this

Fifteenth Day of April, 1997

Attest:

BRUCE LEHMAN

*Attesting Officer*     *Commissioner of Patents and Trademarks*